(12) United States Patent
Hahn et al.

(10) Patent No.: US 10,126,377 B2
(45) Date of Patent: Nov. 13, 2018

(54) MAGNETO-OPTICAL DEFECT CENTER MAGNETOMETER

(71) Applicant: LOCKHEED MARTIN CORPORATION, Bethesda, MD (US)

(72) Inventors: Joseph W. Hahn, Erial, NJ (US); Arul Manickam, Mount Laurel, NJ (US); Peter G. Kaup, Marlton, NJ (US); Gregory Scott Bruce, Abington, PA (US); Wilbur Lew, Mount Laurel, NJ (US); Nicholas M. Luzod, Seattle, WA (US); Duc Huynh, Princeton Junction, NJ (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 0 days.

(21) Appl. No.: 15/672,953

(22) Filed: Aug. 9, 2017

(65) Prior Publication Data

US 2017/0363696 A1    Dec. 21, 2017

Related U.S. Application Data

(63) Continuation of application No. 15/456,913, filed on Mar. 13, 2017, which is a continuation-in-part of
(Continued)

(51) Int. Cl.
*G01R 33/032*    (2006.01)
*G01N 21/64*    (2006.01)
(Continued)

(52) U.S. Cl.
CPC .......... *G01R 33/032* (2013.01); *G01N 21/64* (2013.01); *G01R 33/1284* (2013.01);
(Continued)

(58) Field of Classification Search
CPC .. B64G 1/366; G01N 24/006; G01N 33/0206; G01N 33/028; G01N 33/038;
(Continued)

(56) References Cited

U.S. PATENT DOCUMENTS 2,746,027 A    5/1956   Murray
3,359,812 A    12/1967  Everitt
(Continued)

FOREIGN PATENT DOCUMENTS

CN    105738845 A    7/2016
DE    69608006 T2    2/2001
(Continued)

OTHER PUBLICATIONS

U.S. Notice of Allowance dated Aug. 11, 2017 from related U.S. Appl. No. 15/003,558, 5 pages.
(Continued)

*Primary Examiner* — Tung X Nguyen
*Assistant Examiner* — Robert P Alejnikov, Jr.
(74) *Attorney, Agent, or Firm* — Foley & Lardner LLP

(57) ABSTRACT

A magneto-optical defect center magnetometer, such as a diamond nitrogen vacancy (DNV) magnetometer, can include an excitation source, a magneto-optical defect center element, a collection device, a top plate, a bottom plate, and a printed circuit board. The excitation source, the magneto-optical defect center element, and the collection device are each mounted to the printed circuit board.

28 Claims, 34 Drawing Sheets

Related U.S. Application Data application No. 15/382,045, filed on Dec. 16, 2016, which is a continuation-in-part of application No. 15/380,691, filed on Dec. 15, 2016, which is a continuation-in-part of application No. 15/380,419, filed on Dec. 15, 2016.

(60) Provisional application No. 62/343,746, filed on May 31, 2016, provisional application No. 62/343,750, filed on May 31, 2016, provisional application No. 62/343,818, filed on May 31, 2016, provisional application No. 62/343,843, filed on May 31, 2016, provisional application No. 62/343,602, filed on May 31, 2016, provisional application No. 62/343,600, filed on May 31, 2016, provisional application No. 62/343,492, filed on May 31, 2016, provisional application No. 62/343,758, filed on May 31, 2016.

(51) Int. Cl.
*G01R 33/26* (2006.01)
*G01R 33/12* (2006.01)
*G01N 21/87* (2006.01)

(52) U.S. Cl.
CPC ............ *G01R 33/26* (2013.01); *G01N 21/87* (2013.01); *G01N 2201/06113* (2013.01)

(58) Field of Classification Search
CPC .. G01N 33/1215; G01N 33/032; G01N 33/26; G01N 33/1284; G01N 21/64; G01N 21/87; G01N 2201/06113; G01N 21/6428; G01N 21/6408; G01N 21/645; G01N 21/6452
USPC .......................... 324/244.1; 250/458.1–467.1
See application file for complete search history.

(56) References Cited

U.S. PATENT DOCUMENTS

| | | |
|---|---|---|
| 3,389,333 A | 6/1968 | Wolff et al. |
| 3,490,032 A | 1/1970 | Zurflueh |
| 3,514,723 A | 5/1970 | Cutler |
| 3,518,531 A | 6/1970 | Huggett |
| 3,621,380 A | 11/1971 | Barlow, Jr. |
| 3,745,452 A | 7/1973 | Osburn et al. |
| 3,899,758 A | 8/1975 | Maier et al. |
| 4,025,873 A | 5/1977 | Chilluffo |
| 4,047,805 A | 9/1977 | Sekimura |
| 4,078,247 A | 3/1978 | Albrecht |
| 4,084,215 A | 4/1978 | Willenbrock |
| 4,322,769 A | 3/1982 | Cooper |
| 4,329,173 A | 5/1982 | Culling |
| 4,359,673 A | 11/1982 | Bross et al. |
| 4,368,430 A | 1/1983 | Dale et al. |
| 4,410,926 A | 10/1983 | Hafner et al. |
| 4,437,533 A | 3/1984 | Bierkarre et al. |
| 4,514,083 A | 4/1985 | Fukuoka |
| 4,588,993 A | 5/1986 | Babij et al. |
| 4,636,612 A | 1/1987 | Cullen |
| 4,638,324 A | 1/1987 | Hannan |
| 4,675,522 A | 6/1987 | Arunkumar |
| 4,768,962 A | 9/1988 | Kupfer et al. |
| 4,818,990 A | 4/1989 | Fernandes |
| 4,820,986 A | 4/1989 | Mansfield et al. |
| 4,945,305 A | 7/1990 | Blood |
| 4,958,328 A | 9/1990 | Stubblefield |
| 4,982,158 A | 1/1991 | Nakata et al. |
| 5,019,721 A | 5/1991 | Martens et al. |
| 5,038,103 A | 8/1991 | Scarzello et al. |
| 5,113,136 A | 5/1992 | Hayashi et al. |
| 5,134,369 A | 7/1992 | Lo et al. |
| 5,189,368 A | 2/1993 | Chase |
| 5,200,855 A | 4/1993 | Meredith et al. |
| 5,245,347 A | 9/1993 | Bonta et al. |
| 5,252,912 A | 10/1993 | Merritt et al. |
| 5,301,096 A | 4/1994 | Klontz et al. |
| 5,384,109 A | 1/1995 | Klaveness et al. |
| 5,396,802 A | 3/1995 | Moss |
| 5,420,549 A | 5/1995 | Prestage |
| 5,425,179 A | 6/1995 | Nickel et al. |
| 5,427,915 A | 6/1995 | Ribi et al. |
| 5,548,279 A | 8/1996 | Gaines |
| 5,568,516 A | 10/1996 | Strohallen et al. |
| 5,586,069 A | 12/1996 | Dockser |
| 5,597,762 A | 1/1997 | Popovici et al. |
| 5,638,472 A | 6/1997 | Van Delden |
| 5,694,375 A | 12/1997 | Woodall |
| 5,719,497 A | 2/1998 | Veeser et al. |
| 5,731,996 A | 3/1998 | Gilbert |
| 5,764,061 A | 6/1998 | Asakawa et al. |
| 5,818,352 A | 10/1998 | McClure |
| 5,846,708 A | 12/1998 | Hollis et al. |
| 5,888,925 A | 3/1999 | Smith et al. |
| 5,907,420 A | 5/1999 | Chraplyvy et al. |
| 5,907,907 A | 6/1999 | Ohtomo et al. |
| 5,915,061 A * | 6/1999 | Vanoli ................ H01S 3/06704 385/135 |
| 6,042,249 A | 3/2000 | Spangenberg |
| 6,057,684 A | 5/2000 | Murakami et al. |
| 6,124,862 A | 9/2000 | Boyken et al. |
| 6,130,753 A | 10/2000 | Hopkins et al. |
| 6,144,204 A | 11/2000 | Sementchenko |
| 6,195,231 B1 | 2/2001 | Sedlmayr et al. |
| 6,215,303 B1 | 4/2001 | Weinstock et al. |
| 6,360,173 B1 | 3/2002 | Fullerton |
| 6,398,155 B1 | 6/2002 | Hepner et al. |
| 6,433,944 B1 | 8/2002 | Nagao et al. |
| 6,472,651 B1 | 10/2002 | Ukai |
| 6,472,869 B1 | 10/2002 | Upschulte et al. |
| 6,504,365 B2 | 1/2003 | Kitamura |
| 6,542,242 B1 | 4/2003 | Yost et al. |
| 6,621,578 B1 | 9/2003 | Mizoguchi |
| 6,636,146 B1 | 10/2003 | Wehoski |
| 6,686,696 B2 | 2/2004 | Mearini et al. |
| 6,690,162 B1 | 2/2004 | Schopohl et al. |
| 6,765,487 B1 | 7/2004 | Holmes et al. |
| 6,788,722 B1 | 9/2004 | Kennedy et al. |
| 6,809,829 B1 | 10/2004 | Takata et al. |
| 7,118,657 B2 | 10/2006 | Golovchenko et al. |
| 7,221,164 B1 | 5/2007 | Barringer |
| 7,277,161 B2 | 10/2007 | Claus |
| 7,305,869 B1 | 12/2007 | Berman et al. |
| 7,307,416 B2 | 12/2007 | Islam et al. |
| 7,342,399 B1 | 3/2008 | Wiegert |
| RE40,343 E | 5/2008 | Anderson |
| 7,400,142 B2 | 7/2008 | Greelish |
| 7,413,011 B1 | 8/2008 | Chee et al. |
| 7,427,525 B2 | 9/2008 | Santori et al. |
| 7,448,548 B1 | 11/2008 | Compton |
| 7,471,805 B2 | 12/2008 | Goldberg |
| 7,474,090 B2 | 1/2009 | Islam et al. |
| 7,543,780 B1 | 6/2009 | Marshall et al. |
| 7,546,000 B2 | 6/2009 | Spillane et al. |
| 7,570,050 B2 | 8/2009 | Sugiura |
| 7,608,820 B1 | 10/2009 | Berman et al. |
| 7,705,599 B2 | 4/2010 | Strack et al. |
| 7,805,030 B2 | 9/2010 | Bratkovski et al. |
| 7,868,702 B2 | 1/2011 | Ohnishi |
| 7,889,484 B2 | 2/2011 | Choi |
| 7,916,489 B2 | 3/2011 | Okuya |
| 7,932,718 B1 | 4/2011 | Wiegert |
| 7,983,812 B2 | 7/2011 | Potter |
| 8,022,693 B2 | 9/2011 | Meyersweissflog |
| 8,120,351 B2 | 2/2012 | Rettig et al. |
| 8,120,355 B1 | 2/2012 | Stetson |
| 8,124,296 B1 | 2/2012 | Fischel |
| 8,138,756 B2 | 3/2012 | Barclay et al. |
| 8,193,808 B2 | 6/2012 | Fu et al. |
| 8,294,306 B2 | 10/2012 | Kumar et al. |
| 8,310,251 B2 | 11/2012 | Orazem |
| 8,311,767 B1 | 11/2012 | Stetson |
| 8,334,690 B2 | 12/2012 | Kitching et al. |

(56) References Cited

U.S. PATENT DOCUMENTS

| | | |
|---|---|---|
| 8,415,640 B2 | 4/2013 | Babinec et al. |
| 8,471,137 B2 | 6/2013 | Adair et al. |
| 8,480,653 B2 | 7/2013 | Birchard et al. |
| 8,525,516 B2 | 9/2013 | Le Prado et al. |
| 8,547,090 B2 | 10/2013 | Lukin et al. |
| 8,574,536 B2 | 11/2013 | Boudou et al. |
| 8,575,929 B1 | 11/2013 | Wiegert |
| 8,686,377 B2 | 4/2014 | Twitchen et al. |
| 8,704,546 B2 | 4/2014 | Konstantinov |
| 8,758,509 B2 | 6/2014 | Twitchen et al. |
| 8,803,513 B2 | 8/2014 | Hosek et al. |
| 8,854,839 B2 | 10/2014 | Cheng et al. |
| 8,885,301 B1 | 11/2014 | Heidmann |
| 8,913,900 B2 | 12/2014 | Lukin et al. |
| 8,933,594 B2 | 1/2015 | Kurs |
| 8,947,080 B2 | 2/2015 | Lukin et al. |
| 8,963,488 B2 | 2/2015 | Campanella et al. |
| 9,103,873 B1 | 8/2015 | Martens et al. |
| 9,157,859 B2 | 10/2015 | Walsworth et al. |
| 9,245,551 B2 | 1/2016 | El Hallak et al. |
| 9,249,526 B2 | 2/2016 | Twitchen et al. |
| 9,291,508 B1 | 3/2016 | Biedermann et al. |
| 9,369,182 B2 | 6/2016 | Kurs et al. |
| 9,442,205 B2 | 9/2016 | Geiser et al. |
| 9,541,610 B2 | 1/2017 | Kaup et al. |
| 9,551,763 B1 | 1/2017 | Hahn et al. |
| 9,557,391 B2 | 1/2017 | Egan et al. |
| 9,570,793 B2 | 2/2017 | Borodulin |
| 9,590,601 B2 | 3/2017 | Krause et al. |
| 9,614,589 B1 | 4/2017 | Russo et al. |
| 9,645,223 B2 | 5/2017 | Megdal et al. |
| 9,680,338 B2 | 6/2017 | Malpas et al. |
| 9,689,679 B2 | 6/2017 | Budker et al. |
| 9,720,055 B1 | 8/2017 | Hahn et al. |
| 9,778,329 B2 | 10/2017 | Heidmann |
| 2002/0144093 A1 | 10/2002 | Inoue et al. |
| 2002/0167306 A1 | 11/2002 | Zalunardo et al. |
| 2003/0058346 A1 | 3/2003 | Bechtel et al. |
| 2003/0076229 A1 | 4/2003 | Blanpain et al. |
| 2003/0098455 A1 | 5/2003 | Amin et al. |
| 2003/0235136 A1 | 12/2003 | Akselrod et al. |
| 2004/0013180 A1 | 1/2004 | Giannakis et al. |
| 2004/0022179 A1 | 2/2004 | Giannakis et al. |
| 2004/0042150 A1 | 3/2004 | Swinbanks et al. |
| 2004/0081033 A1 | 4/2004 | Arieli et al. |
| 2004/0109328 A1 | 6/2004 | Dahl et al. |
| 2004/0247145 A1 | 12/2004 | Luo et al. |
| 2005/0031840 A1 | 2/2005 | Swift et al. |
| 2005/0068249 A1 | 3/2005 | Frederick Du Toit et al. |
| 2005/0099177 A1 | 5/2005 | Greelish |
| 2005/0112594 A1 | 5/2005 | Grossman |
| 2005/0126905 A1 | 6/2005 | Golovchenko et al. |
| 2005/0130601 A1 | 6/2005 | Palermo et al. |
| 2005/0134257 A1 | 6/2005 | Etherington et al. |
| 2005/0138330 A1 | 6/2005 | Owens et al. |
| 2005/0146327 A1 | 7/2005 | Jakab |
| 2006/0012385 A1 | 1/2006 | Tsao et al. |
| 2006/0054789 A1 | 3/2006 | Miyamoto et al. |
| 2006/0055584 A1 | 3/2006 | Waite et al. |
| 2006/0062084 A1 | 3/2006 | Drew |
| 2006/0071709 A1 | 4/2006 | Maloberti et al. |
| 2006/0245078 A1* | 11/2006 | Kawamura .......... G02B 15/177 359/689 |
| 2006/0247847 A1 | 11/2006 | Carter et al. |
| 2006/0255801 A1 | 11/2006 | Ikeda |
| 2006/0291771 A1 | 12/2006 | Braunisch et al. |
| 2007/0004371 A1 | 1/2007 | Okanobu |
| 2007/0247147 A1 | 10/2007 | Xiang et al. |
| 2007/0273877 A1 | 11/2007 | Kawano et al. |
| 2008/0016677 A1 | 1/2008 | Creighton, IV |
| 2008/0048640 A1 | 2/2008 | Hull et al. |
| 2008/0078233 A1 | 4/2008 | Larson et al. |
| 2008/0089367 A1 | 4/2008 | Srinivasan et al. |
| 2008/0204004 A1 | 8/2008 | Anderson |
| 2008/0217516 A1 | 9/2008 | Suzuki et al. |
| 2008/0239265 A1 | 10/2008 | Den Boef |
| 2008/0253264 A1 | 10/2008 | Nagatomi et al. |
| 2008/0265895 A1 | 10/2008 | Strack et al. |
| 2008/0266050 A1 | 10/2008 | Crouse et al. |
| 2008/0299904 A1 | 12/2008 | Yi et al. |
| 2009/0015262 A1 | 1/2009 | Strack et al. |
| 2009/0042592 A1 | 2/2009 | Cho et al. |
| 2009/0058697 A1 | 3/2009 | Aas et al. |
| 2009/0060790 A1 | 3/2009 | Okaguchi et al. |
| 2009/0079417 A1 | 3/2009 | Mort et al. |
| 2009/0079426 A1 | 3/2009 | Anderson |
| 2009/0132100 A1 | 5/2009 | Shibata |
| 2009/0157331 A1 | 6/2009 | Van Netten |
| 2009/0161264 A1 | 6/2009 | Meyersweissflog |
| 2009/0195244 A1 | 8/2009 | Mouget et al. |
| 2009/0222208 A1 | 9/2009 | Speck |
| 2009/0243616 A1 | 10/2009 | Loehken et al. |
| 2009/0277702 A1 | 11/2009 | Kanada et al. |
| 2009/0310650 A1 | 12/2009 | Chester et al. |
| 2010/0004802 A1 | 1/2010 | Bodin et al. |
| 2010/0015438 A1 | 1/2010 | Williams et al. |
| 2010/0015918 A1 | 1/2010 | Liu et al. |
| 2010/0045269 A1 | 2/2010 | Lafranchise et al. |
| 2010/0071904 A1 | 3/2010 | Burns et al. |
| 2010/0102809 A1 | 4/2010 | May |
| 2010/0102820 A1 | 4/2010 | Martinez et al. |
| 2010/0134922 A1 | 6/2010 | Yamada et al. |
| 2010/0157305 A1 | 6/2010 | Henderson |
| 2010/0188081 A1 | 7/2010 | Lammegger |
| 2010/0237149 A1 | 9/2010 | Olmstead |
| 2010/0271016 A1 | 10/2010 | Barclay et al. |
| 2010/0271032 A1 | 10/2010 | Helwig |
| 2010/0277121 A1 | 11/2010 | Hall et al. |
| 2010/0308813 A1 | 12/2010 | Lukin et al. |
| 2010/0315079 A1 | 12/2010 | Lukin et al. |
| 2010/0321117 A1 | 12/2010 | Gan |
| 2010/0326042 A1 | 12/2010 | McLean et al. |
| 2011/0034393 A1 | 2/2011 | Justen et al. |
| 2011/0059704 A1 | 3/2011 | Norimatsu et al. |
| 2011/0062957 A1 | 3/2011 | Fu et al. |
| 2011/0066379 A1 | 3/2011 | Mes |
| 2011/0120890 A1 | 5/2011 | MacPherson et al. |
| 2011/0127999 A1 | 6/2011 | Lott et al. |
| 2011/0165862 A1 | 7/2011 | Yu et al. |
| 2011/0175604 A1 | 7/2011 | Polzer et al. |
| 2011/0176563 A1 | 7/2011 | Friel et al. |
| 2011/0243267 A1 | 10/2011 | Won et al. |
| 2011/0270078 A1 | 11/2011 | Wagenaar et al. |
| 2011/0279120 A1 | 11/2011 | Sudow et al. |
| 2011/0315988 A1* | 12/2011 | Yu ........................ H01L 27/14 257/52 |
| 2012/0016538 A1 | 1/2012 | Waite et al. |
| 2012/0019242 A1 | 1/2012 | Hollenberg et al. |
| 2012/0037803 A1 | 2/2012 | Strickland |
| 2012/0044014 A1 | 2/2012 | Stratakos et al. |
| 2012/0051996 A1 | 3/2012 | Scarsbrook et al. |
| 2012/0063505 A1 | 3/2012 | Okamura et al. |
| 2012/0087449 A1 | 4/2012 | Ling et al. |
| 2012/0089299 A1 | 4/2012 | Breed |
| 2012/0140219 A1 | 6/2012 | Cleary |
| 2012/0181020 A1 | 7/2012 | Barron et al. |
| 2012/0194068 A1 | 8/2012 | Cheng et al. |
| 2012/0203086 A1 | 8/2012 | Rorabaugh et al. |
| 2012/0232838 A1 | 9/2012 | Kemppi et al. |
| 2012/0235633 A1 | 9/2012 | Kesler et al. |
| 2012/0235634 A1 | 9/2012 | Hall et al. |
| 2012/0245885 A1 | 9/2012 | Kimishima |
| 2012/0257683 A1 | 10/2012 | Schwager et al. |
| 2012/0281843 A1 | 11/2012 | Christensen et al. |
| 2012/0326793 A1 | 12/2012 | Gan |
| 2013/0043863 A1 | 2/2013 | Ausserlechner et al. |
| 2013/0093424 A1 | 4/2013 | Blank et al. |
| 2013/0127518 A1 | 5/2013 | Nakao |
| 2013/0179074 A1 | 7/2013 | Haverinen |
| 2013/0215712 A1 | 8/2013 | Geiser et al. |
| 2013/0223805 A1 | 8/2013 | Ouyang et al. |
| 2013/0265042 A1* | 10/2013 | Kawabata ............. G01R 33/26 324/301 |
| 2013/0265782 A1 | 10/2013 | Barrena et al. |

(56) References Cited

U.S. PATENT DOCUMENTS

| | | |
|---|---|---|
| 2013/0270991 A1 | 10/2013 | Twitchen et al. |
| 2013/0279319 A1 | 10/2013 | Matozaki et al. |
| 2014/0012505 A1 | 1/2014 | Smith et al. |
| 2014/0037932 A1 | 2/2014 | Twitchen et al. |
| 2014/0044208 A1 | 2/2014 | Woodsum |
| 2014/0061510 A1 | 3/2014 | Twitchen et al. |
| 2014/0070622 A1 | 3/2014 | Keeling et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |
| 2014/0153363 A1 | 6/2014 | Juhasz et al. |
| 2014/0154792 A1 | 6/2014 | Moynihan et al. |
| 2014/0159652 A1 | 6/2014 | Hall et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0180627 A1 | 6/2014 | Naguib et al. |
| 2014/0191139 A1 | 7/2014 | Englund |
| 2014/0191752 A1 | 7/2014 | Walsworth et al. |
| 2014/0198463 A1 | 7/2014 | Klein |
| 2014/0210473 A1 | 7/2014 | Campbell et al. |
| 2014/0215985 A1 | 8/2014 | Pollklas |
| 2014/0225606 A1 | 8/2014 | Endo et al. |
| 2014/0247094 A1 | 9/2014 | Englund et al. |
| 2014/0265555 A1 | 9/2014 | Hall et al. |
| 2014/0272119 A1 | 9/2014 | Kushalappa et al. |
| 2014/0273826 A1 | 9/2014 | Want et al. |
| 2014/0291490 A1 | 10/2014 | Hanson et al. |
| 2014/0297067 A1 | 10/2014 | Malay |
| 2014/0306707 A1 | 10/2014 | Walsworth et al. |
| 2014/0327439 A1 | 11/2014 | Cappellaro et al. |
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009746 A1 | 1/2015 | Kucsko et al. |
| 2015/0015247 A1 | 1/2015 | Goodwill et al. |
| 2015/0018018 A1 | 1/2015 | Shen et al. |
| 2015/0022404 A1 | 1/2015 | Chen et al. |
| 2015/0048822 A1 | 2/2015 | Walsworth et al. |
| 2015/0054355 A1 | 2/2015 | Ben-Shalom et al. |
| 2015/0061590 A1 | 3/2015 | Widmer et al. |
| 2015/0090033 A1 | 4/2015 | Budker et al. |
| 2015/0128431 A1 | 5/2015 | Kuo |
| 2015/0137793 A1 | 5/2015 | Englund et al. |
| 2015/0153151 A1 | 6/2015 | Kochanski |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0288352 A1 | 10/2015 | Krause et al. |
| 2015/0299894 A1 | 10/2015 | Markham et al. |
| 2015/0303333 A1 | 10/2015 | Yu et al. |
| 2015/0314870 A1 | 11/2015 | Davies |
| 2015/0326030 A1 | 11/2015 | Malpas et al. |
| 2015/0326410 A1 | 11/2015 | Krause et al. |
| 2015/0354985 A1 | 12/2015 | Judkins et al. |
| 2015/0374250 A1 | 12/2015 | Hatano et al. |
| 2015/0377865 A1 | 12/2015 | Acosta et al. |
| 2015/0377987 A1 | 12/2015 | Menon et al. |
| 2016/0018269 A1 | 1/2016 | Maurer et al. |
| 2016/0031339 A1 | 2/2016 | Geo |
| 2016/0036529 A1 | 2/2016 | Griffith et al. |
| 2016/0052789 A1 | 2/2016 | Gaathon et al. |
| 2016/0054402 A1 | 2/2016 | Meriles |
| 2016/0071532 A9 | 3/2016 | Heidmann |
| 2016/0077167 A1 | 3/2016 | Heidmann |
| 2016/0097702 A1 | 4/2016 | Zhao et al. |
| 2016/0113507 A1* | 4/2016 | Reza .................. G01N 21/1717 356/477 |
| 2016/0131723 A1 | 5/2016 | Nagasaka |
| 2016/0139048 A1* | 5/2016 | Heidmann .............. G01N 21/63 250/459.1 |
| 2016/0146904 A1 | 5/2016 | Stetson, Jr. et al. |
| 2016/0161429 A1 | 6/2016 | Englund et al. |
| 2016/0214714 A1 | 7/2016 | Sekelsky |
| 2016/0216304 A1 | 7/2016 | Sekelsky |
| 2016/0216340 A1 | 7/2016 | Egan et al. |
| 2016/0216341 A1 | 7/2016 | Boesch et al. |
| 2016/0221441 A1 | 8/2016 | Hall et al. |
| 2016/0223621 A1 | 8/2016 | Kaup et al. |
| 2016/0231394 A1 | 8/2016 | Manickam et al. |
| 2016/0266220 A1 | 9/2016 | Sushkov et al. |
| 2016/0282427 A1 | 9/2016 | Heidmann |
| 2016/0291191 A1 | 10/2016 | Fukushima et al. |
| 2016/0313408 A1 | 10/2016 | Hatano et al. |
| 2016/0348277 A1 | 12/2016 | Markham et al. |
| 2016/0356863 A1 | 12/2016 | Boesch et al. |
| 2017/0010214 A1 | 1/2017 | Osawa et al. |
| 2017/0010334 A1 | 1/2017 | Krause et al. |
| 2017/0010338 A1 | 1/2017 | Bayat et al. |
| 2017/0010594 A1 | 1/2017 | Kottapalli et al. |
| 2017/0023487 A1 | 1/2017 | Boesch |
| 2017/0030982 A1 | 2/2017 | Jeske et al. |
| 2017/0038314 A1 | 2/2017 | Suyama et al. |
| 2017/0068012 A1 | 3/2017 | Fisk |
| 2017/0074660 A1 | 3/2017 | Gann et al. |
| 2017/0075020 A1 | 3/2017 | Gann et al. |
| 2017/0104426 A1 | 4/2017 | Mills |
| 2017/0138735 A1 | 5/2017 | Cappellaro et al. |
| 2017/0199156 A1 | 7/2017 | Villani et al. |
| 2017/0205526 A1 | 7/2017 | Meyer |
| 2017/0207823 A1 | 7/2017 | Russo et al. |
| 2017/0211947 A1 | 7/2017 | Fisk |
| 2017/0212046 A1 | 7/2017 | Cammerata |
| 2017/0212177 A1 | 7/2017 | Coar et al. |
| 2017/0212178 A1 | 7/2017 | Hahn et al. |
| 2017/0212179 A1 | 7/2017 | Hahn et al. |
| 2017/0212180 A1 | 7/2017 | Hahn et al. |
| 2017/0212181 A1 | 7/2017 | Coar et al. |
| 2017/0212182 A1 | 7/2017 | Hahn et al. |
| 2017/0212183 A1 | 7/2017 | Egan et al. |
| 2017/0212184 A1 | 7/2017 | Coar et al. |
| 2017/0212185 A1 | 7/2017 | Hahn et al. |
| 2017/0212186 A1 | 7/2017 | Hahn et al. |
| 2017/0212187 A1 | 7/2017 | Hahn et al. |
| 2017/0212190 A1 | 7/2017 | Reynolds et al. |
| 2017/0212258 A1 | 7/2017 | Fisk |
| 2017/0261629 A1 | 9/2017 | Gunnarsson et al. |
| 2017/0343617 A1 | 11/2017 | Manickam et al. |
| 2017/0343619 A1 | 11/2017 | Manickam et al. |
| 2017/0343621 A1 | 11/2017 | Hahn et al. |
| 2017/0343695 A1 | 11/2017 | Stetson et al. |

FOREIGN PATENT DOCUMENTS

| | | |
|---|---|---|
| DE | 19600241 C2 | 8/2002 |
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 A1 | 2/2015 |
| EP | 2 907 792 | 8/2015 |
| GB | 2 423 366 A | 8/2006 |
| GB | 2 433 737 | 7/2007 |
| GB | 2 482 596 | 2/2012 |

(56) References Cited

FOREIGN PATENT DOCUMENTS

| | | |
|---|---|---|
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 A1 | 7/1987 |
| WO | WO-88/04032 A1 | 6/1988 |
| WO | WO-95/33972 A1 | 12/1995 |
| WO | WO-2011/046403 A2 | 4/2011 |
| WO | WO-2011/153339 A1 | 12/2011 |
| WO | WO-2012/016977 A2 | 2/2012 |
| WO | WO-2012/084750 | 6/2012 |
| WO | WO-2013/059404 A1 | 4/2013 |
| WO | WO-2013/066446 A1 | 5/2013 |
| WO | WO-2013/066448 | 5/2013 |
| WO | WO-2013/093136 A1 | 6/2013 |
| WO | WO-2013/188732 A1 | 12/2013 |
| WO | WO-2013/190329 A1 | 12/2013 |
| WO | WO-2014/011286 A2 | 1/2014 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 A1 | 10/2014 |
| WO | WO-2014/210486 A1 | 12/2014 |
| WO | WO-2015/015172 A1 | 2/2015 |
| WO | WO-2015/142945 | 9/2015 |
| WO | WO-2015/157110 A1 | 10/2015 |
| WO | WO-2015/157290 A1 | 10/2015 |
| WO | WO-2015/158383 A1 | 10/2015 |
| WO | WO-2015/193156 A1 | 12/2015 |
| WO | PCT/US2016/014287 | 1/2016 |
| WO | PCT/US2016/014290 | 1/2016 |
| WO | PCT/US2016/014291 | 1/2016 |
| WO | PCT/US2016/014330 | 1/2016 |
| WO | PCT/US2016/014363 | 1/2016 |
| WO | PCT/US2016/014376 | 1/2016 |
| WO | PCT/US2016/014380 | 1/2016 |
| WO | PCT/US2016/014384 | 1/2016 |
| WO | PCT/US2016/014386 | 1/2016 |
| WO | PCT/US2016/014392 | 1/2016 |
| WO | PCT/US2016/014394 | 1/2016 |
| WO | PCT/US2016/014395 | 1/2016 |
| WO | PCT/US2016/014396 | 1/2016 |
| WO | WO-2016/075226 A1 | 5/2016 |
| WO | WO-2016/118756 A1 | 7/2016 |
| WO | WO-2016/118791 A1 | 7/2016 |
| WO | WO-2016/122965 A1 | 8/2016 |
| WO | WO-2016/122966 A1 | 8/2016 |
| WO | WO-2016/126435 A1 | 8/2016 |
| WO | WO-2016/126436 A1 | 8/2016 |
| WO | PCT/US2016/066566 | 12/2016 |
| WO | PCT/US2016/068320 | 12/2016 |
| WO | PCT/US2016/068344 | 12/2016 |
| WO | PCT/US2016/068366 | 12/2016 |
| WO | WO-2016/190909 A2 | 12/2016 |
| WO | WO-2017/007513 A1 | 1/2017 |
| WO | WO-2017/007514 A1 | 1/2017 |
| WO | WO-2017/014807 A1 | 1/2017 |
| WO | PCT/US2017/017321 | 2/2017 |
| WO | PCT/US2017/018099 | 2/2017 |
| WO | PCT/US2017/018701 | 2/2017 |
| WO | PCT/US2017/018709 | 2/2017 |
| WO | PCT/US2017/019411 | 2/2017 |
| WO | PCT/US2017/021593 | 3/2017 |
| WO | PCT/US2017/021811 | 3/2017 |
| WO | PCT/US2017/022118 | 3/2017 |
| WO | PCT/US2017/022279 | 3/2017 |
| WO | PCT/US2017/024165 | 3/2017 |
| WO | PCT/US2017/024167 | 3/2017 |
| WO | PCT/US2017/024168 | 3/2017 |
| WO | PCT/US2017/024169 | 3/2017 |
| WO | PCT/US2017/024171 | 3/2017 |
| WO | PCT/US2017/024172 | 3/2017 |
| WO | PCT/US2017/024173 | 3/2017 |
| WO | PCT/US2017/024174 | 3/2017 |
| WO | PCT/US2017/024175 | 3/2017 |
| WO | PCT/US2017/024177 | 3/2017 |
| WO | PCT/US2017/024179 | 3/2017 |
| WO | PCT/US2017/024180 | 3/2017 |
| WO | PCT/uS2017/024181 | 3/2017 |
| WO | PCT/US2017/024182 | 3/2017 |
| WO | WO-2017/039747 A1 | 3/2017 |
| WO | PCT/US2017/035315 | 5/2017 |
| WO | WO-2017/095454 A1 | 6/2017 |
| WO | WO-2017/127079 A1 | 7/2017 |
| WO | WO-2017/127080 A1 | 7/2017 |
| WO | WO-2017/127081 A1 | 7/2017 |
| WO | WO-2017/127085 A1 | 7/2017 |
| WO | WO-2017/127090 A1 | 7/2017 |
| WO | WO-2017/127091 A1 | 7/2017 |
| WO | WO-2017/127093 A1 | 7/2017 |
| WO | WO-2017/127094 A1 | 7/2017 |
| WO | WO-2017/127095 A1 | 7/2017 |
| WO | WO-2017/127096 A1 | 7/2017 |
| WO | WO-2017/127097 A1 | 7/2017 |
| WO | WO-2017/127098 A1 | 7/2017 |

OTHER PUBLICATIONS

U.S. Office Action dated Aug. 15, 2017 from related U.S. Appl. No. 15/003,281, 12 pages.

"'Diamond Sensors, Detectors, and Quantum Devices' in Patent Application Approval Process," Chemicals & Chemistry, pp. 1-6, (Feb 28, 2014), 6 pages.

"Findings from University of Stuttgart in physics reported," Science Letter, (Jul. 7, 2009), 2 pages.

"New Findings on Nitrogen from Ecole Normale Superieure Summarized (Magnetic imaging with an ensemble of nitrogen vacancy-centers in diamond)," Physics Week, pp. 1-2, (Jul. 21, 2015), 2 pages.

"Patent Issued for Diamond Sensors, Detectors, and Quantum Devices (U.S. Pat. No. 9,249,526)," Journal of Engineering, pp. 1-5 (Feb 15, 2016), 5 pages.

"Researchers Submit Patent Application, 'Diamond Sensors, Detectors, and Quantum Devices', for Approval," Chemicals & Chemistry, pp. 1-7, (Apr. 11, 2014), 7 pages.

Acosta et al., "Broadband magnetometry by infrared-absorption detection of nitrogen-vacancy ensembles in diamond," Appl. Phys. Letters 97: 174104 (Oct. 29, 2010), 4 pages.

Acosta et al., "Diamonds with a high density of nitrogen-vacancy centers for magnetometry applications," Physical Review B 80(115202): 1-15 (Sep. 9, 2009), 15 pages.

Acosta et al., "Nitrogen-vacancy centers: physics and applications," MRS Bulletin 38(2): 127-130 (Feb. 2013), 4 pages.

Acosta, "Optical Magnetometry with Nitrogen-Vacancy Centers in Diamond," University of California Berkeley, (Spring 2011), 118 pages.

(56) References Cited

OTHER PUBLICATIONS

Aiello et al., "Composite-pulse magnetometry with a solid-state quantum sensor," Nature Communications 4(1419): 1-6 (Jan. 29, 2013), 6 pages.

Alam, "Solid-state 13C magic angle spinning NMR spectroscopy characterization of particle size structural variations in synthetic nanodiamonds," Materials Chemistry and Physics 85(2-3): 310-315 (Jun. 15, 2004), 6 pages.

Albrecht et al., "Coupling of nitrogen vacancy centres in nanodiamonds by means of phonons," New Journal of Physics 15(083014): 1-26 (Aug. 6, 2013), 27 pages.

Appel et al., "Nanoscale microwave imaging with a single electron spin in diamond," New Journal of Physics 17(112001): 1-6 (Nov. 3, 2015), 7 pages.

Arai et al., "Fourier magnetic imaging with nanoscale resolution and compressed sensing speed-up using electronic spins in diamond," Nature Nanotechnology 10: 859-864 (Aug. 10, 2015), 7 pages.

Aslam et al., "Single spin optically detected magnetic resonance with 60-90 GHz (E-band) microwave resonators," Review of Scientific Instruments 86(064704): 1-8 (Jun. 22, 2015), 9 pages.

Awschalom et al., "Diamond age of spintronics," Scientific American 297: 84-91 (Oct. 2007), 8 pages.

Babamoradi et al., "Correlation between entanglement and spin density in nitrogen-vacancy center of diamond," European Physical Journal D 65: 597-603 (Dec. 1, 2011), 7 pages.

Babunts et al., "Diagnostics of NV defect structure orientation in diamond using optically detected magnetic resonance with a modulated magnetic field," Technical Physics Letters 41(6): 583-586 (Jun. 2015; first published online Jul. 14, 2015), 4 pages.

Babunts et al., "Temperature-scanned magnetic resonance and the evidence of two-way transfer of a nitrogen nuclear spin hyperfine interaction in coupled NV—N pairs in diamond," JETP Letters 95(8): 429-432 (Jun. 27, 2012), 4 pages.

Bagguley et al., "Zeeman effect of acceptor states in semiconducting diamond," Journal of the Physical Society of Japan 21(Supplement): 244-248 (1966), 7 pages.

Balasubramanian et al., "Nanoscale imaging magnetometry with diamond spins under ambient conditions," Nature 455: 648-651 (Oct. 2, 2008), 5 pages.

Balmer et al., "Chemical Vapour deposition synthetic diamond: materials technology and applications," J. of Physics: Condensed Matter 21(36): 1-51 (Aug. 19, 2009), 51 pages.

Baranov et al., "Enormously High Concentrations of Fluorescent Nitrogen-Vacancy Centers Fabricated by Sintering of Detonation Nanodiamonds," Small 7(11): 1533-1537 (Jun. 6, 2011; first published online Apr. 26, 2011), 5 pages.

Barfuss et al., "Strong mechanical driving of a single electron spin," Nature Physics 11: 820-824 (Aug. 3, 2015), 6 pages.

Barry et al., "Optical magnetic detection of single-neuron action potentials using quantum defects in diamond," as submitted to Quantum Physics on Feb. 2, 2016, 23 pages.

Bennett et al., "CVD Diamond for High Power Laser Applications," SPIE 8603, High-Power Laser Materials Processing: Lasers, Beam Delivery, Diagnostics, and Applications II, 860307 (Feb. 22, 2013), 10 pages.

Berman & Chernobrod, "Single-spin microscope with subnanoscale resolution based on optically detected magnetic resonance," SPIE 7608, Quantum Sensing and Nanophotonic Devices VII, 76080Y (Jan. 23, 2010), 4 pages.

Berman et al. "Measurement of single electron and nuclear spin states based on optically detected magnetic resonance," J. Physics: Conf. Series 38: 167-170 (2006), 5 pages.

Blakley et al., "Room-temperature magnetic gradiometry with fiber-coupled nitrogen-vacancy centers in diamond," Optics Letters 40(16): 3727-3730 (Aug. 5, 2015), 4 pages.

Bourgeois, et al., "Photoelectric detection of electron spin resonance of nitrogen-vacancy centres in diamond," Nature Communications 6(8577): 1-8 (Oct. 21, 2015), 8 pages.

Brenneis, et al. "Ultrafast electronic readout of diamond nitrogen-vacancy centres coupled to graphene." Nature nanotechnology 10.2 (2015): 135-139.

Bucher et al, "High Resolution Magnetic Resonance Spectroscopy Using Solid-State Spins", May 25, 2017, downloaded from https://arxiv.org/ (arXiv.org > quant-ph > arXiv:1705.08887) on May 25, 2017, pp. 1-24.

Budker & Kimball, "Optical Magnetometry," Cambridge Press, (2013), 11 pages.

Budker & Romalis, "Optical Magnetometry," Nature Physics 3: 227-243 (Apr. 2007), 8 pages.

Casanova, et al., "Effect of magnetic field on phosphorus centre in diamond," Physica Status Solidi A 186(2): 291-295 (Jul. 30, 2001), 6 pages.

Castelletto, et al., "Frontiers in diffraction unlimited optical methods for spin manipulation, magnetic field sensing and imaging using diamond nitrogen vacancy defects," Nanophotonics 1(2): 139-153 (Nov. 2012), 15 pages.

Chapman, et al., "Anomalous saturation effects due to optical spin depolarization in nitrogen-vacancy centers in diamond nanocrystals," Physical Review B 86(045204): 1-8 (Jul. 10, 2012), 8 pages.

Chavez, et al. "Detecting Arctic oil spills with NMR: a feasibility study." Near Surface Geophysics 13.4 (Feb. 2015): 409-416.

Chen et al., "Vector magnetic field sensing by a single nitrogen vacancy center in diamond," EPL 101(67003): 1-5 (Mar. 2013), 6 pages.

Chernobrod et al., "Improving the sensitivity of frequency modulation spectroscopy using nanomechanical cantilevers," Applied Physics Letters 85(17): 3896-3898 (Oct. 25, 2004), 3 pages.

Chernobrod et al., "Spin Microscope Based on Optically Detected Magnetic Resoncance," Journal of Applied Physics 97(014903): 1-3, (2005; first published online Dec. 10, 2004), 4 pages.

Childress et al., "Coherent dynamics of coupled electron and nuclear spin qubits in diamond," Science 314(5797): 281-285 (Oct. 13, 2006), 6 pages.

Chipaux et al., "Magnetic imaging with an ensemble of nitrogen vacancy-centers in diamond," European Physical Journal D 69(166): 1-10 (Jul. 2, 2015), 10 pages.

Chipaux et al., "Nitrogen vacancies (NV) centers in diamond for magnetic sensors and quantum sensing," SPIE 9370, Quantum Sensing and Nanophotonic Devices XII, 93701V (Feb. 8, 2015), 6 pages.

Chipaux, et al., "Wide bandwidth instantaneous radio frequency spectrum analyzer based on nitrogen vacancy centers in diamond," Applied Physics Letters 107(233502): 1-5 (2015), 6 pages.

Clevenson et al., "Broadband magnetometry and temperature sensing with a light-trapping diamond waveguide," Nature Physics 11: 393-397 (May 2015; first published online Apr. 6, 2015), 6 pages.

Constable, "Geomagnetic Spectrum, Temporal." In Encyclopedia of Geomagnetism and Paleomagnetism, pp. 353-355, Springer: Dordrecht, Netherlands (2007), 3 pages.

Cooper et al., "Time-resolved magnetic sensing with electronic spins in diamond," Nature Communications 5:3141: 1-7 (Jan. 24, 2014), 7 pages.

Creedon et al., "Strong coupling between P1 diamond impurity centers and a three-dimensional lumped photonic microwave cavity," Physical Review B 91(140408R): 1-5 (Apr. 24, 2015), 5 pages.

Dale, et al. "Medical applications of diamond magnetometry: commercial viability." arXiv preprint arXiv:1705.01994 (May 8, 2017), pp. 1-7.

Davies, "Current problems in diamond: towards a quantitative understanding," Physica B 273-274: 15-13 (Dec. 15, 1999), 9 pages.

De Lange et al., "Single-Spin Magnetometry with Multipulse Sensing Sequences," Physical Review Letters 106(080802): 1-4 (Feb. 24, 2011), 4 pages.

Degen, "Scanning magnetic field microscope with a diamond single-spin sensor," Applied Physics Letters 92(243111): 1-3 (Jun. 17, 2008), 3 pages.

Delacroix et al., "Design, manufacturing, and performance analysis of mid-infrared achromatic half-wave plates with diamond subwavelength gratings," Applied Optics 51(24): 5897-5902 (Aug. 16, 2012), 6 pages.

(56) References Cited

OTHER PUBLICATIONS

Denatale et al., "Fabrication and characterization of diamond moth eye antireflective surfaces on Ge," J. Of Applied Physics 71: 1388-1393 (Mar. 1992), 8 pages.

Dobrovitski et al., "Quantum Control over Single Spins in Diamond," Annual Review of Condensed Matter Physics 4: 23-50 (Apr. 2013), 30 pages.

Doherty et al., "The nitrogen-vacancy colour centre in diamond," Physics Reports 528: 1-45 (Jul. 1, 2013), 45 pages.

Doherty et al., "Theory of the ground-state spin of the NV-center in diamond," Physical Review B 85(205203): 1-21 (May 3, 2012), 21 pages.

Doi et al., "Pure negatively charged state of the NV center in n-type diamond," Physical Review B 93(081203): 1-6 (Feb. 3, 2016), 6 pages.

Drake et al., "Influence of magnetic field alignment and defect concentration on nitrogen-vacancy polarization in diamond," New Journal of Physics 18(013011): 1-8 (Jan. 2016; first published on Dec. 24, 2015), 9 pages.

Dreau et al., "Avoiding power broadening in optically detected magnetic resonance of single NV defects for enhanced dc magnetic field sensitivity," Physical Review B 84(195204): 1-8 (Nov. 23, 2011), 8 pages.

Dreau et al., "High-resolution spectroscopy of single NV defects coupled with nearby 13C nuclear spins in diamond," Physical Review B 85(134107): 1-7 (Apr. 20, 2012), 7 pages.

Dumeige et al., "Magnetometry with nitrogen-vacancy ensembles in diamond based on infrared absorption in a doubly resonant optical cavity," Physical Review B 87(155202): 1-9 (Apr. 8, 2013), 9 pages.

Epstein et al., "Anisotropic interactions of a single spin and dark-spin spectroscopy in diamond," Nature Physics 1: 94-98 (Nov. 2005), 5 pages.

Fallah et al., "Multi-sensor approach in vessel magnetic wake imaging," Wave Motion 51(1): 60-76 (Jan. 2014), retrieved from http://www.sciencedirect.com/science/article/pii/S0165212513001133 (Aug. 21, 2016).

Fedotov et al., "High-resolution magnetic field imaging with a nitrogen-vacancy diamond sensor integrated with a photonic-crystal fiber," Optics Letters 41(3): 472-475 (Feb. 1, 2016; published Jan. 25, 2016), 4 pages.

Fedotov et al., "Photonic-crystal-fiber-coupled photoluminescence interrogation of nitrogen vacancies in diamond nanoparticles," Laser Physics Letters 9(2): 151-154 (Feb. 2012; first published online Dec. 2, 2011), 5 pages.

Feng & Wei, "A steady-state spectral method to fit microwave absorptions of NV centers in diamonds: application to sensitive magnetic field sensing," Measurement Science & Technology 25(105102): 1-6 (Oct. 2014; first published online Aug. 29, 2014), 7 pages.

Fologea, et al. "Detecting single stranded DNA with a solid state nanopore." Nano Letters 5.10 (Aug. 15, 2005): 1905-1909.

Freitas, et al., "Solid-State Nuclear Magnetic Resonance (NMR) Methods Applied to the Study of Carbon Materials," Chemistry and Physics of Carbon, vol. 31 (2012), 45 pages.

Gaebel, et al. "Room-temperature coherent coupling of single spins in diamond." Nature Physics 2.6 (May 28, 2006): 408-413.

GB Examination Report from United Kingdom application No. GB 1617438.5 dated Oct. 28, 2016.

GB Examination Report from United Kingdom application No. GB 1618202.4 dated Jan. 10, 2017.

Geiselmann et al., "Fast optical modulation of the fluorescence from a single nitrogen-vacancy centre," Nature Physics 9: 785-789 (Dec. 2013; first published online Oct. 13, 2013), 5 pages.

Gombert & Blasi, "The Moth-Eye Effect-From Fundamentals to Commercial Exploitation," Functional Properties of Bio-Inspired Surfaces: 79-102, (Nov. 2009), 26 pages.

Gong et al., "Generation of Nitrogen-Vacancy Center Pairs in Bulk Diamond by Molecular Nitrogen Implantation," Chinese Physics Letters 33(2)(026105): 1-4 (Feb. 2016), 5 pages.

Gould et al., "An imaging magnetometer for bio-sensing based on nitrogen-vacancy centers in diamond," SPIE 8933, Frontiers in Biological Detection: From Nanosensors to Systems VI, 89330L (Mar. 18, 2014), 8 pages.

Gould et al., "Room-temperature detection of a single 19 nm superparamagnetic nanoparticle with an imaging magnetometer," Applied Physics Letters 105(072406): 1-4 (Aug. 19, 2014), 5 pages.

Gruber et al., "Scanning confocal optical microscopy and magnetic resonance on single defect centers," Science 276(5321): 2012-2014 (Jun. 27, 1997), 4 pages.

Haeberle et al., "Nanoscale nuclear magnetic imaging with chemical contrast," Nature Nanotechnology 10: 125-128 (Feb. 2015; first published online Jan. 5, 2015), 4 pages.

Haihua et al., "Design of wideband anti-reflective sub wavelength nanostructures," Infrared and Laser Engineering 40(2): 267-270 (Feb. 2011), 4 pages.

Hall et al., "Sensing of Fluctuating Nanoscale Magnetic Fields Using Nitrogen-Vacancy Centers in Diamond," Physical Review Letters 103(220802): 1-4 (Nov. 25, 2009), 4 pages.

Hanson et al., "Coherent Dynamics of a Single Spin Interacting with an Adjustable Spin Bath," Science 320(5874): 352-355 (Apr. 18, 2008), 5 pages.

Hanson et al., "Polarization and Readout of Coupled Single Spins in Diamond," Physical Review Letters 97(087601): 1-4 (Aug. 23, 2006), 4 pages.

Hanson et al., "Room-temperature manipulation and decoherence of a single spin in diamond," Physical Review 74(161203): 1-4 (Oct. 26, 2006), 4 pages.

Hanzawa et al., "Zeeman effect on the zero-phonon line of the NV center in synthetic diamond," Physica B 184(1-4): 137-140 (Feb. 1993), 4 pages.

Heerema, et al. "Graphene nanodevices for DNA sequencing." Nature nanotechnology 11.2 (Feb. 3, 2016): 127-136.

Hegyi & Yablonovitch, "Molecular imaging by optically detected electron spin resonance of nitrogen-vacancies in nanodiamonds," Nano Letters 13(3): 1173-1178 (Mar. 2013; first published online Feb. 6, 2013), 6 pages.

Hegyi & Yablonovitch, "Nanodiamond molecular imaging with enhanced contrast and expanded field of view," Journal of Biomedical Optics 19(1)(011015): 1-8 (Jan. 2014), 9 pages.

Hilser et al., "All-optical control of the spin state in the NV-center in diamond," Physical Review B 86(125204): 1-8 (Sep. 14, 2012), 8 pages.

Hobbs, "Study of the Environmental and Optical Durability of AR Microstructures in Sapphire, ALON, and Diamond," SPIE 7302, Window and Dome Technologies and Materials XI, 73020J (Apr. 27, 2009), 14 pages.

Huebener et al., "ODMR of NV centers in nano-diamonds covered with N@C60," Physica Status Solidi B 245(10): 2013-2017 (Oct. 2008; first published online Sep. 8, 2008), 5 pages.

Huxter et al., "Vibrational and electronic dynamics of nitrogen-vacancy centres in diamond revealed by two-dimensional ultrafast spectroscopy," Nature Physics 9: 744-749 (Sep. 29, 2013), 6 pages.

International Search Report and Written Opinion of the International Searching Authority dated Apr. 1, 2016 from related PCT application PCT/US2016/014384, 12 pages.

International Search Report and Written Opinion of the International Searching Authority dated Apr. 11, 2016 from related PCT application PCT/US2016/014376, 12 pages.

International Search Report and Written Opinion of the International Searching Authority dated Apr. 11, 2016 from related PCT application PCT/US2016/014388, 14 pages.

International Search Report and Written Opinion of the International Searching Authority dated Apr. 11, 2016 from related PCT application PCT/US2016/014395, 15 pages.

International Search Report and Written Opinion of the International Searching Authority dated Apr. 4, 2017 from related PCT application PCT/US16/68366, 9 pages.

International Search Report and Written Opinion of the International Searching Authority dated Feb. 15, 2017 from related PCT application PCT/US2016/014390, 20 pages.

(56) References Cited

OTHER PUBLICATIONS

International Search Report and Written opinion of the International Searching Authority dated Jul. 12, 2016, from related PCT application PCT/US2016/014287, 14 pages.
International Search Report and Written Opinion of the International Searching Authority dated Jul. 16, 2015, from related PCT application PCT/US2015/24723, 8 pages.
International Search Report and Written Opinion of the International Searching Authority dated Jul. 6, 2015, from related PCT application PCT/US2015/021093, 9 pages.
International Search Report and Written Opinion of the International Searching Authority dated Jul. 8, 2015, from related PCT application PCT/US2015/024265, 11 pages.
International Search Report and Written Opinion of the International Searching Authority dated Jun. 1, 2017, from related PCT application PCT/US17/21811, 9 pages.
International Search Report and Written Opinion of the International Searching Authority dated Jun. 1, 2017, in related PCT application PCT/US17/22279, 20 pages.
International Search Report and Written Opinion of the International Searching Authority dated Jun. 10, 2016 from related PCT application PCT/US2016/014290, 11 pages.
International Search Report and Written Opinion of the International Searching Authority dated Jun. 15, 2017, from related PCT application PCT/US2017/024175, 10 pages.
International Search Report and Written Opinion of the International Searching Authority dated Jun. 2, 2016, from related PCT application PCT/US2016/014386, 14 pages.
International Search Report and Written Opinion of the International Searching Authority dated Jun. 2, 2016, from related PCT application PCT/US2016/014387, 13 pages.
International Search Report and Written Opinion of the International Searching Authority dated Jun. 6, 2016, from related PCT application PCT/US2016/014291, 13 pages.
International Search Report and Written Opinion of the International Searching Authority dated Jun. 9, 2016 from related PCT application PCT/US2016/014333, 16 pages.
International Search Report and Written Opinion of the International Searching Authority dated Jun. 9, 2017, from related patent application PCT/US2017/024181, 13 pages.
International Search Report and Written Opinion of the International Searching Authority dated Jun. 9, 2017, from related PCT application PCT/US2017/024179, 9 pages.
International Search Report and Written Opinion of the International Searching Authority dated Mar. 13, 2017 from related PCT application PCT/US2016/68320, 10 pages.
International Search Report and Written Opinion of the International Searching Authority dated Mar. 24, 2016 from related PCT application PCT/US2016/014336, 17 pages.
International Search Report and Written Opinion of the International Searching Authority dated Mar. 24, 2016 from related PCT application PCT/US2016/014297, 15 pages.
International Search Report and Written Opinion of the International Searching Authority dated Mar. 24, 2016 from related PCT application PCT/US2016/014392, 8 pages.
International Search Report and Written Opinion of the International Searching Authority dated Mar. 24, 2016 from related PCT application PCT/US2016/014403, 10 pages.
International Search Report and Written Opinion of the International Searching Authority dated Mar. 25, 2016, from related PCT application PCT/US2016/014363, 8 pages.
International Search Report and Written Opinion of the International Searching Authority dated Mar. 25, 2016, from related PCT application PCT/US2016/014389, 19 pages.
International Search Report and Written Opinion of the International Searching Authority dated Mar. 27, 2017 from related PCT application PCT/US16/68344, 16 pages.
International Search Report and Written Opinion of the International Searching Authority dated Mar. 28, 2016, from related PCT application PCT/US2016/014380, 9 pages.
International Search Report and Written Opinion of the International Searching Authority dated Mar. 28, 2016, from related PCT application PCT/US2016/014394, 17 pages.
International Search Report and Written Opinion of the International Searching Authority dated Mar. 29, 2016 from related PCT application PCT/US2016/014325, 11 pages.
International Search Report and Written Opinion of the International Searching Authority dated Mar. 29, 2016 from related PCT application PCT/US2016/014330, 8 pages.
International Search Report and Written Opinion of the International Searching Authority dated Mar. 29, 2016, from related PCT application PCT/US2016/014328, 7 pages.
International Search Report and Written Opinion of the International Searching Authority dated Mar. 29, 2016, from related PCT application PCT/US2016/014385, 11 pages.
International Search Report and Written Opinion of the International Searching Authority dated Mar. 30, 2016 from related PCT application PCT/US2016/014298, 14 pages.
International Search Report and Written Opinion of the International Searching Authority dated Mar. 31, 2016 from related PCT application PCT/US2016/014375, 11 pages.
International Search Report and Written Opinion of the International Searching Authority dated Mar. 31, 2016 from related PCT application PCT/US2016/014396, 11 pages.
International Search Report and Written Opinion of the International Searching Authority dated Mar. 31, 2017 from related PCT application PCT/US2016/066566, 11 pages.
International Search Report and Written Opinion of the International Searching Authority dated May 10, 2017 from related PCT application PCT/US17/19411, 8 pages.
International Search Report and Written Opinion of the International Searching Authority dated May 18, 2017, from related PCT application PCT/US2017/021593, 10 pages.
International Search Report and Written Opinion of the International Searching Authority dated May 19, 2017, from related PCT application PCT/US17/18099, 16 pages.
International Search Report and Written Opinion of the International Searching Authority dated May 26, 2016, from related PCT application PCT/US2016/014331, 15 pages.
International Search Report and Written Opinion of the International Searching Authority dated May 3, 2017 from related PCT application PCT/US2017/018701, 8 pages.
International Search Report and Written Opinion of the International Searching Authority dated May 4, 2017 from related PCT application PCT/US2017/018709, 8 pages.
International Search Report and Written Opinion of the International Searching Authority dated May 8, 2017 from related PCT application PCT/US2017/17321, 17 pages.
International Search Report and Written Opinion of the International Searching Authority dated Sep. 13, 2016, from related PCT application PCT/US16/14377, 11 pages.
International Search Report and Written Opinion of the International Searching Authority dated Jul. 14, 2017, from related PCT application PCT/US2017/022118, 13 pages.
International Search Report and Written Opinion of the International Searching Authority dated Jul. 17, 2017, from related PCT application PCT/US2017/024177, 11 pages.
International Search Report and Written Opinion of the International Searching Authority dated Jul. 18, 2017, from related PCT application PCT/US2017/024167, 11 pages.
International Search Report and Written Opinion of the International Searching Authority dated Jul. 18, 2017, from related PCT application PCT/US2017/024173, 13 pages.
International Search Report and Written Opinion of the International Searching Authority dated Jul. 19, 2017, from related PCT application PCT/US2017/024171, 12 pages.
International Search Report and Written Opinion of the International Searching Authority dated Jun. 15, 2017, from related PCT application PCT/US2017/024182, 21 pages.
International Search Report and Written Opinion of the International Searching Authority dated Jun. 22, 2017, in related PCT application PCT/US2017/024180, 10 pages.

(56) References Cited

OTHER PUBLICATIONS

International Search Report and Written Opinion of the International Searching Authority dated Jun. 5, 2017, from related PCT application PCT/US2017/024169 (11 pages).
International Search Report and Written Opinion of the International Searching Authority dated Jun. 5, 2017, from related PCT application PCT/US2017/024174, 8 pages.
International Search Report and Written Opinion of the International Searching Authority dated Jun. 5, 2017, in related PCT application PCT/US2017/024168 (7 pages).
International Search Report and Written Opinion of the International Searching Authority dated Jun. 6, 2017, from related PCT application PCT/US2017/024172 (9 pages).
International Search Report and Written Opinion of the International Searching Authority dated Jun. 6, 2017, from related PCT application US/2017/024165 (9 pages).
Ivady et al., "Pressure and temperature dependence of the zero-field splitting in the ground state of NV centers in diamond: A first-principles study," Physical Review B 90(235205): 1-8 (Dec. 2014), 8 pages.
Jarmola et al., "Temperature- and Magnetic-Field-Dependent Longitudinal Spin Relaxation in Nitrogen-Vacancy Ensembles in Diamond," Physical Review Letters 108 (197601): 1-5 (May 2012), 5 pages.
Jensen et al., "Light narrowing of magnetic resonances in ensembles of nitrogen-vacancy centers in diamond," Physical Review B 87(014115): 1-10 (Jan. 2013), 10 pages.
Kailath, "Linear Systems," Prentice Hall, (1979), 6 pages.
Karlsson et al., "Diamond micro-optics: microlenses and antireflection structures surfaces for the infrared spectral region," Optics Express 11(5): 502-507 (Mar. 10, 2003), 6 pages.
Keyser "Enhancing nanopore sensing with DNA nanotechnology." Nature nanotechnology 11.2 (Feb. 2016): 106-108.
Khan & Hemmer, "Noise limitation in nano-scale imaging," Proceedings of SPIE vol. 5842: 302-305, (Dec. 2005), 7 pages.
Kim et al., "Electron spin resonance shift and linewidth broadening of nitrogen-vacancy centers in diamond as a function of electron irradiation dose," Applied Physics Letters 101(082410): 1-5 (Aug. 2012), 6 pages.
Kim et al., "Jahn-Teller Splitting and Zeeman Effect of Acceptors in Diamond," Physica B 273-274: 647-627 (Jul. 1999), 4 pages.
Kim et al., "Magnetospectroscopy of acceptors in 'blue' diamonds," Physica B 302-301: 88-100 (Aug. 2001), 13 pages.
Kim et al., "Zeeman effect of electronic Raman lines of accepters in elemental semiconductors: Boron in blue diamond," Physical Review B 62(12): 8038-8052 (Sep. 2000), 15 pages.
King et al., "Optical polarization of 13C nuclei in diamond through nitrogen vacancy centers," Physical Review B 81(073201): 1-4 (Feb. 2010), 4 pages.
Kok et al., "Materials Science: Qubits in the pink," Nature 444(2): 49 (Nov. 2006), 1 page.
Konenko et al., "Formation of antireflective surface structures on diamond films by laser patterning," Applied Physics a 68:99-102 (Jan. 1999), 4 pages.
Kraus et al., "Magnetic field and temperature sensing with atomic-scale spin defects in silicon carbide," Scientific Reports 4(5303): 1-8 (Jul. 2014), 8 pages.
Lai et al., "Influence of a static magnetic field on the photoluminescence of an ensemble of nitrogen—vacancy color centers in a diamond single-crystal," Applied Physics Letters 95, (Sep. 2009), 4 pages.
Lai et al., "Optically detected magnetic resonance of a single Nitrogen-Vacancy electronic spin in diamond nanocrystals," CLEO/EQEC, (Jun. 14-19, 2009), 1 page.
Laraoui et al., "Nitrogen-vacancy assisted magnetometry of paramagnetic centers in an individual diamond nanocrystal," Nano Letters 12: 3477-3482 (Jul. 2012), 6 pages.
Lazariev et al., "A nitrogen-vacancy spin based molecular structure microscope using multiplexed projection reconstruction," Scientific Reports 5(14130): 1-8 (Sep. 2015), 8 pages.
Le Sage et al., "Efficient photon detection from color centers in a diamond optical waveguide," Phys. Rev. B 85: 121202(R), pp. 121202-1-121202-4, (Mar. 23, 2012), 4 pages.
Lee et al., "Vector magnetometry based on S=3/2 electronic spins," Physical Review B 92 (115201): 1-7 (Sep. 2015), 7 pages.
Lesik et al., "Preferential orientation of NV defects in CVD diamond films grown on (113)-oriented substrates," Diamond and Related Materials 56: 47-53 (Jun. 2015), 7 pages.
Levchenko et al., "Inhomogeneous broadening of optically detected magnetic resonance of the ensembles of nitrogen-vacancy centers in diamond by interstitial carbon atoms," Applied Physics Letters 106, (Mar. 2015; published online Mar. 9, 2015), 6 pages.
Lindsay "The promises and challenges of solid-state sequencing." Nature nanotechnology 11.2 (Feb. 2016): 109-111.
Liu et al., "Electron spin studies of nitrogen vacancy centers in nanodiamonds," Acta Physica Sinica 62(16) 164208: 1-5 (Aug. 2013), 5 pages.
Liu et al., "Fiber-integrated diamond-based magnetometer," Applied Physics Letters 103(143105): 1-4 (Sep. 2013), 5 pages.
MacLaurin et al., "Nanoscale magnetometry through quantum control of nitrogen-vacancy centres in rotationally diffusing nanodiamonds," New Journal of Physics 15, (Jan. 2013), 16 pages.
MacQuarie et al., "Mechanical spin control of nitrogen-vacancy centers in diamond," Retrieved from http://www.arxiv.org/pdf/1306.6356.pdf, pp. 1-8, (Jun. 2013), 8 pages.
Macs et al., "Diamond as a magnetic field calibration probe," Journal of Physics D: Applied Physics 37, (Apr. 2004; published Mar. 17, 2004), 6 pages.
Maletinsky et al., "A robust scanning diamond sensor for nanoscale imaging with single nitrogen-vacancy centres," Nature Nanotechnology 7: 320-324, (May 2012; published Apr. 15, 2012), 5 pages.
Mamin et al., "Multipulse Double-Quantum Magnetometry with Near-Surface Nitrogen-Vacancy Centers," Physical Review Letters 13(030803): 1-5 (Jul. 2014), 5 pages.
Mamin et al., "Nanoscale Nuclear Magnetic Resonance with a Nitrogen-Vacancy Spin Sensor," Science 339, (Feb. 2013), 5 pages.
Manson et al., "GR transitions in diamond: magnetic field measurements," Journal of Physics C Solid St. Phys 13: L1005-L1009, (Nov. 1980), 6 pages.
Massachusetts Institute of Technology, "Wide-Field Imaging Using Nitrogen Vacancies," in Patent Application Approval Process, Physics Week: 1-5, (Jan. 20, 2015), 5 pages.
Matlashov, et al. "SQUIDs for magnetic resonance imaging at ultra-low magnetic field." PIERS online 5.5 (2009): 466-470.
Matlashov, et al. "SQUIDs vs. induction coils for ultra-low field nuclear magnetic resonance: experimental and simulation comparison." IEEE Transactions on Applied Superconductivity 21.3 (Jan. 1, 2012): 465-468.
Matsuda et al., "Development of a plastic diamond anvil cell for high pressure magneto-photoluminescence in pulsed high magnetic fields," International Journal of Modern Physics B 18(27-29), (Nov. 2004), 7 pages.
Maze et al., "Nanoscale magnetic sensing using spin qubits in diamond," Proc. SPIE 7225, Advanced Optical Concepts in Quantum Computing, Memory, and Communication II, 722509 (Feb. 2, 2009) 8 pages.
Maze et al., "Nanoscale magnetic sensing with an individual electronic spin in diamond," Nature Physics 455: 644-647 (Oct. 2, 2008), 5 pages.
Meijer et al., "Generation of single color centers by focused nitrogen implantation," Applied Physics Letters 87(261909): 1-3 (Dec. 2005), 4 pages.
Michaelovich et al., "Polarization Dependencies of the Nitrogen-Vacancy Center." Undergraduate Project Report, Ben-Gurion University, Aug. 2015, pp. 1-9.
Millot et al., "High-field Zeeman and Paschen-Back effects at high pressure in oriented ruby," Physical Review B 78 (155125): 1-7 (Oct. 2008), 7 pages.
Moessle, et al. "SQUID-detected magnetic resonance imaging in microtesla fields." Annu. Rev. Biomed. Eng. 9 (May 23, 2008): 389-413.

(56) References Cited

OTHER PUBLICATIONS

Moriyama et al., "Importance of electron-electron interactions and Zeeman splitting in single-wall carbon nanotube quantum dots," Physica E 26: 473-476 (Feb. 2005), 4 pages.

Mrozek et al., "Circularly polarized microwaves for magnetic resonance study in the GHz range: Application to nitrogen-vacancy in diamonds," Applied Physics Letters, pp. 1-4 (Jul. 2015), 4 pages.

Nagl et al., "Improving surface and defect center chemistry of fluorescent nanodiamonds for imaging purposes—a review," Analytical and Bioanalaytical Chemistry 407: 7521-7536 (Oct. 2015; published online Jul. 29, 2015), 16 pages.

Neumann et al., "Excited-state spectroscopy of single NV defects in diamond using optically detected magnetic resonance," New Journal of Physics 11(013017): 1-10, (Jan. 2009), 11 pages.

Nizovtsev & Kilin, "Optically Detected Magnetic Resonance Spectra of the 14NV—13C Spin Systems in Diamond: Analytical Theory and Experiment," Doklady of the National Academy of Sciences of Belarus, (2013), 27 pages with English machine translation.

Nizovtsev et al., "Modeling fluorescence of single nitrogen-vacancy defect centers in diamond," Physica B—Condensed Matter, 608-611 (Dec. 2001), 4 pages.

Nizovtsev et al., "Theoretical study of hyperfine interactions and optically detected magnetic resonance spectra by simulation of the C—291(NV)H-(172) diamond cluster hosting nitrogen-vacancy center," New Journal of Physics 16(083014): 1-21 (Aug. 2014), 22 pages.

Nobauer et al., "Smooth optimal quantum control for robust solid state spin magnetometry," Retrieved from http://www.arxiv.org/abs/1412.5051, pp. 1-12, (Dec. 2014), 12 pages.

Notice of Allowance dated Jun. 8, 2017, from related U.S. Appl. No. 15/351,862, 7 pages.

Nowodzinski et al., "Nitrogen-Vacancy centers in diamond for current imaging at the redistributive layer level of Integrated Circuits," Microelectronics Reliability 55: 1549-1553 (Aug. 2015), 5 pages.

Nusran et al., "Optimizing phase-estimation algorithms for diamond spin magnetometry," Physical Review B 90(024422): 1-12 (Jul. 2014), 12 pages.

Ohashi et al., "Negatively Charged Nitrogen-Vacancy Centers in a 5 nm Thin 12C Diamond Film," Nano Letters 13: 4733-4738 (Oct. 2013), 6 pages.

Pelliccione, et al., Two-dimensional nanoscale imaging of gadolinium spins via scanning probe relaxometry with a single spin in diamond, Phys. Rev. Applied 2.5, (Sep. 8, 2014): 054014 pp. 1-17.

Plakhotnik et al., "Super-Paramagnetic Particles Chemically Bound to Luminescent Diamond : Single Nanocrystals Probed with Optically Detected Magnetic Resonance," Journal of Physical Chemistry C 119: 20119-20124 (Aug. 2015), 6 pages.

Polatomic. "AN/ASQ-233A Digital Magnetic Anomaly Detective Set." Retrieved May 9, 2016, from http://polatomic.com/images/DMAD_Data_Sheet_09-2009.pdf (2009), 1 page.

Poole, "What is GMSK Modulation—Gaussian Minimum Shift Keying." Radio-Electronics, retrieved from https://web.archive.org/web/20150403045840/http://www.radio-electronics.com/info/rf-technology-design/pm-phase-modulation/what-is-gmsk-gaussian-minimum-shift-keyingtutorial.php (Apr. 3, 2015), 4 pages.

Qiu et al., "Low-field NMR Measurement Procedure when SQUID Detection is Used," IEEE/CSC & ESAS European Superconductivity News Forum, No. 5, Jul. 2008.

Qiu, et al. "SQUID-detected NMR in Earth's magnetic field." Journal of Physics: Conference Series. vol. 97. No. 1 IOP Publishing, Mar. 2008, pp. 1-7.

Rabeau et al., "Implantation of labelled single nitrogen vacancy centers in diamond using 15N," Applied Physics Letters 88, (Jan. 2006), 4 pages.

Ranjbar et al., "Many-electron states of nitrogen-vacancy centers in diamond and spin density calculations," Physical Review B 84(165212): 1-6 (Oct. 2011), 6 pages.

Reynhardt, "Spin-lattice relaxation of spin-1/2 nuclei in solids containing diluted paramagnetic impurity centers. I. Zeeman polarization of nuclear spin system," Concepts in Magnetic Resonance Part A, pp. 20-35, (Sep. 2003), 16 pages.

Rogers et al., "Singlet levels of the NV(-) centre in diamond," New Journal of Physics 17, (Jan. 2015), 13 pages.

Rondin et al., "Magnetometry with nitrogen-vacancy defects in diamond," Reports on Progress in Physics 77(056503) 1-26 (May 2014), 27 pages.

Rondin et al., "Magnetometry with nitrogen-vacancy defects in diamond." May 22, 2014 (May 22, 2014), pp. 1 [online] http://arxiv.org/pdf/1311.5214.pdf, 29 pages.

Rondin et al., "Nanoscale magnetic field mapping with a single spin scanning probe magnetometer," Applied Physics Letters 100, (Apr. 2012), 5 pages.

Sarkar et al., "Magnetic properties of graphite oxide and reduced graphene oxide," Physica E 64: 78-82 (Nov. 2014), 5 pages.

Scheuer et al., "Accelerated 2D magnetic resonance spectroscopy of single spins using matrix completion," Scientific Reports 5(17728): 1-8 (Dec. 2015), 8 pages.

Schirhagl et al., "Nitrogen-vacancy centers in diamond: Nanoscale sensors for physics and biology," Annual Review of Physical Chemistry 65: 83-105 (Jan. 2014), 26 pages.

Schoenfeld & Harneit, "Real time magnetic field sensing and imaging using a single spin in diamond," Physical Review Letters 106(030802): 1-4 (Jan. 2011), 4 pages.

Sedov et al., "Si-doped nano- and microcrystalline diamond films with controlled bright photoluminescence of silicon-vacancy color centers," Diamond and Related Materials 56: 23-28 (Jun. 2015; available online Apr. 18, 2015), 6 pages.

Shames et al., "Magnetic resonance tracking of fluorescent nanodiamond fabrication," Journal of Physics D: Applied Physics 48(155302): 1-13 (Apr. 2015; published Mar. 20, 2015), 14 pages.

Shao et al., "Diamond Color Center Based FM Microwave Demodulator," in Conference on Lasers and Electro-Optics, OSA Technical Digest (online) (Optical Society of America), paper JTh2A.136, (Jun. 5-10, 2016), 2 pages.

Sheinker et al., "Localization in 3-D Using Beacons of Low Frequency Magnetic Field." IEEE Transactions on Instrumentation and Measurement 62(12): 3194-3201 (Dec. 2013), 8 pages.

Simanovskaia et al., "Sidebands in optically detected magnetic resonance signals of nitrogen vacancy centers in diamond," Physical Review B 87(224106): 1-11 (Jun. 2013), 11 pages.

Sotoma et al., "Effective production of fluorescent nanodiamonds containing negatively-charged nitrogen-vacancy centers by ion irradiation," Diamond and Related Materials 49: 33-38 (Oct. 2014), 6 pages.

Soykal et al., "Quantum metrology with a single spin-3/2 defect in silicon carbide," Mesoscale and Nanoscale Physics (May 24, 2016), retrieved from https://arxiv.org/abs/1605.07628 (Sep. 22, 2016), 9 pages.

Steiner et al., "Universal enhancement of the optical readout fidelity of single electron spins at nitrogen-vacancy centers in diamond," Physical Review B 81(035205): 1-6 (Jan. 2010), 6 pages.

Steinert et al., "High-sensitivity magnetic imaging using an array of spins in diamond," Rev. Sci. Inst. 81(043705): 1-5 (Apr. 23, 2010), 5 pages.

Steinert et al., "Magnetic spin imaging under ambient conditions with sub-cellular resolution." Nature Comms 4:1607 (Mar. 19, 2013).

Stepanov et al., "High-frequency and high-field optically detected magnetic resonance of nitrogen-vacancy centers in diamond," Applied Physics Letters 106, (Feb. 2015), 5 pages.

Sternschulte et al., "Uniaxial stress and Zeeman splitting of the 1.681 eV optical center in a homoepitaxial CVD diamond film," Diamond and Related Materials 4: 1189-1192 (Sep. 1995), 4 pages.

Storteboom et al., "Lifetime investigation of single nitrogen vacancy centres in nanodiamonds," Optics Express 23(9): 11327-11333 (May 4, 2015; published Apr. 22, 2015), 7 pages.

Sushkov, et al. "All-optical sensing of a single-molecule electron spin." Nano letters 14.11 (Nov. 7, 2013): 6443-6448.

Tahara et al., "Quantifying selective alignment of ensemble nitrogen-vacancy centers in (111) diamond," Applied Physics Letters 107:193110 (Nov. 2015; published online Nov. 13, 2015), 5 pages.

(56) References Cited

OTHER PUBLICATIONS

Taylor et al., "High-sensitivity diamond magnetometer with nanoscale resolution," Nature Physics 4: 810-816 (Oct. 2008), 7 pages.
Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
Terblanche et al., "13C spin-lattice relaxation in natural diamond: Zeeman relaxation at 4.7 T and 300 K due to fixed paramagnetic nitrogen defects," Solid State Nuclear Magnetic Resonance 20: 1-22 (Aug. 2001), 22 pages.
Terblanche et al., "13C spin-lattice relaxation in natural diamond: Zeeman relaxation in fields of 500 to 5000 G at 300 K due to fixed paramagnetic nitrogen defects," Solid State Nuclear Magnetic Resonance 19: 107-129 (May 2001), 23 pages.
Tetienne et al., "Magnetic-field-dependent photodynamics of single NV defects in diamond: an application to qualitative all-optical magnetic imaging," New Journal of Physics 14(103033): 1-5 (Oct. 2012), 16 pages.
Tetienne, et al. "Spin relaxometry of single nitrogen-vacancy defects in diamond nanocrystals for magnetic noise sensing." Physical Review B 87.23 (Apr. 3, 2013): 235436-1-235436-5.
Tong et al., "A hybrid-system approach for W state and cluster state generation," Optics Communication 310: 166-172, (Jan. 2014; available online Aug. 12, 2013), 7 pages.
Uhlen et al., "New diamond nanofabrication process for hard x-ray zone plates," J. of Vacuum Science & Tech. B 29(6) (06FG03): 1-4 (Nov./Dec. 2011), 4 pages.
U.S. Notice of Allowance dated Apr. 20, 2016, from related U.S. Appl. No. 15/003,718, 9 pages.
U.S. Notice of Allowance dated Aug. 17, 2016, from related U.S. Appl. No. 15/003,718, 8 pages.
U.S. Notice of Allowance dated Dec. 13, 2016, from related U.S. Appl. 14/680,877, 8 pages.
U.S. Notice of Allowance dated Dec. 13, 2016, from related U.S. Appl. No. 14/680,877, 8 pages.
U.S. Notice of Allowance dated Dec. 22, 2016, from related U.S. Appl. No. 14/659,498, 10 pages.
U.S. Notice of Allowance dated Feb. 14, 2017, from related U.S. Appl. No. 15/003,677, 8 pages.
U.S. Notice of Allowance dated Jul. 18, 2017 from related U.S. Appl. No. 15/003,634, 6 pages.
U.S. Notice of Allowance dated Jul. 19, 2016, from related U.S. Appl. No. 15/003,590, 9 pages.
U.S. Notice of Allowance dated Jul. 24, 2017, from related U.S. Appl. No. 15/003,088, 12 pages.
U.S. Notice of Allowance dated Jun. 20, 2017, from related U.S. Appl. No. 15/204,675, 9 pages.
U.S. Notice of Allowance dated Jun. 28, 2017 from related U.S. Appl. No. 15/003,256, 10 pages.
U.S. Notice of Allowance dated Mar. 15, 2017, from related U.S. Appl. No. 15/351,862, 6 pages.
U.S. Notice of Allowance dated Mar. 29, 2016, from related U.S. Appl. No. 15/003,590, 11 pages.
U.S. Notice of Allowance dated May 26, 2017 from related U.S. Appl. No. 15/218,821, 7 pages.
U.S. Notice of Allowance dated Sep. 8, 2016, from related U.S. Appl. No. 15/003,298, 10 pages.
U.S. Office Action dated Apr. 17, 2017, from related U.S. Appl. No. 15/003,558, 12 pages.
U.S. Office Action dated Aug. 24, 2016 from related U.S. Appl. No. 14/676,740, 19 pages.
U.S. Office Action dated Feb. 10, 2017, from related U.S. Appl. No. 14/676,740, 20 pages.
U.S. Office Action dated Feb. 10, 2017, from related U.S. Appl. No. 15/003,088, 11 pages.
U.S. Office Action dated Feb. 16, 2017, from related U.S. Appl. No. 15/204,675, 7 pages.
U.S. Office Action dated Jul. 27, 2017 from related U.S. Appl. No. 15/003,577, 15 pages.
U.S. Office Action dated Jul. 29, 2016 from related U.S. Appl. No. 14/680,877, 8 pages.
U.S. Office Action dated Jun. 1, 2017, from related U.S. Appl. No. 15/003,797, 29 pages.
U.S. Office Action dated Jun. 1, 2017, from related U.S. Appl. No. 15/179,957, 29 pages.
U.S. Office Action dated Jun. 12, 2017, from related U.S. Appl. No. 15/003,256, 9 pages.
U.S. Office Action dated Jun. 12, 2017, from related U.S. Appl. No. 15/003,336, 14 pages.
U.S. Office Action dated Jun. 16, 2017, from related U.S. Appl. No. 15/003,678, 15 pages.
U.S. Office Action dated Jun. 2, 2017, from related U.S. Appl. No. 15/476,636, 10 pages.
U.S. Office Action dated Mar. 1, 2017, from related U.S. Appl. No. 15/003,634, 7 pages.
U.S. Office Action dated Mar. 16, 2017, from related U.S. Appl. No. 15/218,821, 7 pages.
U.S. Office Action dated May 13, 2016, from related U.S. Appl. No. 14/676,740, 15 pages.
U.S. Office Action dated May 22, 2017, from related U.S. Appl. No. 15/003,206, 12 pages.
U.S. Office Action dated May 6, 2016, from related U.S. Appl. No. 14/659,498.
U.S. Office Action dated Nov. 2, 2016, from related U.S. Appl. No. 15/003,256, 19 pages.
U.S. Office Action dated Nov. 3, 2016, from related U.S. Appl. No. 15/204,675, 9 pages.
U.S. Office Action dated Oct. 14, 2016 from related U.S. Appl. No. 15/003,677, 13 pages.
U.S. Office Action dated Oct. 19, 2016, from related U.S. Appl. No. 15/218,821, 6 pages.
Vershovskii & Dmitriev, "Combined excitation of an optically detected magnetic resonance in nitrogen-vacancy centers in diamond for precision measurement of the components of a magnetic field vector," Technical Physics Letters 41(11): 1026-1029 (Nov. 2015), 4 pages.
Vershovskii & Dmitriev, "Micro-scale three-component quantum magnetometer based on nitrogen-vacancy color centers in diamond crystal," Technical Physics Letters 41(4): 393-396 (Apr. 2015), 4 pages.
Wahlstrom et al., "Modeling Magnetic Fields Using Gaussian Processes," 2013 IEEE International Conference on Acoustics, Speech, and Signal Processing, pp. 3522-3526 (May 26-31, 2013), 5 pages.
Wang et al., "Optimizing ultrasensitive single electron magnetometer based on nitrogen-vacancy center in diamond," Chinese Science Bulletin, 58(24): 2920-2923, (Aug. 2013), 4 pages.
Webber et al., "Ab initio thermodynamics calculation of the relative concentration of NV- and NV0 defects in diamond," Physical Review B 85,(014102): 1-7 (Jan. 2012), 7 pages.
Wells, et al. "Assessing graphene nanopores for sequencing DNA." Nano letters 12.8 (Jul. 10, 2012): 4117-4123.
Widmann et al., "Coherent control of single spins in silicon carbide at room temperature," Nature Materials, 14: 164-168 (2015) (available online Dec. 1, 2014), 5 pages.
Wolf et al., "Subpicotesla Diamond Magnetometry," Physical Review X 5(041001): 1-10 (Oct. 2015), 10 pages.
Wolfe et al., "Off-resonant manipulation of spins in diamond via precessing magnetization of a proximal ferromagnet," Physical Review B 89(180406): 1-5 (May 2014), 5 pages.
Wroble, "Performance Analysis of Magnetic Indoor Local Positioning System." Western Michigan University Master's Theses, Paper 609 (Jun. 2015), 42 pages.
Wysocki et al., "Modified Walsh-Hadamard sequences for DS CDMA wireless systems." Int. J. Adaptive Control and Signal Processing 16(8): 589-602 (Oct. 2002; first published online Sep. 23, 2002), 25 pages.
Xue & Liu, "Producing GHZ state of nitrogen-vacancy centers in cavity QED," Journal of Modern Optics 60(6-7), (Mar. 2013), 8 pages.

(56) References Cited

OTHER PUBLICATIONS

Yang & Gu, "Novel calibration techniques for high pulsed-magnetic fields using luminescence caused by photo," (with English machine translation), Journal of Huazhong University of Science and Technology, (Jun. 2007), 11 pages.
Yavkin et al., "Defects in Nanodiamonds: Application of High-Frequency cw and Pulse EPR, ODMR," Applied Magnetic Resonance, 45: 1035-1049 (Oct. 2014; published online Sep. 10, 2014), 15 pages.
Yu et al., "Bright fluorescent nanodiamonds: no photobleaching and low cytotoxicity," J. Am. Chem. Soc., 127: 17604-17605 (Nov. 25, 2005), 2 pages.
Zhang et al., "Laser-polarization-dependent and magnetically controlled optical bistability in diamond nitrogen-vacancy centers," Physics Letters A 377: 2621-2627 (Nov. 2013), 7 pages.
Zhang et al., "Laser-polarization-dependent spontaneous emission of the zero phonon line from single nitrogen-vacancy center in diamond," Chinese Physics B 24(3), (Apr. 2014), 13 pages.
Zhang et al., "Scalable quantum information transfer between nitrogen-vacancy-center ensembles," Annals of Physics, 355: 170-181 (Apr. 2015; available online Feb. 14, 2013), 12 pages.
Zhao et al., "Atomic-scale magnetometry of distant nuclear spin clusters via nitrogen-vacancy spin in diamond," Nature Nanotechnology, 5: 242-246 (Apr. 2011), 5 pages.
U.S. Appl. No. 14/659,498, filed Mar. 16, 2015, U.S. Pat. No. 9,638,821.
PCT/US2015/021093, Mar. 17, 2015, WO2015142945.
U.S. Appl. No. 14/676,740, filed Apr. 1, 2015, 20150326410.
PCT/US2015/024265, Apr. 3, 2015, WO2015157110.
PCT/US2015/024723, Apr. 7, 2015, WO2015157290.
U.S. Appl. No. 14/680,877, filed Apr. 7, 2015, U.S. Pat. No. 9,590,601.
U.S. Appl. No. 14/866,730, filed Sep. 25, 2015, 20160146904.
U.S. Appl. No. 15/003,678, filed Jan. 21, 2016.
U.S. Appl. No. 15/003,281, filed Jan. 21, 2016.
U.S. Appl. No. 15/003,292, filed Jan. 21, 2016.
U.S. Appl. No. 15/003,298, filed Jan. 21, 2016, U.S. Pat. No. 9,551,763.
U.S. Appl. No. 15/003,309, filed Jan. 21, 2016.
U.S. Appl. No. 15/003,176, filed Jan. 21, 2016, 20170123015.
U.S. Appl. No. 15/003,145, filed Jan. 21, 2016.
U.S. Appl. No. 15/003,336, filed Jan. 21, 2016.
U.S. Appl. No. 15/003,558, filed Jan. 21, 2016, 20170146617.
U.S. Appl. No. 15/003,519, filed Jan. 21, 2016, 20170146616.
U.S. Appl. No. 15/003,677, filed Jan. 21, 2016, U.S. Pat. No. 9,614,589.
U.S. Appl. No. 15/003,256, filed Jan. 21, 2016.
U.S. Appl. No. 15/003,577, filed Jan. 21, 2016.
U.S. Appl. No. 15/003,704, filed Jan. 21, 2016, 20160231394.
U.S. Appl. No. 15/003,718, filed Jan. 21, 2016, U.S. Pat. No. 9,541,610.
U.S. Appl. No. 15/003,062, filed Jan. 21, 2016, 20170023487.
U.S. Appl. No. 15/003,652, filed Jan. 21, 2016, 20170010594.
U.S. Appl. No. 15/003,634, filed Jan. 21, 2016.
U.S. Appl. No. 15/003,670, filed Jan. 21, 2016.
U.S. Appl. No. 15/003,088, filed Jan. 21, 2016, 20160214714.
U.S. Appl. No. 15/003,797, filed Jan. 21, 2016, 20160216341.
U.S. Appl. No. 15/003,590, filed Jan. 21, 2016, U.S. Pat. No. 9,557,391.
U.S. Appl. No. 15/003,206, filed Jan. 21, 2016, 20170110015.
U.S. Appl. No. 15/003,193, filed Jan. 21, 2016, 20160216304.
U.S. Appl. No. 15/003,617, filed Jan. 21, 2016, 20170010334.
U.S. Appl. No. 15/003,396, filed Jan. 21, 2016, 20170068012.
U.S. Appl. No. 15/003,177, filed Jan. 21, 2016.
U.S. Appl. No. 15/003,209, filed Jan. 21, 2016.
PCT/US2016/014389, Jan. 21, 2016, WO2017078766.
PCT/US2016/014336, Jan. 21, 2016, WO2016118756.
PCT/US2016/014403, Jan. 21, 2016, WO2016118791.
PCT/US2016/014331, Jan. 21, 2016, WO2016126435.
PCT/US2016/014387, Jan. 21, 2016, WO2017014807.
PCT/US2016/014390, Jan. 21, 2016, WO2016190909.
PCT/US2016/014385, Jan. 21, 2016, WO2016122966.
PCT/US2016/014375, Jan. 21, 2016, WO2016122965.
PCT/US2016/014298, Jan. 21, 2016, WO2017007514.
PCT/US2016/014297, Jan. 21, 2016, WO2017007513.
PCT/US2016/014377, Jan. 21, 2016, WO2017039747.
PCT/US2016/014333, Jan. 21, 2016, WO2016126436.
PCT/US2016/014328, Jan. 21, 2016, WO2017087014.
PCT/US2016/014325, Jan. 21, 2016, WO2017087013.
U.S. Appl. No. 15/179,957, filed Jun. 10, 2016, 20160356863.
U.S. Appl. No. 15/207,457, filed Jul. 11, 2016.
U.S. Appl. No. 15/218,821, filed Jul. 25, 2016.
U.S. Appl. No. 15/204,675, filed Jul. 7, 2016.
U.S. Appl. No. 15/350,303, filed Nov. 14, 2016.
U.S. Appl. No. 15/351,862, filed Nov. 15, 2016.
U.S. Appl. No. 15/372,201, filed Dec. 7, 2016.
U.S. Appl. No. 15/376,244, filed Dec. 12, 2016.
U.S. Appl. No. 15/380,691, filed Dec. 15, 2016.
U.S. Appl. No. 15/382,045, filed Dec. 16, 2016.
U.S. Appl. No. 15/380,419, filed Dec. 15, 2016.
U.S. Appl. No. 15/419,832, filed Jan. 30, 2017, 20170139017.
U.S. Appl. No. 15/400,794, filed Jan. 6, 2017, 20170115361.
U.S. Appl. No. 15/443,422, filed Feb. 27, 2017.
U.S. Appl. No. 15/437,222, filed Feb. 20, 2017, 20170120293.
U.S. Appl. No. 15/437,038, filed Feb. 20, 2017.
U.S. Appl. No. 15/440,194, filed Feb. 23, 2017.
U.S. Appl. No. 15/446,373, filed Mar. 1, 2017.
U.S. Appl. No. 15/450,504, filed Mar. 6, 2017.
U.S. Appl. No. 15/454,162, filed Mar. 9, 2017.
U.S. Appl. No. 15/456,913, filed Mar. 13, 2017.
U.S. Appl. No. 15/468,356, filed Mar. 24, 2017.
U.S. Appl. No. 15/468,397, filed Mar. 24, 2017.
U.S. Appl. No. 15/468,386, filed Mar. 24, 2017.
U.S. Appl. No. 15/468,289, filed Mar. 24, 2017.
U.S. Appl. No. 15/468,641, filed Mar. 24, 2017.
U.S. Appl. No. 15/468,582, filed Mar. 24, 2017.
U.S. Appl. No. 15/468,410, filed Mar. 24, 2017.
U.S. Appl. No. 15/468,951, filed Mar. 24, 2017.
U.S. Appl. No. 15/468,559, filed Mar. 24, 2017.
U.S. Appl. No. 15/468,282, filed Mar. 24, 2017.
U.S. Appl. No. 15/468,314, filed Mar. 24, 2017.
U.S. Appl. No. 15/468,274, filed Mar. 24, 2017.
U.S. Appl. No. 15/468,303, filed Mar. 24, 2017.
U.S. Appl. No. 15/469,374, filed Mar. 24, 2017.
U.S. Appl. No. 15/476,636, filed Mar. 31, 2017.
U.S. Appl. No. 15/479,256, filed Apr. 4, 2017.
U.S. Appl. No. 15/610,526, filed May 31, 2017.
U.S. Notice of Allowance dated Oct. 19, 2017, from related U.S. Appl. No. 15/179,957, 5 pages.
U.S. Notice of Allowance dated Oct. 23, 2017, from related U.S. Appl. No. 15/003,797, 6 pages.
U.S. Office Action dated Nov. 24, 2017, from related U.S. Appl. No. 15/003,145, 14 pages.
U.S. Office Action dated Nov. 27, 2017, from related U.S. Appl. No. 15/468,386, 28 pages.
Bui et al., "Noninvasive Fault Monitoring of Electrical Machines by Solving the Steady-State Magnetic Inverse Problem," in IEEE Transactions on Magnetics, vol. 44, No. 6, pp. 1050-1053, Jun. 24, 2008.
Chadebec et al., "Rotor fault detection of electrical machines by low frequency magnetic stray field analysis," 2005 5th IEEE International Symposium on Diagnostics for Electric Machines, Power Electronics and Drives, Vienna, 2005, submitted Mar. 22, 2006, pp. 1-6.
Froidurot et al., "Magnetic discretion of naval propulsion machines," in IEEE Transactions on Magnetics, vol. 38, No. 2, pp. 1185-1188, Mar. 2002.
IEEE Std 802.11 TM-2012 Wireless LAN Medium Access Control (MAC) and Physical Layer (PHY) Specifications, 1 page.
Kwon et al., "Analysis of the far field of permanent-magnet motors and effects of geometric asymmetries and unbalance in magnet design," in IEEE Transactions on Magnetics, vol. 40, No. 2, pp. 435-442, Mar. 2004.

(56) References Cited

OTHER PUBLICATIONS

Maertz et al., "Vector magnetic field microscopy using nitrogen vacancy centers in diamond", Applied Physics Letters 96, No. 9, Mar. 1, 2010, pp. 092504-1-092504-3.
U.S. Notice of Allowance dated Feb. 2, 2018, from related U.S. Appl. No. 15/003,292, 8 pages.
U.S. Notice of Allowance dated Feb. 21, 2018, from related U.S. Appl. No. 15/003,176, 9 pages.
U.S. Office Action dated Feb. 1, 2018, from related U.S. Appl. No. 15/003,577, 16 pages.
U.S. Office Action dated Feb. 5, 2018, from related U.S. Appl. No. 15/450,504, 12 pages.
U.S. Office Action dated Jan. 26, 2018, from related U.S. Appl. No. 15/003,678, 14 pages.
U.S. Office Action dated Mar. 27, 2018, from related U.S. Appl. No. 15/468,386, 21 pages.
U.S. Office Action dated Mar. 28, 2018, from related U.S. Appl. No. 15/003,177, 12 pages.
U.S. Office Action dated Mar. 5, 2018, from related U.S. Appl. No. 14/866,730, 14 pages.
U.S. Office Action dated Mar. 8, 2018, from related U.S. Appl. No. 15/380,691, 12 pages.
U.S. Office Action dated Mar. 8, 2018, from related U.S. Appl. No. 15/479,256, 30 pages.
Wegerich, "Similarity based modeling of time synchronous averaged vibration signals for machinery health monitoring," 2004 IEEE Aerospace Conference Proceedings (IEEE Cat. No. 04TH8720), 2004, pp. 3654-3662 vol. 6.
Wikipedia, "Continuous phase modulation", downloaded from https://web.archive.org/web/20151017015236/https://en.wikipedia.org/wiki/Continuous_phase_modulation on May 10, 2017, 3 pages.
Wikipedia, "Minimum-shift keying", downloaded from https://web.archive.org/web/20151017175828/https://en.wikipedia.org/wiki/Minimum-shift_keying on May 10, 2017, 2 pages.
International Search Report and Written Opinion from related PCT application PCT/US2017/035315 dated Aug. 24, 2017, 7 pages.
Ramsey, et al., "Phase Shifts in the Molecular Beam Method of Separated Oscillating Fields", Physical Review, vol. 84, No. 3, Nov. 1, 1951, pp. 506-507.
U.S. Notice of Allowance on U.S. Appl. No. 14/676,740 dated Sep. 1, 2017, 7 pages.
U.S. Notice of Allowance on U.S. Appl. No. 15/003,206 dated Sep. 18, 2017, 11 pages.
U.S. Notice of Allowance on U.S. Appl. No. 15/003,281 dated Sep. 26, 2017, 7 pages.
U.S. Notice of Allowance on U.S. Appl. No. 15/476,636 dated Sep. 14, 2017, 10 pages.
U.S. Office Action on U.S. Appl. No. 15/003,176 dated Sep. 27, 2017, 8 pages.
U.S. Office Action on U.S. Appl. No. 15/003,292 dated Sep. 8, 2017, 8 pages.
Teeling-Smith et al., "Electron Paramagnetic Resonance of a Single NV Nanodiamond Attached to an Individual Biomolecule", Biophysical Journal 110, May 10, 2016, pp. 2044-2052.
UK Office Action dated Jun. 8, 2018, from related application No. GB1617438.5, 3 pages.
U.S. Final Office Action dated Jul. 26, 2018 from related U.S. Appl. No. 15/003,177, 14 pages.
U.S. Non-Final Office Action dated Aug. 6, 2018 from related U.S. Appl. No. 15/376,244, 28 pages.
U.S. Non-Final Office Action dated Aug. 9, 2018 from related U.S. Appl. No. 15/003,309, 22 pages.
U.S. Non-Final Office Action dated Jul. 20, 2018 from related U.S. Appl. No. 15/350,303, 13 pages.
U.S. Non-Final Office Action dated Jul. 26, 2018 from related U.S. Appl. No. 15/380,419, 11 pages.
U.S. Non-Final Office Action dated Jul. 3, 2018 from related U.S. Appl. No. 15/003,396, 19 pages.
U.S. Notice of Allowance dated Jul. 18, 2018 from related U.S. Appl. No. 15/468,386, 12 pages.
U.S. Notice of Allowance dated Jun. 27, 2018 from related U.S. Appl. No. 15/003,519, 21 pages.
U.S. Notice of Allowance dated May 15, 2018, from related U.S. Appl. No. 15/003,209, 7 pages.
U.S. Notice of Allowance dated May 16, 2018, from related U.S. Appl. No. 15/003,145, 8 pages.
U.S. Office Action dated Jun. 19, 2018, from related U.S. Appl. No. 15/450,504, 12 pages.
Niu, "Crack Detection of Power Line Based on Metal Magnetic Memory Non-destructive", TELKOMNIKA Indonesian Journal of Electrical Engineering, vol. 12, No. 11, Nov. 1, 2014, 1 page (Abstract only).
U.S. Notice of Allowance for U.S. Appl. No. 14/866,730 dated Aug. 15, 2018, 9 pages.
U.S. Non-Final Office Action for U.S. Appl. No. 15/454,162 dated Sep. 10, 2018, 13 pages.
U.S. Final Office Action for U.S. Appl. No. 15/479,256 dated Sep. 10, 2018, 20 pages.
European Extended Search Report for Appl. Ser. No. 16743879.5 dated Sep. 11, 2018, 11 pages.
U.S. Office Action for U.S. Appl. No. 15/468,397 dated Sep. 13, 2018, 7 pages.
U.S. Final Office Action for U.S. Appl. No. 15/380,691 dated Sep. 21, 2018, 12 pages.
U.S. Non-Final Office Action for U.S. Appl. No. 15/446,373 dated Oct. 1, 2018, 13 pages.
U.S. Non-Final Office Action for U.S. Appl. No. 15/443,422 dated Oct. 2, 2018, 16 pages.

* cited by examiner

| Freq (GHz) | +10 dBm Power 5 layer Cu with metal strip | |
| --- | --- | --- |
| | E-field (v/m) | H-field (A/m) |
| 2.0 | 200 | 1.40 |
| 2.2 | 63 | 1.10 |
| 2.4 | 50 | 1.00 |
| 2.6 | 56 | 1.30 |
| 2.8 | 6 | 1.90 |
| 3.0 | 120 | 2.70 |
| 3.2 | 338 | 0.50 |
| 3.4 | 101 | 2.80 |
| 3.6 | 48 | 1.80 |
| 3.8 | 110 | 1.70 |
| 4.0 | 131 | 0.30 |

FIG. 16

MAGNETO-OPTICAL DEFECT CENTER MAGNETOMETER

CROSS-REFERENCE TO RELATED PATENT APPLICATIONS

This application is claims priority to U.S. Provisional Patent Application No. 62/343,843, filed May 31, 2016, entitled "DIAMOND NITROGEN VACANCY MAGNETOMETERS," the disclosure of which is incorporated by reference herein in its entirety. This application is related to and claims priority to U.S. Provisional Patent Application No. 62/343,492, filed May 31, 2016, entitled "LAYERED RF COIL FOR MAGNETOMETER", U.S. Non-Provisional patent application Ser. No. 15/380,691, filed Dec. 15, 2016, entitled "LAYERED RF COIL FOR MAGNETOMETER,", U.S. Provisional Patent Application No. 62/343,746, filed May 31, 2016, entitled "DNV DEVICE INCLUDING LIGHT PIPE WITH OPTICAL COATINGS", U.S. Provisional Patent Application No. 62/343,750, filed May 31, 2016, entitled "DNV DEVICE INCLUDING LIGHT PIPE", U.S. Provisional Patent Application No. 62/343,758, filed May 31, 2016, entitled "OPTICAL FILTRATION SYSTEM FOR DIAMOND MATERIAL WITH NITROGEN VACANCY CENTERS", U.S. Provisional Patent Application No. 62/343,818, filed May 31, 2016, entitled "DIAMOND NITROGEN VACANCY MAGNETOMETER INTEGRATED STRUCTURE", U.S. Provisional Patent Application No. 62/343,600, filed May 31, 2016, entitled "TWO-STAGE OPTICAL DNV EXCITATION", U.S. Non-Provisional patent application Ser. No. 15/382,045, filed Dec. 16, 2016, entitled "TWO-STAGE OPTICAL DNV EXCITATION," U.S. Provisional Patent Application No. 62/343,602, filed May 31, 2016, entitled "SELECTED VOLUME CONTINUOUS ILLUMINATION MAGNETOMETER", and U.S. Non-Provisional patent application Ser. No. 15/380,419, filed Dec. 15, 2016, entitled "SELECTED VOLUME CONTINUOUS ILLUMINATION MAGNETOMETER," the entire contents of each are incorporated by reference herein in their entirety.

FIELD

The present disclosure generally relates to magnetometers, and more particularly, to magneto-optical defect center magnetometers, such as diamond nitrogen vacancy (DNV) magnetometers.

BACKGROUND

A number of industrial applications, as well as scientific areas such as physics and chemistry can benefit from magnetic detection and imaging with a device that has extraordinary sensitivity, ability to capture signals that fluctuate very rapidly (bandwidth) all with a substantive package that is extraordinarily small in size, efficient in power and infinitesimal in volume.

Atomic-sized magneto-optical defect center elements, such as nitrogen-vacancy (NV) centers in diamond lattices, have excellent sensitivity for magnetic field measurement and enable fabrication of small magnetic sensors that can readily replace existing-technology (e.g., Hall-effect) systems and devices. The DNV sensors are maintained in room temperature and atmospheric pressure and can be even used in liquid environments. A green optical source (e.g., a micro-LED) can optically excite NV centers of the DNV sensor and cause emission of fluorescence radiation (e.g., red light) under off-resonant optical excitation. A magnetic field generated, for example, by a microwave coil can probe degenerate triplet spin states (e.g., with ms=−1, 0, +1) of the NV centers to split proportional to an external magnetic field projected along the NV axis, resulting in two spin resonance frequencies. The distance between the two spin resonance frequencies is a measure of the strength of the external magnetic field. A photo detector can measure the fluorescence (red light) emitted by the optically excited NV centers.

SUMMARY

Methods and systems are described for, among other things, a magneto-optical defect center magnetometer.

Some embodiments relate to a magneto-optical defect center magnetometer that includes an excitation source, a magneto-optical defect center element, a collection device, a top plate, a bottom plate, and a printed circuit board. The excitation source, the magneto-optical defect center element, and the collection device are each mounted to the printed circuit board.

In some implementations, the excitation source is positioned along a first axis relative to the printed circuit board and the collection device is positioned along a second axis relative to the printed circuit board. In some implementations, the magneto-optical defect center magnetometer includes excitation source circuitry mounted to the printed circuit board proximate to the excitation source. In some implementations, the magneto-optical defect center magnetometer includes collection device circuitry mounted to the printed circuit board proximate to the collection device. In some implementations, the magneto-optical defect center magnetometer includes an RF element mounted to the printed circuit board and RF amplifier circuitry mounted to the printed circuit board proximate to the RF device. In some implementations, the magneto-optical defect center magnetometer includes an optical waveguide assembly that includes an optical waveguide and at least one optical filter coating, and the optical waveguide assembly is configured to transmit light emitted from the diamond having nitrogen vacancies to the collection device. In some implementations, the optical waveguide comprises a light pipe. In some implementations, the optical filter coating transmits greater than about 99% of light with a wavelength of about 650 nm to about 850 nm. In some implementations, the optical filter coating transmits less than 0.1% of light with a wavelength of less than about 600 nm. In some implementations, the optical filter coating transmits greater than about 99% of light with a wavelength of about 650 nm to about 850 nm, and transmits less than 0.1% of light with a wavelength of less than about 600 nm. In some implementations, the optical filter coating is disposed on an end surface of the optical waveguide adjacent the collection device. In some implementations, a first optical filter coating is disposed on an end surface of the optical waveguide adjacent the collection device and a second optical filter coating is disposed on an end surface of the optical waveguide adjacent the diamond having nitrogen vacancies. In some implementations, the light pipe has an aperture with a size that is smaller than a size of the collection device. In some implementations, the light pipe has an aperture with a size greater than a size of a surface of the magneto-optical defect center element adjacent to the light pipe. In some implementations, the light pipe has an aperture with a size that is smaller than a size of the collection device and greater than a size of a surface of the magneto-optical defect center element adjacent the light pipe. In some implementations, the optical waveguide assembly further comprises an optical coupling material disposed between the light pipe and the magneto-optical defect center element, and the optical coupling material is configured to optically couple the light pipe to the magneto-optical defect center element. In some implementations, the optical waveguide assembly further comprises an optical coupling material disposed between the light pipe and the collection device, and the optical coupling material is configured to optically couple the light pipe to the collection device. In some implementations, an end surface of the light pipe adjacent to the magneto-optical defect center element extends in a plane parallel to a surface of the magneto-optical defect center element adjacent to the light pipe. In some implementations, the magneto-optical defect center magnetometer includes a second optical waveguide assembly and a second collection device, and the second optical waveguide assembly is configured to transmit light emitted from the magneto-optical defect center element to the second collection device. In some implementations, the magneto-optical defect center magnetometer includes an optical filter and the magneto-optical defect center element receives optical excitation based, at least in part, on generation of light corresponding to a first wavelength from the excitation source. The collection device is configured to receive at least a first portion of light corresponding to a second wavelength and the optical filter is configured to provide at least a portion of light corresponding to the second wavelength to the collection device. In some implementations, the optical filter is further configured to transmit light corresponding to the first wavelength. In some implementations, light corresponding to the first wavelength comprises green and light corresponding to the second wavelength comprises red. In some implementations, the optical filter comprises an optical coating, and wherein the optical coating comprises one or more layers configured to at least one of transmit or reflect light. In some implementations, the optical filter is disposed at least one of above, beneath, behind, or in front of the collection device. In some implementations, the optical filter is configured to enclose the magneto-optical defect center element. In some implementations, the optical filter is disposed at least one of above, beneath, behind, or in front of the magneto-optical defect center element. In some implementations, the collection device comprises a receiving ends, and wherein the receiving ends are disposed proximate to the magneto-optical defect center element. In some implementations, the collection device forms a gap, and wherein a predetermined dimension corresponding to the optical filter is configured to extend beyond a predetermined dimension corresponding to the gap. In some implementations, the magneto-optical defect center element is disposed between the receiving ends. In some implementations, the magneto-optical defect center magnetometer includes a RF excitation source configured to provide RF excitation to the magneto-optical defect center element. In some implementations, the optical filter comprises a dichroic filter. In some implementations, the excitation source, the magneto-optical defect center element, and the collection device are each aligned and positioned relative to the top plate, bottom plate, and printed circuit board by a corresponding two-point orientation system. In some implementations, the excitation source, the magneto-optical defect center element, and the collection device are positioned in a single plane. In some implementations, the magneto-optical defect center magnetometer includes a support element for the excitation source. In some implementations, the support element comprises one or more alignment pins for the two-point orientation system and wherein the top plate comprises one or more alignment openings for the two-point orientation system. In some implementations, the excitation source comprises one or more of a laser diode or a focusing lens. In some implementations, the support element comprises an asymmetrical alignment pin for the two-point orientation system and wherein the top plate comprises an asymmetrical alignment opening for the two-point orientation system. In some implementations, the excitation source comprises one or more of a laser diode or a focusing lens. In some implementations, the support element is formed of stainless steel, titanium, aluminum, carbon fiber, plastic, or a composite. In some implementations, the magneto-optical defect center magnetometer includes a support element for the collection device. In some implementations, the support element comprises one or more alignment pins for the two-point orientation system and wherein the top plate comprises one or more alignment openings for the two-point orientation system. In some implementations, the collection device comprises one or more of a light pipe or a photo diode. In some implementations, the support element comprises an asymmetrical alignment pin for the two-point orientation system and wherein the top plate comprises an asymmetrical alignment opening for the two-point orientation system. In some implementations, the collection device comprises one or more of a light pipe or a photo diode. In some implementations, the support element is formed of stainless steel, titanium, aluminum, carbon fiber, plastic, or a composite. In some implementations, the top plate is formed of stainless steel, titanium, aluminum, carbon fiber, or a composite. In some implementations, the bottom plate is formed of stainless steel, titanium, aluminum, carbon fiber, or a composite. In some implementations, the excitation source comprises an optical light source including a readout optical light source configured to provide optical excitation to the magneto-optical defect center element to transition relevant magneto-optical defect electrons to excited spin states in the magneto-optical defect center element and a reset optical light source configured to provide optical light to the magneto-optical defect center element to reset spin states in the magneto-optical defect center element to a ground state. The reset optical light source provides a higher power light than the readout optical light source. In some implementations, the readout optical light source is a laser and the reset optical light source is a bank of LED flash-bulbs. In some implementations, the readout optical light source is an LED and the reset optical light source is a bank of LED flash-bulbs. In some implementations, the readout optical light source has a higher duty cycle than the reset optical light source. In some implementations, the excitation source comprises an optical light source including a readout optical light source configured to illuminate light in a first illumination volume of the magneto-optical defect center element and a reset optical light source configured to illuminate light in a second illumination volume of the magneto-optical defect center element The second illumination volume is larger than and encompassing the first illumination volume, and the reset optical light source provides a higher power light than the readout optical light source. In some implementations, the readout optical light source is a laser and the reset optical light source is a bank of LED flash-bulbs. In some implementations, the readout optical light source is an LED and the reset optical light source is a bank of LED flash-bulbs. In some implementations, the readout optical light source has a higher duty cycle than the reset optical light source. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils each having a spiral shape. In some implementations, the coils are arranged in layers one above another. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils arranged in layers one above another and to have a uniform spacing between each other. In some implementations, the coils each have a spiral shape. In some implementations, the magneto-optical defect center element is a diamond having nitrogen vacancies.

Another embodiment relates to a magneto-optical defect center magnetometer that includes a magneto-optical defect center element, an excitation source, a collection device, a top plate, a bottom plate, a printed circuit board, excitation source circuitry mounted to the printed circuit board proximate to the excitation source, and collection device circuitry mounted to the printed circuit board proximate to the collection device. The excitation source, the magneto-optical defect center element, and the collection device are each mounted to the printed circuit board.

In some implementations, the excitation source is positioned along a first axis relative to the printed circuit board and wherein the collection device is positioned along a second axis relative to the printed circuit board. In some implementations, the magneto-optical defect center magnetometer includes an RF element mounted to the printed circuit board and RF amplifier circuitry mounted to the printed circuit board proximate to the RF device. In some implementations, the magneto-optical defect center magnetometer includes an optical waveguide assembly that includes an optical waveguide and at least one optical filter coating, wherein the optical waveguide assembly is configured to transmit light emitted from the diamond having nitrogen vacancies to the collection device. In some implementations, the magneto-optical defect center magnetometer includes an optical filter, and the magneto-optical defect center element receives optical excitation based, at least in part, on generation of light corresponding to a first wavelength from the excitation source. The collection device is configured to receive at least a first portion of light corresponding to a second wavelength, and the optical filter is configured to provide at least a portion of light corresponding to the second wavelength to the collection device. In some implementations, the excitation source, the magneto-optical defect center element, and the collection device are each aligned and positioned relative to the top plate, bottom plate, and printed circuit board by a corresponding two-point orientation system. In some implementations, the excitation source comprises an optical light source including a readout optical light source configured to provide optical excitation to the magneto-optical defect center element to transition relevant magneto-optical defect electrons to excited spin states in the magneto-optical defect center element and a reset optical light source configured to provide optical light to the magneto-optical defect center element to reset spin states in the magneto-optical defect center element to a ground state. The reset optical light source provides a higher power light than the readout optical light source. In some implementations, the excitation source comprises an optical light source including a readout optical light source configured to illuminate light in a first illumination volume of the magneto-optical defect center element and a reset optical light source configured to illuminate light in a second illumination volume of the magneto-optical defect center element. The second illumination volume is larger than and encompassing the first illumination volume, and the reset optical light source provides a higher power light than the readout optical light source. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils each having a spiral shape. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils arranged in layers one above another and to have a uniform spacing between each other. In some implementations, the magneto-optical defect center element is a diamond having nitrogen vacancies.

A further embodiment relates to a magneto-optical defect center magnetometer having a magneto-optical defect center element, an excitation source, a collection device, an RF element, a top plate, a bottom plate, a printed circuit board, excitation source circuitry mounted to the printed circuit board proximate to the excitation source, collection device circuitry mounted to the printed circuit board proximate to the collection device, and RF amplifier circuitry mounted to the printed circuit board proximate to the RF device. The excitation source, the magneto-optical defect center element, the collection device, and the RF element are each mounted to the printed circuit board and the excitation source is positioned along a first axis relative to the printed circuit board and the collection device is positioned along a second axis relative to the printed circuit board.

In some implementations, the magneto-optical defect center magnetometer includes an optical waveguide assembly that includes an optical waveguide and at least one optical filter coating, and the optical waveguide assembly is configured to transmit light emitted from the diamond having nitrogen vacancies to the collection device. In some implementations, the magneto-optical defect center magnetometer includes an optical filter. The magneto-optical defect center element receives optical excitation based, at least in part, on generation of light corresponding to a first wavelength from the excitation source, the collection device is configured to receive at least a first portion of light corresponding to a second wavelength, and the optical filter is configured to provide at least a portion of light corresponding to the second wavelength to the collection device. In some implementations, the excitation source, the magneto-optical defect center element, and the collection device are each aligned and positioned relative to the top plate, bottom plate, and printed circuit board by a corresponding two-point orientation system. In some implementations, the excitation source comprises an optical light source including a readout optical light source configured to provide optical excitation to the magneto-optical defect center element to transition relevant magneto-optical defect electrons to excited spin states in the magneto-optical defect center element and a reset optical light source configured to provide optical light to the magneto-optical defect center element to reset spin states in the magneto-optical defect center element to a ground state. The reset optical light source provides a higher power light than the readout optical light source. In some implementations, the excitation source comprises an optical light source including a readout optical light source configured to illuminate light in a first illumination volume of the magneto-optical defect center element and a reset optical light source configured to illuminate light in a second illumination volume of the magneto-optical defect center element. The second illumination volume is larger than and encompassing the first illumination volume, and the reset optical light source provides a higher power light than the readout optical light source. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils each having a spiral shape. In some implementations, the magneto-optical defect center magnetometer includes a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils arranged in layers one above another and to have a uniform spacing between each other. In some implementations, the magneto-optical defect center element is a diamond having nitrogen vacancies.

BRIEF DESCRIPTION OF THE DRAWINGS

The details of one or more implementations are set forth in the accompanying drawings and the description below. Other features, aspects, and advantages will become apparent from the description, the drawings, and the claims, in which:

FIG. 16 is a table illustrating the electric field and magnetic field generated by the RF excitation source in a region of the NV diamond material at frequencies from 2.0 to 4.0 GHz for the five layer coil arrangement with spiral shaped coils;

It will be recognized that some or all of the figures are schematic representations for purposes of illustration. The figures are provided for the purpose of illustrating one or more embodiments with the explicit understanding that they will not be used to limit the scope or the meaning of the claims.

DETAILED DESCRIPTION

In some aspects, methods and systems are disclosed for a magneto-optical defect center magnetometer, such as a DNV magnetometer.

Figure 1:
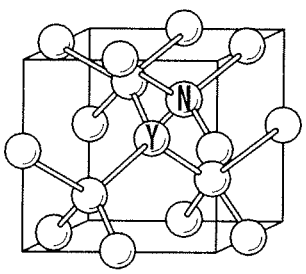
FIG. 1 illustrates an orientation of an NV center in a diamond lattice.

Magneto-optical defects, such as nitrogen-vacancy centers (NV centers), are defects in an element's, such as a diamond's, crystal structure, which can purposefully be manufactured, such as in synthetic diamonds as shown in FIG. 1. In general, when excited by green light and microwave radiation, the NV centers cause the diamond to generate red light. When an excited NV center diamond is exposed to an external magnetic field the frequency of the microwave radiation at which the diamond generates red light and the intensity of the light change. By measuring the changes, the NV centers can be used to accurately detect the magnetic field strength.

The NV center may exist in a neutral charge state or a negative charge state. Conventionally, the neutral charge state uses the nomenclature NV$^0$, while the negative charge state uses the nomenclature NV, which is adopted in this description.

The NV center has a number of electrons, including three unpaired electrons, each one from the vacancy to a respective of the three carbon atoms adjacent to the vacancy, and a pair of electrons between the nitrogen and the vacancy. The NV center, which is in the negatively charged state, also includes an extra electron.

Figure 2:
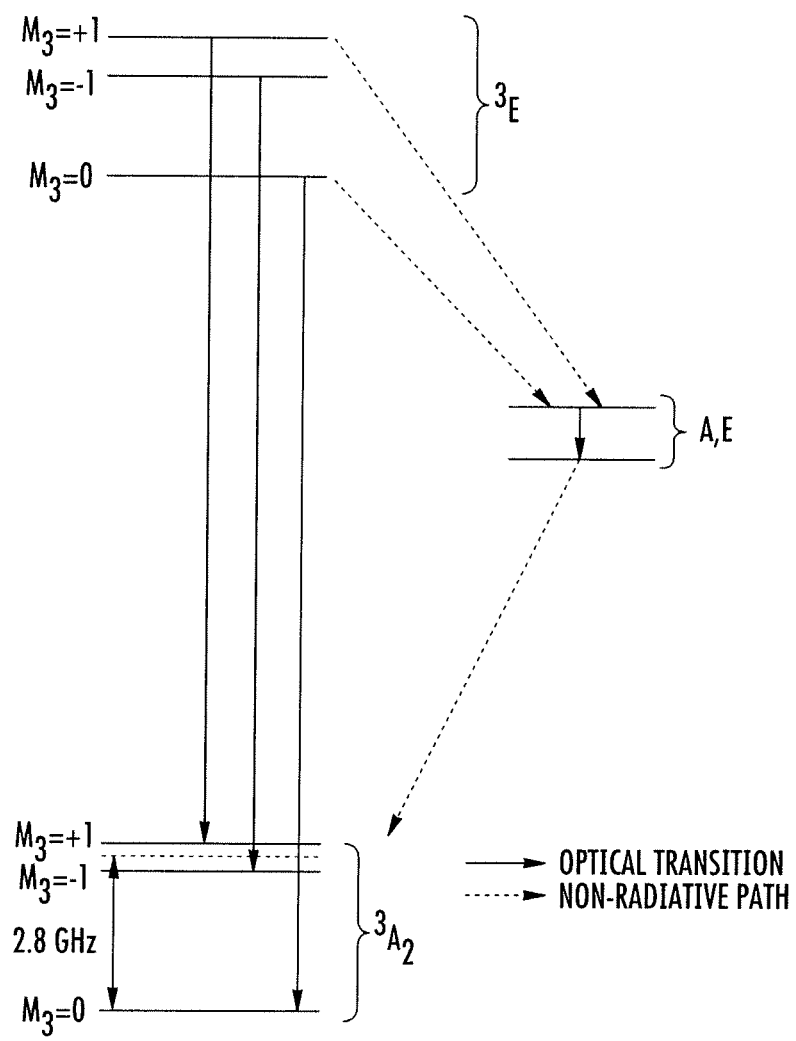
FIG. 2 illustrates an energy level diagram showing energy levels of spin states for the NV center.

The NV center has rotational symmetry and, as shown in FIG. 2, has a ground state, which is a spin triplet with $^3A_2$ symmetry with one spin state $m_s=0$, and two further spin states $m_s=+1$, and $m_s=-1$. In the absence of an external magnetic field, the $m_s=\pm1$ energy levels are offset from the $m_s=0$ due to spin-spin interactions, and the $m_s=\pm1$ energy levels are degenerate, i.e., they have the same energy. The $m_s=0$ spin state energy level is split from the $m_s=\pm1$ energy levels by an energy of approximately 2.87 GHz for a zero external magnetic field.

Introducing an external magnetic field with a component along the NV axis lifts the degeneracy of the $m_s=\pm1$ energy levels, splitting the energy levels $m_s=\pm1$ by an amount $2g\mu_B Bz$, where g is the g-factor, $\mu_B$ is the Bohr magneton, and Bz is the component of the external magnetic field along the NV axis. This relationship is correct to a first order and inclusion of higher order corrections is a straightforward matter and will not affect the computational and logic steps in the systems and methods described below.

The NV center electronic structure further includes an excited triplet state $^3E$ with corresponding $m_s=0$ and $m_s=\pm1$ spin states. The optical transitions between the ground state $^3A_2$ and the excited triplet $^3E$ are predominantly spin conserving, meaning that the optical transitions are between initial and final states that have the same spin. For a direct transition between the excited triplet $^3E$ and the ground state $^3A_2$, a photon of red light is emitted with a photon energy corresponding to the energy difference between the energy levels of the transitions.

There is, however, an alternative non-radiative decay route from the triplet $^3E$ to the ground state $^3A_2$ via intermediate electron states, which are thought to be intermediate singlet states A, E with intermediate energy levels. Significantly, the transition rate from the $m_s=\pm1$ spin states of the excited triplet $^3E$ to the intermediate energy levels is significantly greater than the transition rate from the $m_s=0$ spin state of the excited triplet $^3E$ to the intermediate energy levels. The transition from the singlet states A, E to the ground state triplet $^3A_2$ predominantly decays to the $m_s=0$ spin state over the $m_s=\pm1$ spins states. These features of the decay from the excited triplet $^3E$ state via the intermediate singlet states A, E to the ground state triplet $^3A_2$ allows that if optical excitation is provided to the system, the optical excitation will eventually pump the NV center into the $m_s=0$ spin state of the ground state $^3A_2$. In this way, the population of the $m_s=0$ spin state of the ground state $^3A_2$ may be "reset" to a maximum polarization determined by the decay rates from the triplet $^3E$ to the intermediate singlet states.

Another feature of the decay is that the fluorescence intensity due to optically stimulating the excited triplet $^3E$ state is less for the $m_s=\pm1$ states than for the $m_s=0$ spin state. This is so because the decay via the intermediate states does not result in a photon emitted in the fluorescence band, and because of the greater probability that the $m_s=\pm1$ states of the excited triplet $^3E$ state will decay via the non-radiative decay path. The lower fluorescence intensity for the $m_s=\pm1$ states than for the $m_s=0$ spin state allows the fluorescence intensity to be used to determine the spin state. As the population of the $m_s=\pm1$ states increases relative to the $m_s=0$ spin, the overall fluorescence intensity will be reduced.

Figure 3:
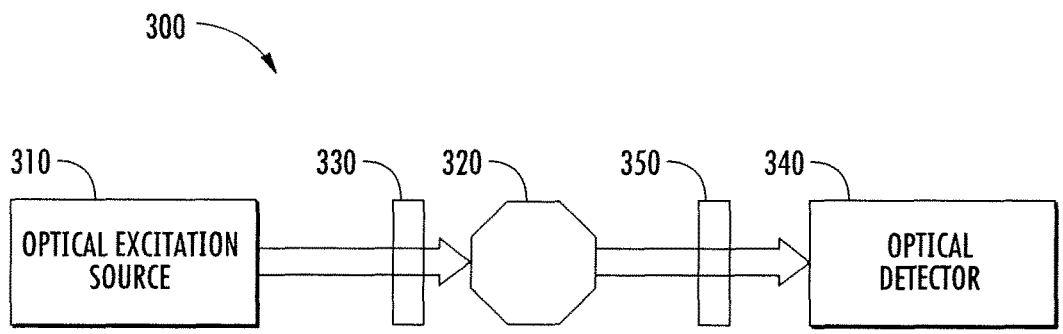
FIG. 3 illustrates a schematic diagram of a magneto-optical defect center sensor system.

FIG. 3 is a schematic diagram illustrating a NV center magnetic sensor system 300 that uses fluorescence intensity to distinguish the $m_s=\pm1$ states, and to measure the magnetic field based on the energy difference between the $m_s=+1$ state and the $m_s=-1$ state, as manifested by the RF frequencies corresponding to each state. The system 300 includes an optical excitation source 310, which directs optical excitation to an NV diamond material 320 with NV centers. The system further includes an RF excitation source 330, which provides RF radiation to the NV diamond material 320. Light from the NV diamond may be directed through an optical filter 350 to an optical detector 340.

The RF excitation source 330 may be a microwave coil, for example. The RF excitation source 330, when emitting RF radiation with a photon energy resonant with the transition energy between ground $m_s=0$ spin state and the $m_s=+1$ spin state, excites a transition between those spin states. For such a resonance, the spin state cycles between ground $m_s=0$ spin state and the $m_s=+1$ spin state, reducing the population in the $m_s=0$ spin state and reducing the overall fluorescence at resonances. Similarly, resonance and a subsequent decrease in fluorescence intensity occurs between the $m_s=0$ spin state and the $m_s=-1$ spin state of the ground state when the photon energy of the RF radiation emitted by the RF excitation source is the difference in energies of the $m_s=0$ spin state and the $m_s=-1$ spin state.

The optical excitation source 310 may be a laser or a light emitting diode, for example, which emits light in the green (light having a wavelength such that the color is green), for example. The optical excitation source 310 induces fluorescence in the red, which corresponds to an electronic transition from the excited state to the ground state. Light from the NV diamond material 320 is directed through the optical filter 350 to filter out light in the excitation band (in the green, for example), and to pass light in the red fluorescence band, which in turn is detected by the detector 340. The optical excitation light source 310, in addition to exciting fluorescence in the diamond material 320, also serves to reset the population of the $m_s=0$ spin state of the ground state $^3A_2$ to a maximum polarization, or other desired polarization.

Figure 4:
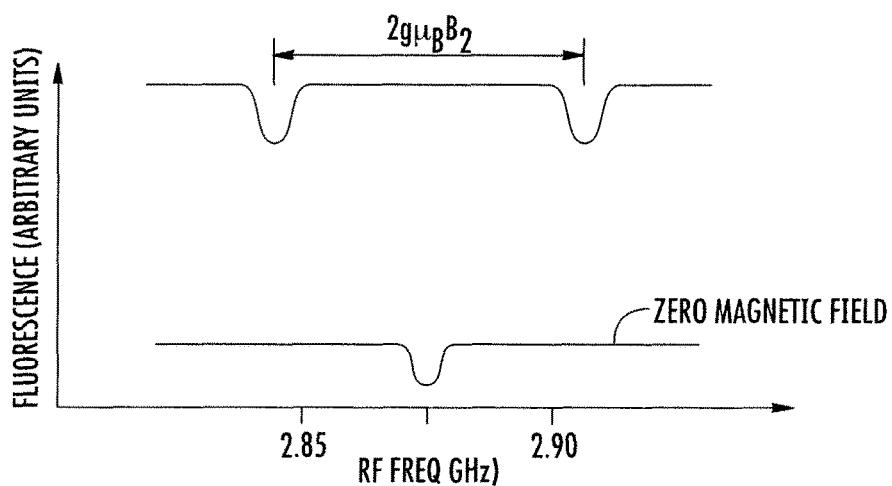
FIG. 4 is a graph illustrating the fluorescence as a function of an applied RF frequency of an NV center along a given direction for a zero magnetic field, and also for a non-zero magnetic field having a component along the NV axis.

For continuous wave excitation, the optical excitation source 310 continuously pumps the NV centers, and the RF excitation source 330 sweeps across a frequency range that includes the zero splitting (when the $m_s=\pm 1$ spin states have the same energy) photon energy of approximately 2.87 GHz. The fluorescence for an RF sweep corresponding to a diamond material 320 with NV centers aligned along a single direction is shown in FIG. 4 for different magnetic field components Bz along the NV axis, where the energy splitting between the $m_s=-1$ spin state and the $m_s=+1$ spin state increases with Bz. Thus, the component Bz may be determined. Optical excitation schemes other than continuous wave excitation are contemplated, such as excitation schemes involving pulsed optical excitation, and pulsed RF excitation. Examples of pulsed excitation schemes include Ramsey pulse sequence (described in more detail below), and spin echo pulse sequence.

Figure 5:
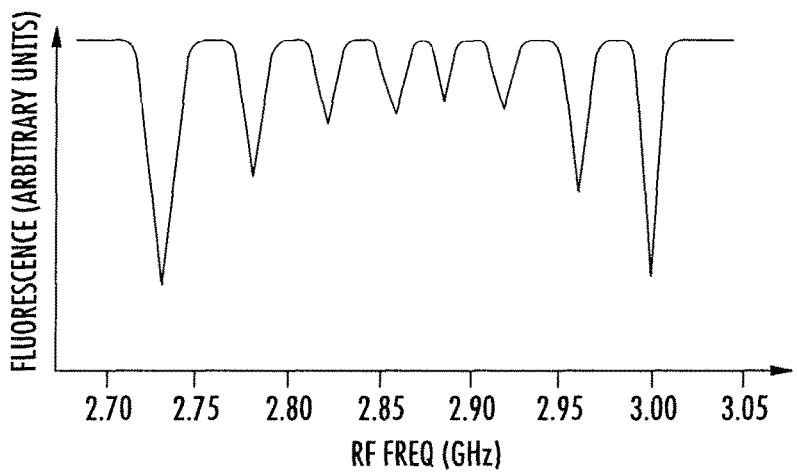
FIG. 5 is a graph illustrating the fluorescence as a function of an applied RF frequency for four different NV center orientations for a non-zero magnetic field.

In general, the diamond material 320 will have NV centers aligned along directions of four different orientation classes. FIG. 5 illustrates fluorescence as a function of RF frequency for the case where the diamond material 320 has NV centers aligned along directions of four different orientation classes. In this case, the component Bz along each of the different orientations may be determined. These results, along with the known orientation of crystallographic planes of a diamond lattice, allow not only the magnitude of the external magnetic field to be determined, but also the direction of the magnetic field.

While FIG. 3 illustrates an NV center magnetic sensor system 300 with NV diamond material 320 with a plurality of NV centers, in general, the magnetic sensor system may instead employ a different magneto-optical defect center material, with a plurality of magneto-optical defect centers. The electronic spin state energies of the magneto-optical defect centers shift with magnetic field, and the optical response, such as fluorescence, for the different spin states is not the same for all of the different spin states. In this way, the magnetic field may be determined based on optical excitation, and possibly RF excitation, in a corresponding way to that described above with NV diamond material.

Figure 6:
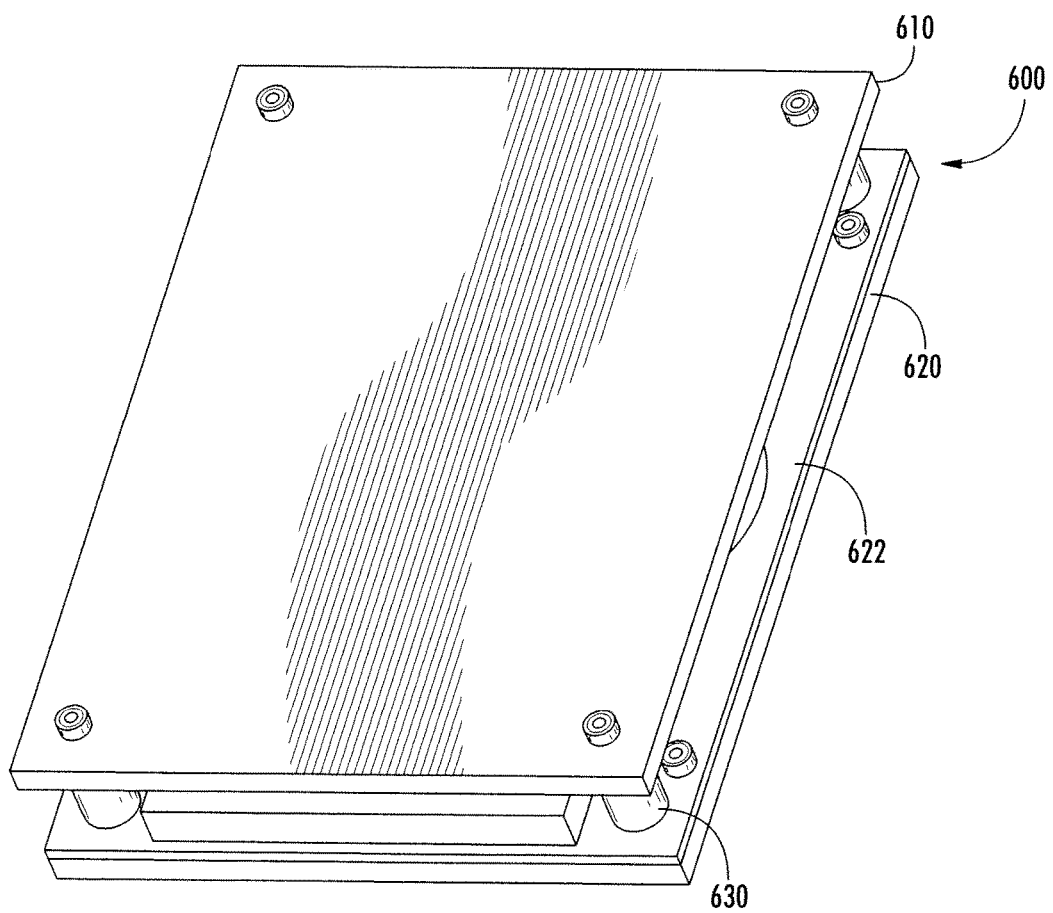
FIG. 6 is an illustrative a perspective view depicting some embodiments of a magneto-optical defect center magnetometer.

Referring generally to FIG. 6, a magneto-optical defect center magnetometer 600 may be provided that includes a top plate 610 and a bottom plate 620. The bottom plate 620 may include a printed circuit board (PCB) 622 that is configured to mount the components of the magneto-optical defect center magnetometer 600 thereto. The top plate 610 and bottom plate 620 may be formed of a material with a high stiffness and a low mass, such as stainless steel, titanium, aluminum, carbon fiber, a composite material, etc. The high stiffness of the top plate 610 and bottom plate 620 is such that any vibration modes occur outside of the range of frequencies that may negatively affect the magneto-optical defect center magnetometer 600 sensor performance. The top plate 610, bottom plate 620, and PCB 622 include alignment holes into which pins for one or more components of the magneto-optical defect center magnetometer 600 may be inserted to align the one or more components and, when the top plate and bottom plate 620 are pressed together, the pins lock the components in place to maintain alignment of the one or more components after assembly of the magneto-optical defect center magnetometer 600.

Figure 7:
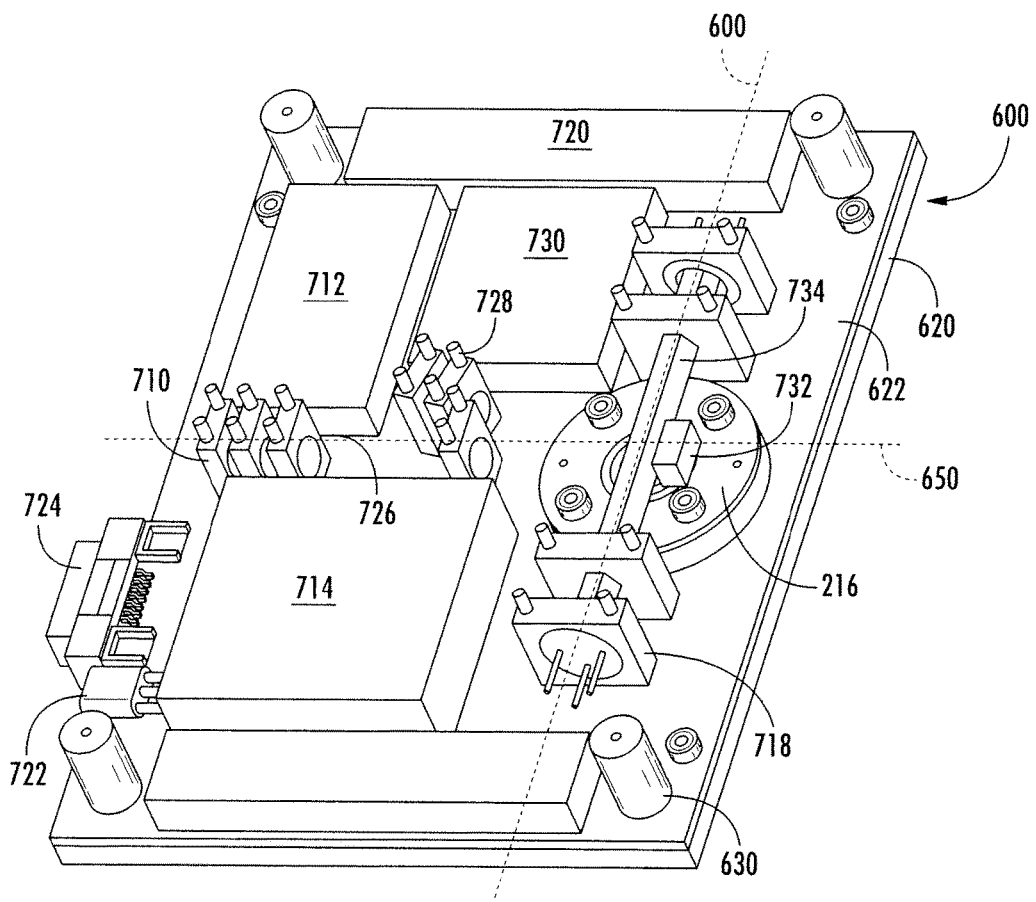
FIG. 7 is an illustrative perspective view of the magneto-optical defect center magnetometer of FIG. 6 with a top plate removed.
Figure 8:
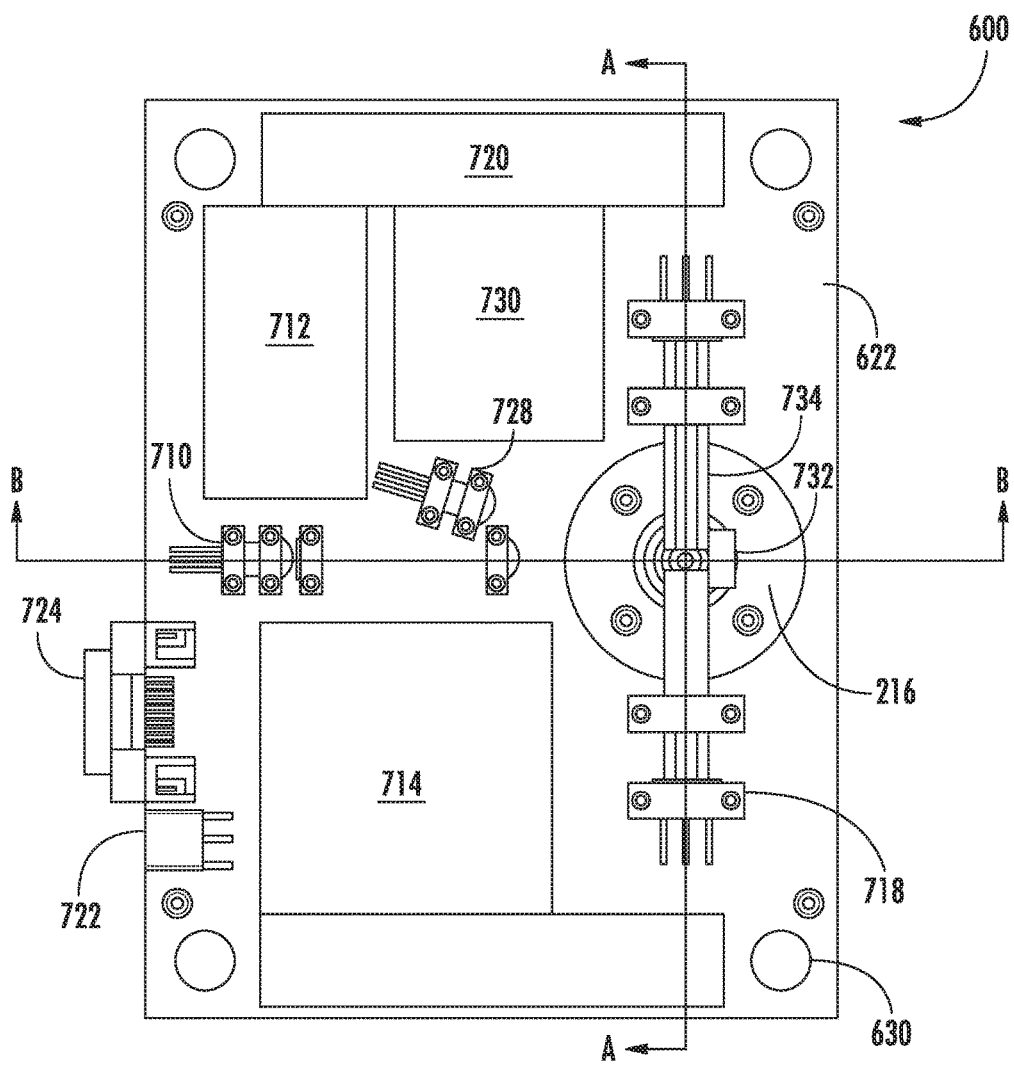
FIG. 8 is an illustrative top view depicting the magneto-optical defect center magnetometer of FIG. 6 with the top plate removed.
Figure 9:
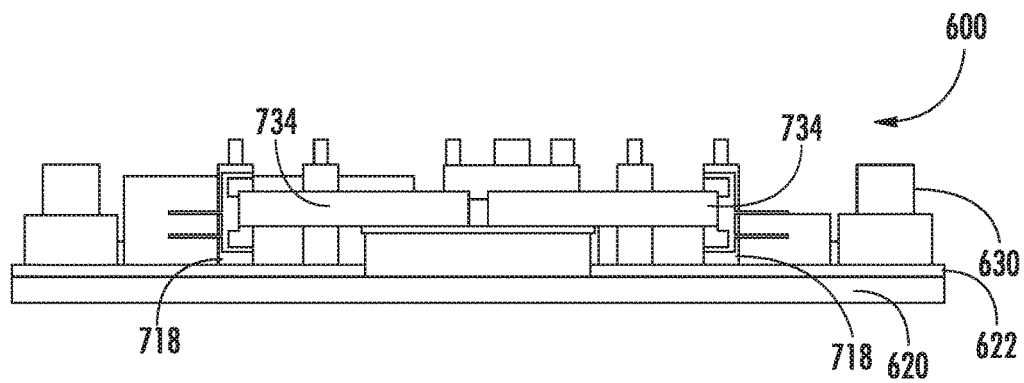
FIG. 9 is an illustrative cross-sectional view taken along line A-A and depicting the magneto-optical defect center magnetometer of FIG. 6 with the top plate removed.
Figure 10:
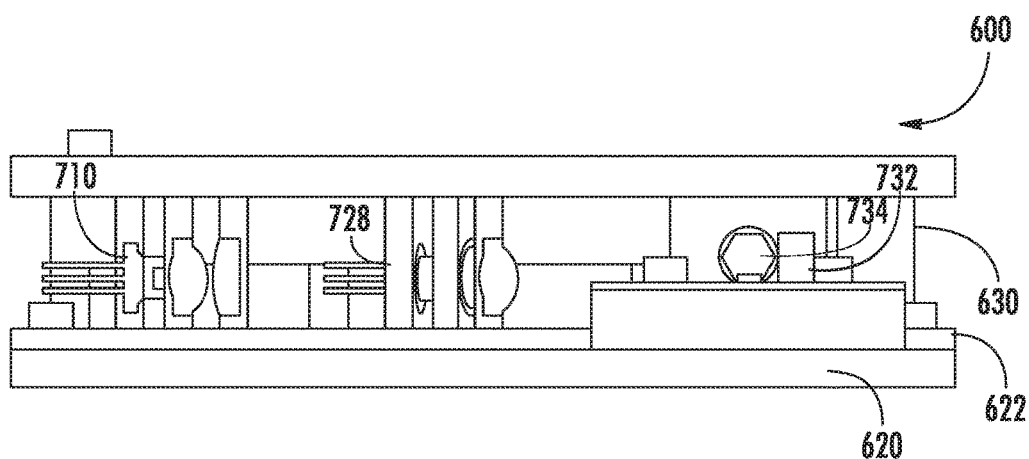
FIG. 10 is an illustrative cross-sectional view taken along line B-B and depicting the magneto-optical defect center magnetometer of FIG. 6 with the top plate attached.
Figure 11:
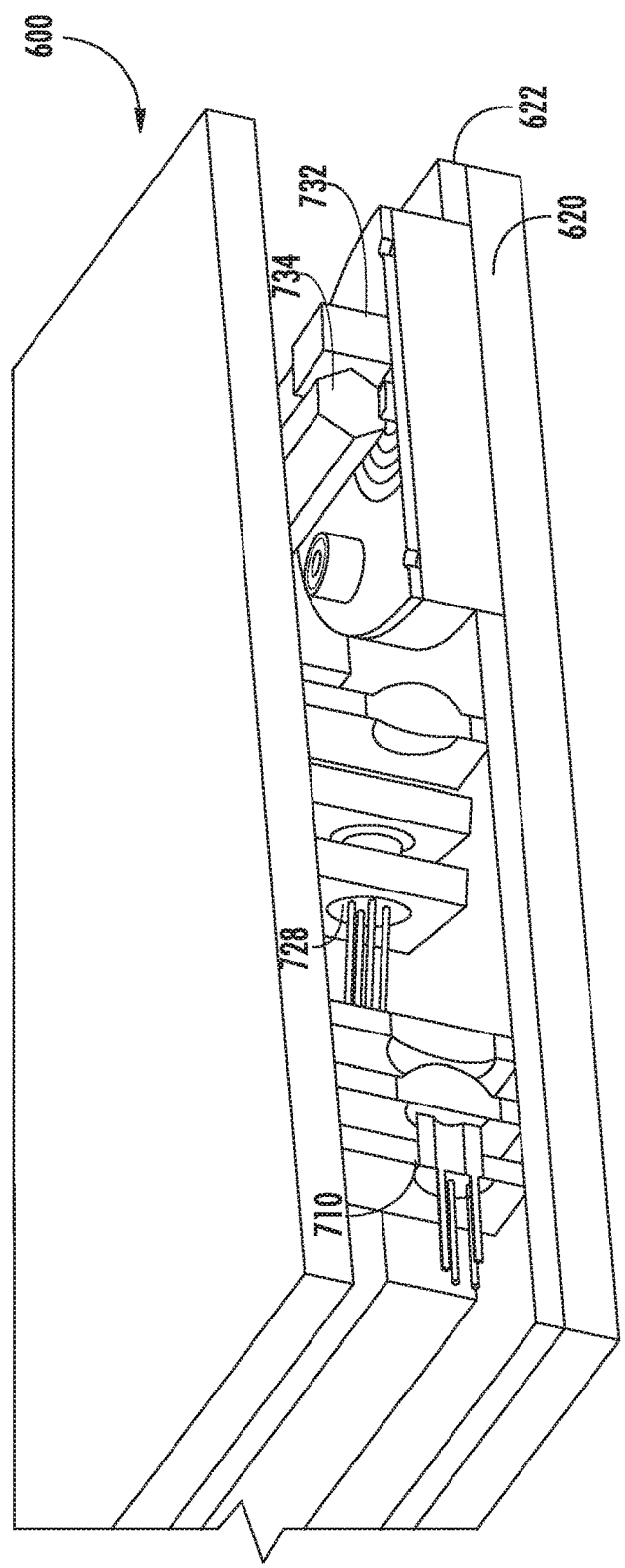
FIG. 11 is an illustrative perspective cross-sectional view taken along line B-B and depicting the DNV magnetometer of FIG. 6 with the top plate attached.

As shown in FIG. 7, the magneto-optical defect center magnetometer 600 has several components mounted between top plate 610, the bottom plate 620, and the PCB 622. The components of the magneto-optical defect center magnetometer 600 include a green laser diode 710, laser diode circuitry 712, a magneto-optical defect center element, such as diamond having nitrogen vacancies (DNV), RF amplifier circuitry 714, an RF element 716, one or more photo diodes 718, and photo diode circuitry 720. In operation, the green laser diode 710 emits green wavelength light toward the magneto-optical defect center element based on a control signal from the laser diode circuitry 712. The RF amplifier circuitry 714 receives an RF input signal via an RF connector 722. In some implementations, the RF signal is generated by a separate controller, such as an external RF wave form generator circuit. In other implementations, the RF waveform generator may be included with the magneto-optical defect center magnetometer 600. The RF amplifier circuitry 714 uses the RF input signal to control the RF element 716. The RF element 716 may include a microwave coil or coils. The RF element 716 emits RF radiation to control the spin of the magneto-optical defect centers of the magneto-optical defect center element to be aligned along a single direction, such as prior to a measurement by the magneto-optical defect center magnetometer 600. The magneto-optical defect center element, when excited by the green laser light, emits red wavelength based on external magnet fields and the emitted red light is detected by the one or more photo diodes 718. The detected red light by the photo diodes 718 may be processed by the photo diode circuitry 720 and/or may be outputted to an external circuit for processing. Based on the detected red light, the magneto-optical defect center magnetometer 600 can detect the directionality and intensity (e.g., vector) of the external magnetic field. Such a vector magnetometer may be used to detect other objects that generate magnetic fields. Power for the components and/or circuits of the magneto-optical defect center magnetometer 600 and data transmission to and/or from the magneto-optical defect center magnetometer 600 may be provided via a digital signal and power connector 724.

In some implementations, the magneto-optical defect center magnetometer 600 may include several other components to be mounted via the top plate 610, bottom plate 620, and PCB 622. Such components may include one or more focusing lenses 726, a flash laser 728 and/or flash laser focusing lenses, flash bulb driver circuitry 730, a mirror and/or filtering element 732, and/or one or more light pipes 734. The focusing lenses 726 may focus the emitted green wavelength light from the green laser diode 710 towards the magneto-optical defect center element. The flash laser 728 and/or flash laser focusing lenses may provide additional excitation green wavelength light to the magneto-optical defect center element, and the flash bulb driver circuitry 730 may control the operation of the flash laser 728. The mirror and/or filtering element 732 may be an element that is reflective for red wavelength light, but permits green wavelength light to pass through. In some implementations, the mirror and/or filtering element 732 may be applied to the magneto-optical defect center element, such as a coating, to reflect red wavelength light towards the photo diodes 718. In other implementations, the mirror and/or filtering element 732 may be a separate component that substantially surrounds or encases the magneto-optical defect center element. The one or more light pipes 734 transports red wavelength light emitted from the magneto-optical defect center element to the one or more photo diodes 718 such that the one or more photo diodes 718 may be positioned remote from the magneto-optical defect center element. Additional description may include the applications incorporated by reference.

As shown in FIG. 7, the components of the magneto-optical defect center magnetometer 600 are mounted to a single PCB 622 such that a compact magneto-optical defect center magnetometer 600 is constructed. In some current magneto-optical defect center magnetometry systems, separate components are assembled on to large stainless steel plates in laboratories for individual experimentation. Such configurations are large, cumbersome, and heavy, which limits the useful applications. Indeed, for certain configurations of magneto-optical defect center magnetometry systems with resolutions of approximately 300 picoteslas, the size of the system may be a meter or more in one or more directions. In contrast to such magneto-optical defect center magnetometry systems, the magneto-optical defect center magnetometer 600 of FIGS. 6-11 may have a weight of less than 0.5 kilograms, a power range of 1-5 watts, and a size of approximately 7.62 centimeters in the x-direction by 10.16 centimeters in the y-direction by 1.905 centimeters in the z-direction. The magneto-optical defect center magnetometer 600 may have a resolution of approximately 300 picoteslas, a bandwidth of 1 MHz, and a measurement range of 1000 microteslas. Such a compact magneto-optical defect center magnetometer 600 expands the range of potential applications for vector magneto-optical defect center magnetometry by providing a small weight, size and power magneto-optical defect center magnetometer 600. Such applications may include magneto-optical defect center vector magnetometry in aircraft, submersibles, vehicles, satellites, etc.

In the implementation shown in FIG. 7, the excitation source components of the magneto-optical defect center magnetometer 600, such as the green laser diode 710 and one or more focusing lenses 726 are aligned along a first axis 650 and are mounted to the PCB 622. The collection components of the magneto-optical defect center magnetometer 600, such as the one or more photo diodes 718, mirror and/or filtering element 732, and/or one or more light pipes 734 are aligned along a second axis 660 and are mounted to the PCB 622. The second axis 660 is in the same plane as the first axis 650 and perpendicular to the first axis 650 such that the z-dimension of the magneto-optical defect center magnetometer 600 may be reduced to a minimum that is based on the z-dimensions of the components. Furthermore, by providing the excitation source components of the magneto-optical defect center magnetometer 600 along the first axis 650 perpendicular to the collection components of the magneto-optical defect center magnetometer 600 along the second axis 660, interference (e.g., magnetic, electrical, etc.) between the components may be reduced.

As shown in FIG. 7, the corresponding circuitry (e.g., the laser diode circuitry 712, RF amplifier circuitry 714, photo diode circuitry 720, etc.) for each component of the excitation and collection components are also mounted to the single PCB 622. Thus, electrical contact etchings on the PCB 622 can be used electrically couples the corresponding circuitry to each corresponding component, thereby eliminating any unnecessary connections and/or wiring between components. Furthermore, the corresponding circuitry is positioned on the PCB 622 near each corresponding component in open portions of the PCB 622 where the optical components of the excitation source components and/or collection components are not located. Such positioning reduces the x- and y-dimensional size of the magneto-optical defect center magnetometer while also reducing the length of any electrical contact etchings to electrically couple the corresponding circuitry to a corresponding component.

Referring generally to FIGS. 6-11, the components of the magneto-optical defect center magnetometer 600 also include a planar arrangement to reduce a z-direction size of the magneto-optical defect center magnetometer 600. The reduced z-direction size may be useful for positioning the magneto-optical defect center magnetometer 600 in a vehicle or other device to control for any vibratory influences and/or space constraints. Moreover, in some implementations, the size and/or weight of the magneto-optical defect center magnetometer 600 may be important. For instance, in aircraft, size and weight may be tightly controlled, so a small z-directional size may permit the magneto-optical defect center magnetometer to be positioned on a bulkhead and/or within a cockpit with minimal space impact. Moreover, the high stiffness and low mass of the top plate 610 and bottom plate 620 limit the weight of the magneto-optical defect center magnetometer 600.

The planar arrangement of the components of the magneto-optical defect center magnetometer 600 may also be useful. The planar arrangement allows for the excitation source, such as the green laser diode 710, and the collection device, such as the one or more photo diodes 718, to be positioned anywhere in the plane, thereby permitting varying configurations for the magneto-optical defect center magnetometer 600 to accommodate space constraints. Further still, the planar configuration also permits multiple excitation sources and/or collection devices to be utilized by the magneto-optical defect center magnetometer 600. As shown in FIGS. 6-11, a primary green laser diode 710 and a flash laser 728 can be used as excitation sources, while two light pipes 734 and photo diodes 718 are utilized for collection devices. Of course additional excitation sources and/or collection devices may be used as well. The planar arrangement of the components of the magneto-optical defect center magnetometer 600 is also beneficial for the mounting of optical components, such as the laser diodes, focusing lenses, light pipes, etc. on the PCB 622 because the planar arrangement limits any z-direction variability such that alignment using the pins and alignment openings positions the optical components in a known position relative to the other components of the magneto-optical defect center magnetometer 600. Further still, the planar arrangement of the components of the magneto-optical defect center magnetometer 600 provides a controlled reference plane for determining the vector of the detected external magnetic field. Still further, the planar arrangement permits usage of the mirror and/or filtering element 732 that can be configured to confine any and/or substantially all of the emitted red light from the magneto-optical defect center element to within a small z-direction area to be directed toward the one or more photo diodes 718. That is, the mirror and/or filtering element 732 can be configured to direct any emitted red wavelength light from the magneto-optical defect center element to within the plane defined by the planar arrangement.

By providing a magneto-optical defect center magnetometer 600 with the excitation source components and collection device components mounted to a single PCB 622, a small form factor magneto-optical defect center vector magnetometer may be provided for a range of applications.

In some implementations, the RF element 716 may be constructed in accordance with the teachings of U.S. Provisional Patent Application No. 62/343,492, filed May 31, 2016, entitled "LAYERED RF COIL FOR MAGNETOMETER", and U.S. Non-Provisional patent application Ser. No. 15/380,691, filed Dec. 15, 2016, entitled "LAYERED RF COIL FOR MAGNETOMETER," the entire contents of which are incorporated by reference herein in their entirety. In some implementations, the one or more light pipes 734 may be constructed in accordance with the teachings of U.S. Provisional Patent Application No. 62/343,746, filed May 31, 2016, entitled "DNV DEVICE INCLUDING LIGHT PIPE WITH OPTICAL COATINGS", U.S. Provisional Patent Application No. 62/343,750, filed May 31, 2016, entitled "DNV DEVICE INCLUDING LIGHT PIPE", the entire contents of each are incorporated by reference herein in their entirety. In some implementations, the mirror and/or filtering element 732 may be constructed in accordance with the teachings of U.S. Provisional Patent Application No. 62/343,758, filed May 31, 2016, entitled "OPTICAL FILTRATION SYSTEM FOR DIAMOND MATERIAL WITH NITROGEN VACANCY CENTERS", the entire contents of each are incorporated by reference herein in its entirety. In some implementations, the magneto-optical defect center magnetometer 600 may be constructed in accordance with the teachings of U.S. Provisional Patent Application No. 62/343,818, filed May 31, 2016, entitled "DIAMOND NITROGEN VACANCY MAGNETOMETER INTEGRATED STRUCTURE", U.S. Provisional Patent Application No. 62/343,600, filed May 31, 2016, entitled "TWO-STAGE OPTICAL DNV EXCITATION", U.S. Non-Provisional patent application Ser. No. 15/382,045, filed Dec. 16, 2016, entitled "TWO-STAGE OPTICAL DNV EXCITATION," U.S. Provisional Patent Application No. 62/343,602, filed May 31, 2016, entitled "SELECTED VOLUME CONTINUOUS ILLUMINATION MAGNETOMETER", the entire contents of each are incorporated by reference herein in their entirety.

Figure 12:
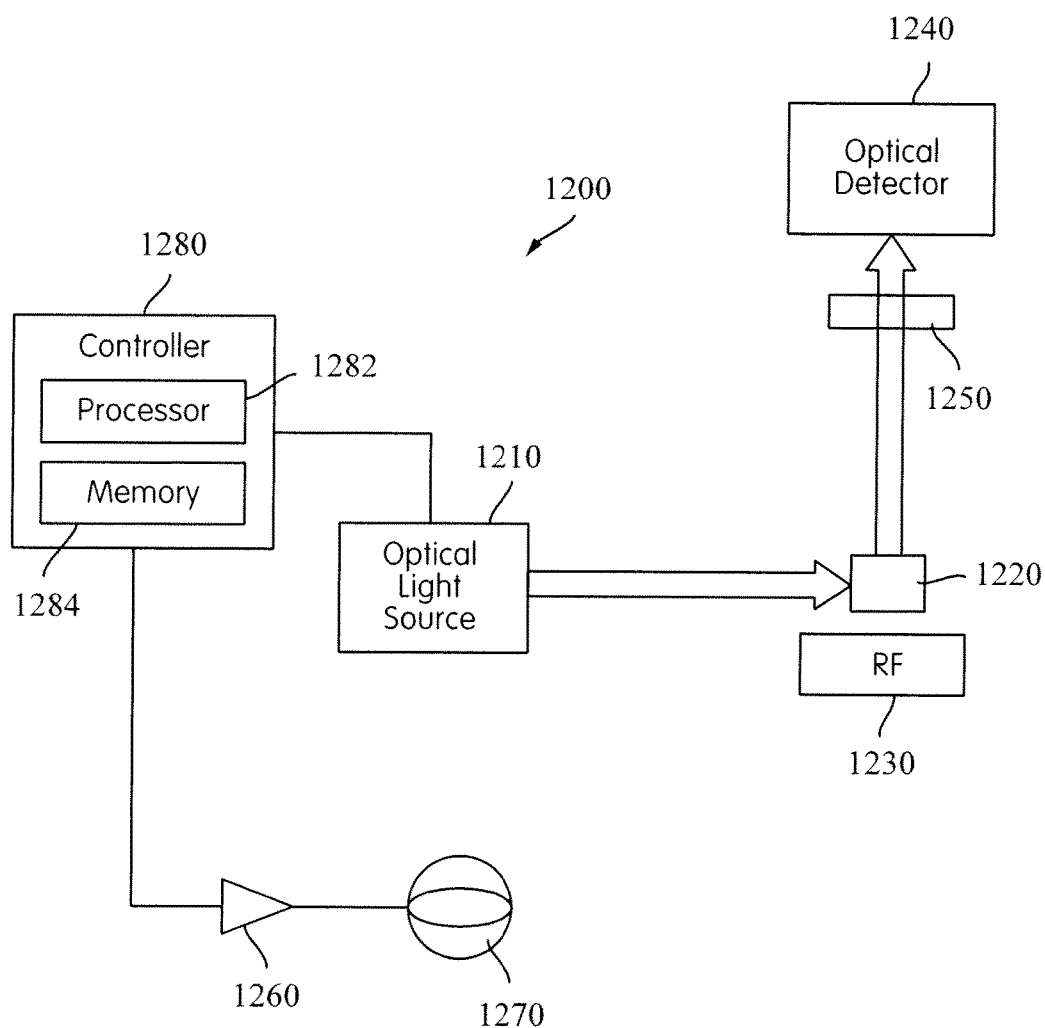
FIG. 12 is a schematic diagram illustrating a magnetic field detection system according to some embodiments.

FIG. 12 is a schematic diagram of a system 1200 for a magnetic field detection system according to some embodiments.

The system 1200 includes an optical light source 1210, which directs optical light to an NV diamond material 1220 with NV centers, or another magneto-optical defect center material with magneto-optical defect centers. An RF excitation source 1230 provides RF radiation to the NV diamond material 1220. The system 1200 may include a magnetic field generator 1270 which generates a magnetic field, which may be detected at the NV diamond material 1220, or the magnetic field generator 1270 may be external to the system 1200. The magnetic field generator 1270 may provide a biasing magnetic field.

The system 1200 further includes a controller 1280 arranged to receive a light detection signal from the optical detector 1240 and to control the optical light source 1210, the RF excitation source 1230, and the magnetic field generator 1270. The controller may be a single controller, or multiple controllers. For a controller including multiple controllers, each of the controllers may perform different functions, such as controlling different components of the system 1200. The magnetic field generator 1270 may be controlled by the controller 1280 via an amplifier 1260, for example.

The RF excitation source 1230 may include a microwave coil or coils, for example. The RF excitation source 1230 may be controlled to emit RF radiation with a photon energy resonant with the transition energy between the ground $m_s=0$ spin state and the $m_s=\pm 1$ spin states as discussed above with respect to FIG. 3, or to emit RF radiation at other nonresonant photon energies.

The controller 1280 is arranged to receive a light detection signal from the optical detector 1240 and to control the optical light source 1210, the RF excitation source 1230, and the magnetic field generator 1270. The controller 1280 may include a processor 1282 and a memory 1284, in order to control the operation of the optical light source 1210, the RF excitation source 1230, and the magnetic field generator 1270. The memory 1284, which may include a nontransitory computer readable medium, may store instructions to allow the operation of the optical light source 1210, the RF excitation source 1230, and the magnetic field generator 1270 to be controlled. That is, the controller 1280 may be programmed to provide control.

Figure 13:
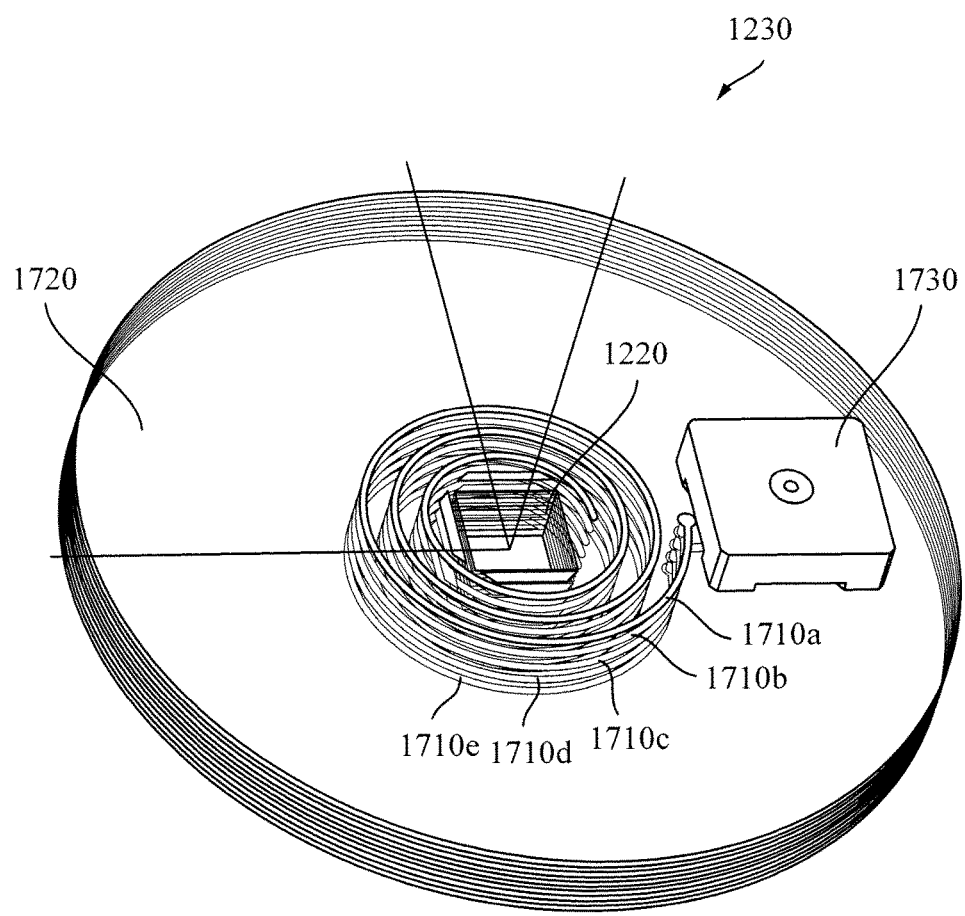
FIG. 13 is a perspective view of a RF excitation source with a plurality of coils according to some embodiments.

FIG. 13 illustrates the RF excitation source 1230 with an arrangement of coils 1710 and an NV diamond material 1220. The RF excitation source 1230 includes a plurality of coils 1710a, 1710b, 1710c, 1710d and 1710e which may be arranged around the NV diamond material 620, where the coils 1710 are in a layered arrangement one above the other. While the number of coils shown in FIG. 13 is five, the number may be more or less than five. The coils 1710 may be formed in a substrate 1720. The coils 1710 may be connected to an RF feed connector 1730 to allow power to be provided to the coils. The coils 1710 may be connected in parallel to the RF feed connector 1730.

While FIG. 13 illustrates the coils 1710 to be arranged around the NV diamond material 1220, the NV diamond material 1220 may have other arrangements relative to the coils 1710. For example, the NV diamond material 1220 may be arranged above or below the coils 1710. The NV diamond material 1220 may be arranged normal to the coils 1710, or at some other angle relative to the coils 1710.

The substrate 1720 may be a printed circuit board (PCB), for example, and the coils 1710 may be layered in the PCB and separated from each other by dielectric material. The coils 1710 may be formed of a conducting material such as a metal, such as copper, for example.

Figure 14A:
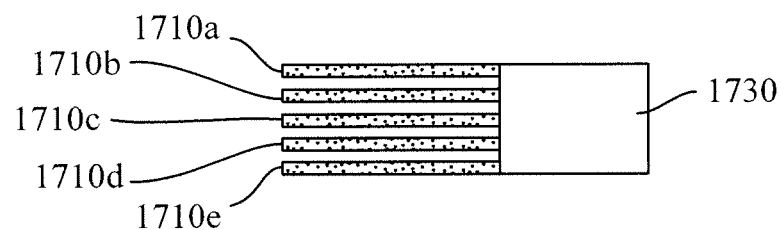
FIG. 14A is a side view of the coils and a RF feed connector of the RF excitation source of FIG. 13.
Figure 14B:
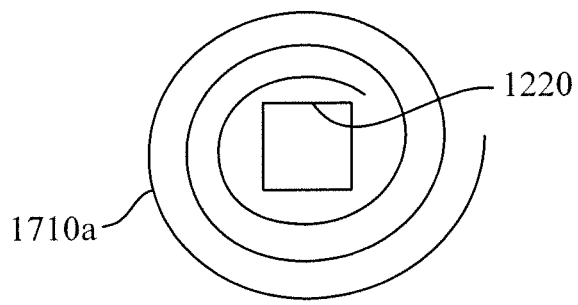
FIG. 14B is a top view of the coils and a RF feed connector of the RF excitation source of FIG. 12.

FIG. 14A is a side view of the coils 1710 and the RF connector 1730. The coils 1710 are spaced from each other in the layered arrangement, and may be spaced by a uniform spacing. The coils may have any shape, such as square or spiral. Preferably, the coils may have a spiral shape, as shown in FIG. 13 and in FIG. 14B, which is a top view of the coils 1710 and the RF connector 1730. In FIG. 14B, only the top coil 1710a can be seen, because the coils 1710b, 1710c, 1710d and 1710e are below the top coil 1710b.

The uniform spacing of the coils 1710 and uniform spacing between the spiral shape coils allow the RF excitation source 1230 to provide a uniform RF field in the NV diamond material 1220 over the frequency range needed for magnetic measurement of the NV diamond material 1220, which may enclosed by the coils 1710. This arrangement provides both uniformity in phase and gain of the RF signal throughout the needed frequency range, and throughout the different regions of the NV diamond material 1220. Further, the layered coils may be operated in a pulsed manner and in this arrangement in order to avoid unnecessary overlap interference. The interference is reduced in pulsed operation of the coils 1710.

Figure 15A:
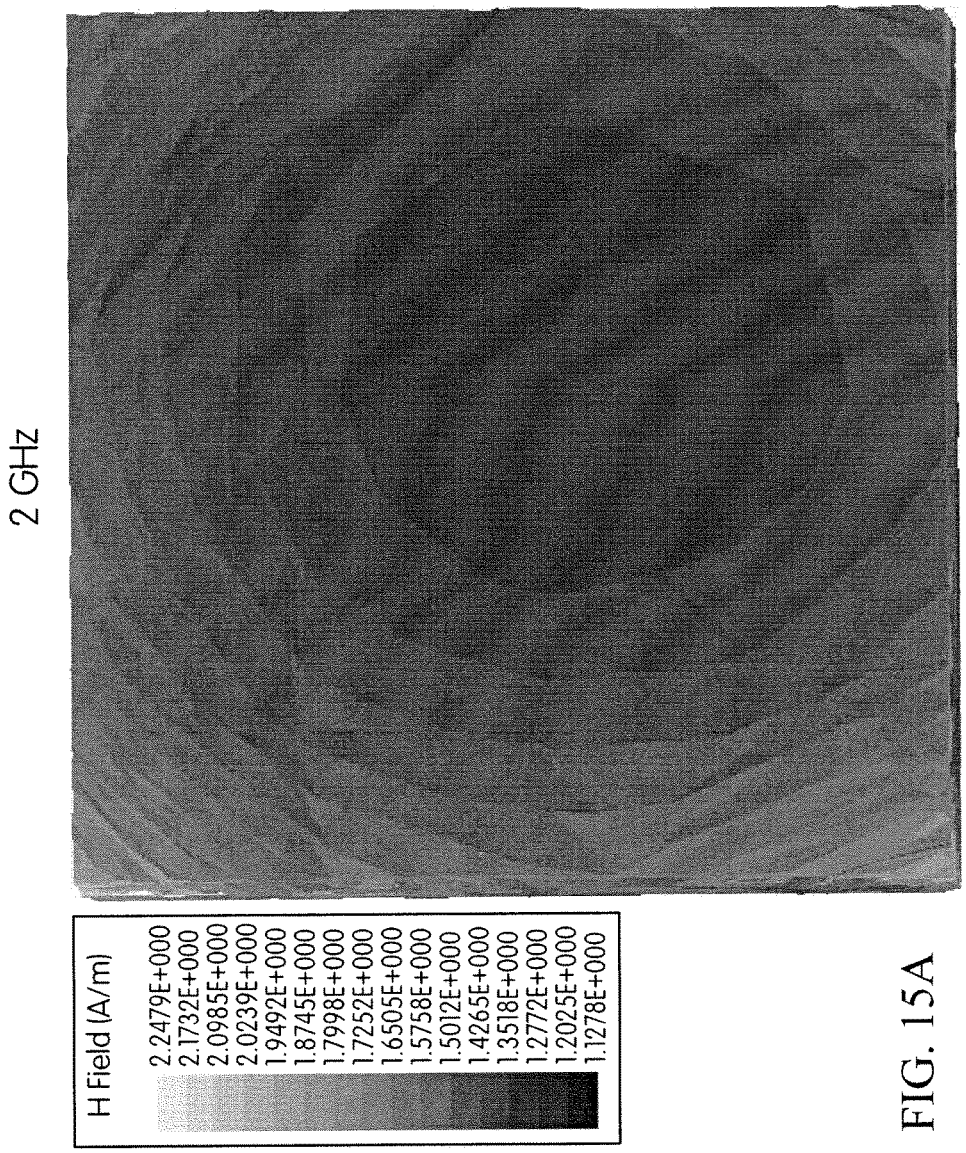
FIG. 15A is a graph illustrating the magnetic field generated by the RF excitation source at 2 GHz in the region of the NV diamond material for a five spiral shaped coil arrangement.
Figure 15B:
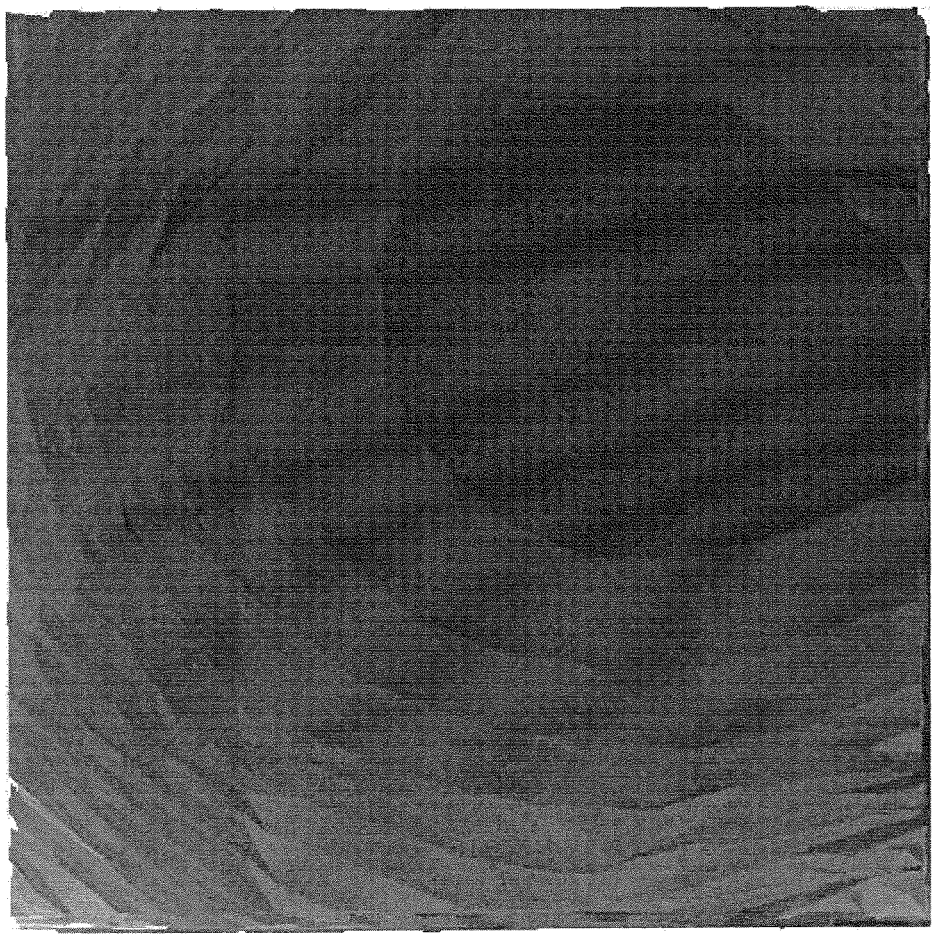
FIG. 15B is a graph illustrating the magnetic field generated by the RF excitation source at 3 GHz in the region of the NV diamond material for the five spiral shaped coil arrangement.
Figure 15C:
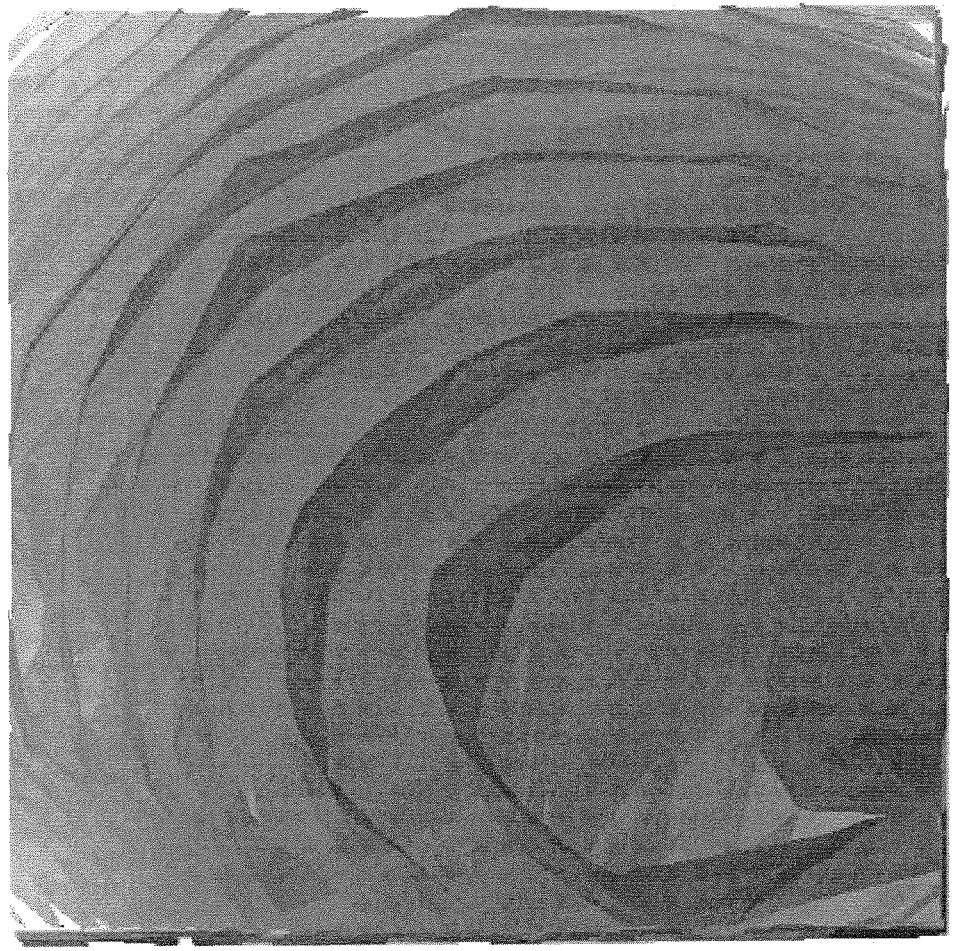
FIG. 15C is a graph illustrating the magnetic field generated by the RF excitation source at 4 GHz in the region of the NV diamond material for the five spiral shaped coil arrangement.

FIGS. 15A, 15B and 15C illustrate the magnetic field H generated by the RF excitation source 1230 in a plane parallel to the plane of the coils 1710 in the region of the NV diamond material 1220 at frequencies of 2 GHz, 3 GHz and 4 GHz, respectively. The arrangement is for a five layer coil with spiral shaped coils. FIG. 16 is a table illustrating the electric field E and magnetic field H generated by the RF excitation source 1230 in the region of the NV diamond material 1220 at frequencies from 2.0 to 4.0 GHz for the five layer coil arrangement with spiral shaped coils. Thus, FIGS. 15A, 15B and 15C illustrate the uniformity of the magnetic field, and FIG. 16 illustrates the uniformity of the electric field E and magnetic field H in the NV diamond material 1220 over the needed frequency range, and throughout the different regions of the NV diamond material 1220.

Figure 17:
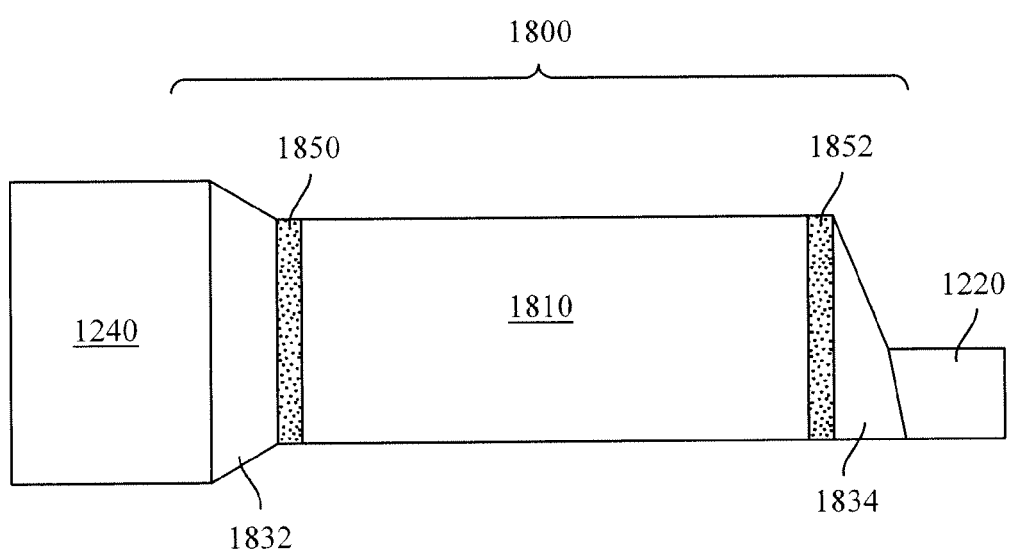
FIG. 17 is a side-view illustrating details of the optical waveguide assembly of the magnetic field sensor system of FIG. 12 according to some embodiments.

FIG. 17 is a schematic illustrating details of an optical waveguide assembly 1800 that transmits light from the NV diamond material 1220 to the optical detector 1240 in some embodiments. The optical waveguide assembly 1800 may include an optical waveguide 1810 and an optical filter 1850 to filter out light in the excitation band (in the green, for example), and to pass light in the red fluorescence band, which in turn is detected by the optical detector 1240.

The optical waveguide 710 may be any appropriate optical waveguide. In some embodiments, the optical waveguide is a light pipe. The light pipe may have any appropriate geometry. In some embodiments, the light pipe may have a circular cross-section, square cross-section, rectangular cross-section, hexagonal cross-section, or octagonal cross-section. A hexagonal cross-section may be preferred, as a light pipe with a hexagonal cross-section exhibits less light loss than a light pipe with a square cross-section and is capable of being mounted with less contact area than a light pipe with a circular cross-section.

The light pipe 1810 may be formed from any appropriate material. In some embodiments, the light pipe may be formed from a borosilicate glass material. The light pipe may be formed of a material capable of transmitting light in the wavelength range of about 350 nm to about 2,200 nm. In some embodiments, the light pipe may be a commercially available light pipe.

The optical filter 1850 may be any appropriate optical filter capable of transmitting red light and reflecting other light, such as green light. In some embodiments, the optical filter 1850 may be a coating applied to an end surface of the light pipe 1810. The coating may be any appropriate anti-reflection coating for red light. In some embodiments, the anti-reflective coating may exhibit greater than 99% transmittance for light in the wavelength range of about 650 nm to about 850 nm. Preferably, the anti-reflective coating may exhibit greater than 99.9% transmittance for light in the wavelength range of about 650 nm to about 850 nm. The optical filter 1850 may be disposed on an end surface of the light pipe 1810 adjacent to the optical detector 1240.

Figure 20:
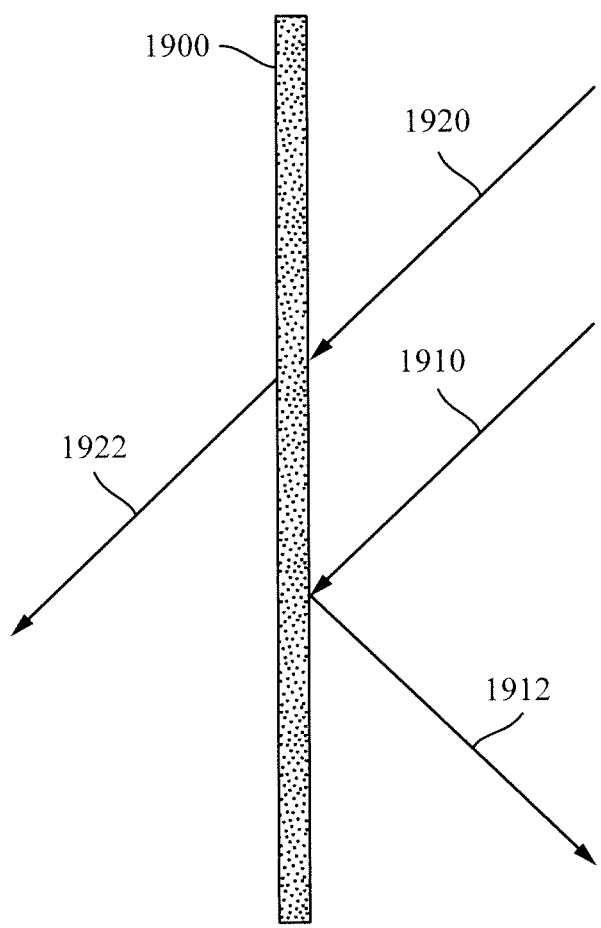
FIG. 20 is a schematic diagram illustrating a dichroic optical filter and the behavior of light interacting therewith according to some embodiments.

In some embodiments, the optical filter 1850 may also be highly reflective for light other than red light, such as green light. Such an optical filter may be a dichroic coating or multiple coatings with the desired cumulative optical properties. The optical filter may exhibit less than about 0.1% transmittance for light with a wavelength of less than about 600 nm. Preferably, the optical filter may exhibit less than about 0.01% transmittance for light with a wavelength of less than about 600 nm. FIG. 20 is a schematic illustrating the behavior of an optical filter 1900 with respect to green light 1910 and red light 1920 according to some embodiments. The optical filter 1900 can be anti-reflective for the red light 1920, resulting in at least some of the red light 1912 transmitted through the optical filter 1900. The optical filter 1900 can be highly reflective for the green light 1910, resulting in green light 1922 being reflected by the optical filter 1900 and at least most of the green light 1922 not transmitted therethrough.

The optical filter 1850 may be a coating formed by any appropriate method. In some embodiments, the optical filter 1850 may be formed by an ion beam sputtering (IBS) process. The coating may be a single-layer coating or a multi-layer coating. The coating may include any appropriate material, such as magnesium fluoride, silica, hafnia, or tantalum pentoxide. The material for the coating may be selected based on the light pipe material and the material which the coating will be in contact with, such as an optical coupling material, to produce the desired optical properties. The coating may have a hardness that approximately matches the hardness of the light pipe. The coating may have a high density, and exhibit good stability with respect to humidity and temperature.

The optical waveguide assembly 1800 may optionally include a second optical filter 1852. The second optical filter 1852 may be a coating disposed on an end surface of the light pipe 1810 adjacent to the diamond material 1220. The second optical filter 1852 may be any of the coatings described above with respect to the optical filter 650. The inclusion of a second optical filter 1852 may improve the performance of the optical waveguide assembly by about 10%, in comparison to an optical waveguide assembly with a single optical filter.

As shown in FIG. 17, the optical waveguide assembly 1800 may include an optical coupling material 1834 disposed between the light pipe 1810 or second optical filter 1852 and the diamond material 1220. An optical coupling material 1832 may also be disposed between the light pipe 1810 or optical filter 1850 and the optical detector 1240. The optical coupling material may be any appropriate optical coupling material, such as a gel or epoxy. In some embodiments, the optical coupling material may be selected to have optical properties, such as an index of refraction, that improves the light transmission between the coupled components. The coupling material may be in the form of a layer formed between the components to be coupled. In some embodiments, the coupling material layer may have a thickness of about 1 microns to about 5 microns. The coupling material may serve to eliminate air gaps between the components to be coupled, increasing the light transmission efficiency. As shown in FIG. 17, the coupling materials 1832 and 1834 may also account for size mismatches between the components to be coupled. The coupling material may be selected such that an efficiency of the optical waveguide assembly is increased by about 10%. The coupling material may produce a light transmission between the components to be coupled that is functionally equivalent to direct contact between the components to be coupled. In some embodiments, an epoxy coupling material may also serve to mount the diamond material to the optical waveguide assembly, such that other supports for the diamond material are not required. In some embodiments, a coupling material may not be necessary where direct contact between the optical filter or light pipe and the optical detector is achieved. Similarly, a coupling material may not be necessary where direct contact between the light pipe or second optical filter and the diamond material is achieved.

Figure 18:
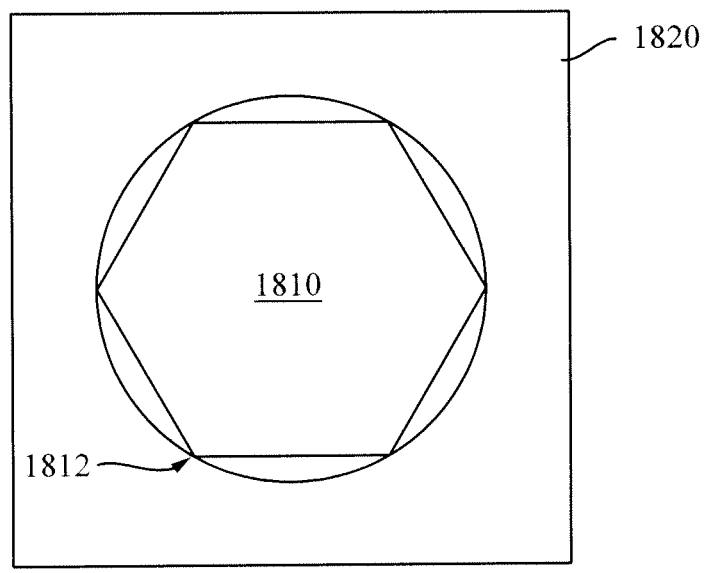
FIG. 18 is a depiction of a cross-section of a light pipe and an associated mount according to some embodiments.

FIG. 18 shows a light pipe 1810 with a hexagonal cross-section and the interaction with a mount 1820 securing the light pipe 1810 within the device in some embodiments. The light pipe 1810 may be mounted such that only the vertices 1812 of the light pipe 1810 contact the mount 1820. Such an arrangement allows the light pipe to be securely and rigidly supported by the mount 1820, while also reducing the contact area between the mount 1820 and the surface of the light pipe 1810. Contact between the light pipe and the mount may result in a reduction in the efficiency of the optical waveguide assembly 1800. As shown in FIG. 18, a mount 1820 with a circular support opening may be successfully employed to support a light pipe 1810 with a hexagonal cross-section.

Figure 19:
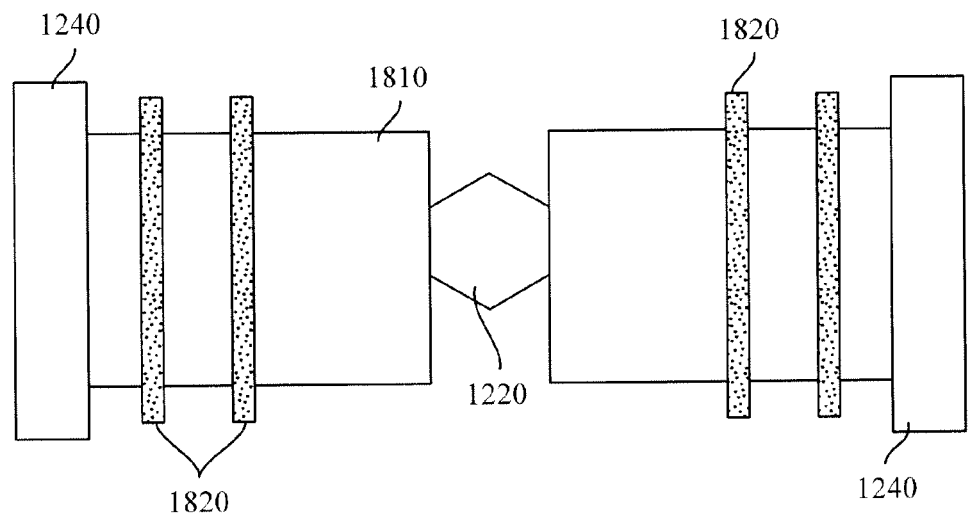
FIG. 19 is a top-down view of an optical waveguide assembly of a magnetic field sensor system according to some embodiments.

FIG. 19 shows a top down schematic of an arrangement of optical waveguide assemblies according to some embodiments. The optical filters and optical coupling materials are not shown in FIG. 19 for the sake of clarity. As shown in FIG. 19, more than one optical waveguide assembly may be included in the magnetic sensor system, such as two or more optical waveguide assemblies. The inclusion of more than one optical waveguide assemblies allows more than one optical detector 1240 to be included in the magnetic sensor device, increasing the amount of light collected and measured by the optical detectors 1240. The inclusion of additional optical detectors 1240 also increases the amount of noise in the system, which may negatively impact the sensitivity or accuracy of the system. The use of two optical waveguide assemblies may provide a compromise between increased light collection and increased noise. Each optical waveguide assembly in the magnetic sensor system may be associated with a different optical detector, but the same diamond material.

The light pipe 1810 may be mounted to the magnetic sensor system by at least one mount 1820. In some embodiments, two mounts 1820 may support each light pipe 1810 in the magnetic sensor system. The light pipe may be mounted to the device rigidly, such that the alignment of the light pipe 1810, the optical detector 1240, and the diamond material 1220 is maintained during operation of the system. The mounting of the light pipe to the magnetic sensor system may be sufficiently rigid to prevent a mechanical response of the light pipe in the region that would affect the measurement of light by the optical detector.

The light pipe can be selected to have an appropriate aperture size. The aperture of the light pipe can be selected to be matched to or smaller than the optical detector. This size relationship allows the optical detector to capture the highest possible percentage of the light emitted by the light pipe. The aperture of the light pipe can be also selected to be larger than the surface of the diamond material to which it is coupled. This size relationship allows the light pipe to capture the highest possible percentage of light emitted by the diamond material. In some embodiments, the light pipe may have an aperture of about 4 mm. In some other embodiments, the light pipe may have an aperture of about 2 mm. In some embodiments, the light pipe may have an aperture of 4 mm, and the diamond material may have a coupled surface with a height of 0.6 mm and a length of 2 mm, or less. The light pipe may have any appropriate length, such as about 25 mm.

As shown in FIG. 19, the light pipe can be positioned such that the end surface of the light pipe adjacent the diamond material is parallel, or substantially parallel, to the associated surface of the diamond material. This arrangement allows the light pipe to capture an increased amount of the light emitted by the diamond material. The alignment of the surfaces of the light pipe and the diamond material ensures that a maximum amount of the light emitted by the diamond material will intersect the end surface of the light pipe, thereby being captured by the light pipe.

Figure 21:
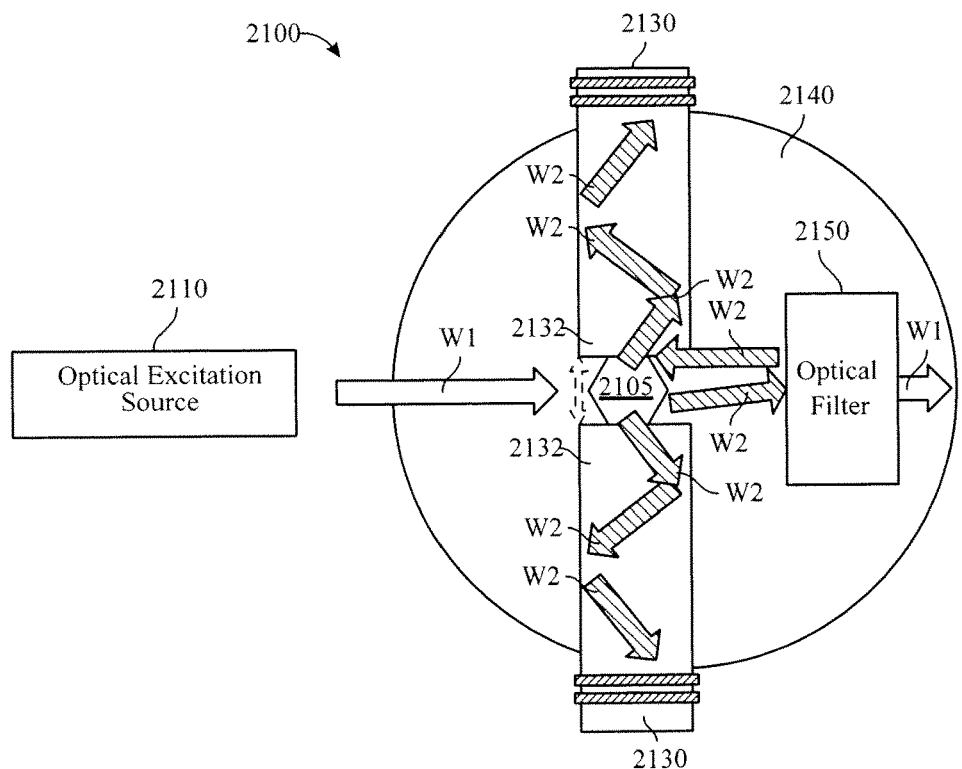
FIG. 21 is a schematic block diagram of some embodiments of an optical filtration system.

With reference to FIG. 21, some embodiments of an optical filtration system 2100 is illustrated. In these embodiments, the optical filtration system 2100 includes an optical excitation source 2110, a vacancy material 2105 with vacancy centers, a RF excitation source 2120, optical guide 2130, and a optical filter 2150.

The optical filter 2150 is configured to provide at least a second portion of light corresponding to a second wavelength W2 to a plurality of optical collectors 2130 as described herein.

The optical excitation source 2110 may be a laser or a light emitting diode. The optical excitation source may be configured to generate light corresponding to a first wavelength W1. For example, the optical excitation source 2110 may emit light corresponding to green.

The vacancy material 2105 may be configured to receive optical excitation based, at least in part, on the generation of light corresponding to a first wavelength W1. In some further embodiments, the NV diamond material 2105 may be configured to receive radio frequency (RF) excitation provided via the RF excitation source as described herein above.

In turn, the vacancy material 2105 may be configured to generate light corresponding to a second wavelength W2 (e.g., a wavelength corresponding to red) responsive to the RF excitation and the optical excitation received. In this regard, the optical excitation source 2110 induces fluorescence by the vacancy material 2105 corresponding to the second wavelength W2. The inducement of fluorescence causes an electronic transition from the excited state to the ground state. The optical excitation source 2110, in addition to exciting fluorescence in the NV diamond material 2105, also serves to reset the population of the ms=0 spin state of the ground state $^3A_2$ to a maximum polarization, or other desired polarization.

Figure 22:
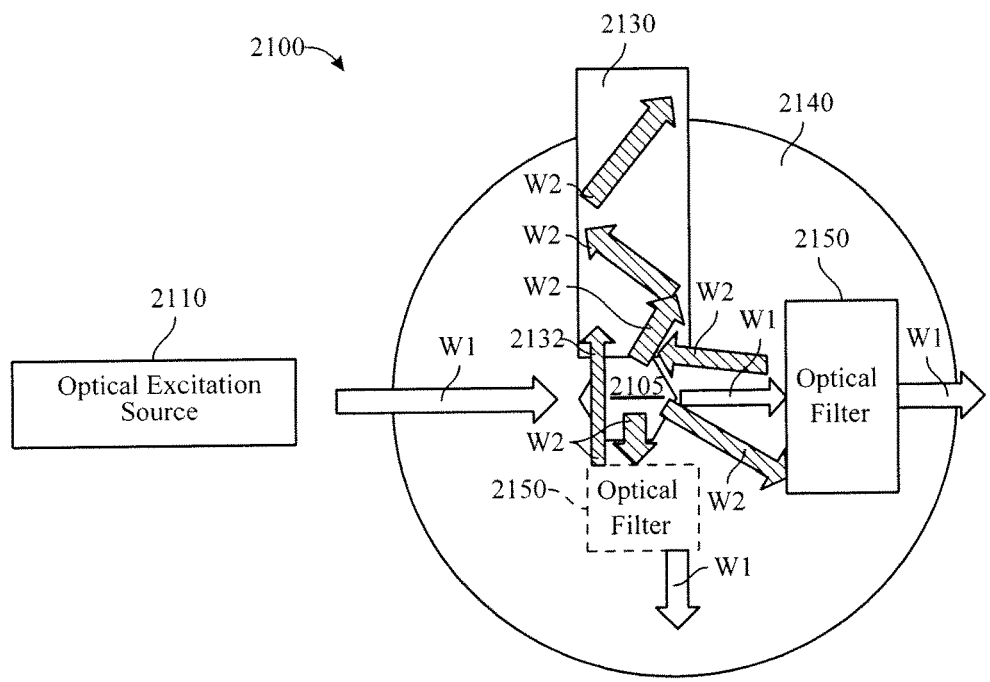
FIG. 22 is a schematic block diagram of some embodiments of an optical filtration system.

The optical filtration system 2100 includes a plurality of optical collectors 2130 configured to receive at least a first portion of light corresponding to the second wavelength W2. The optical collectors may take the form of light pipes, light tubes, lenses, optical fibers, optical waveguides, etc. For example, as the vacancy material 2105 generates light corresponding to the second wavelength W2 (e.g., red light), a first portion of the light corresponding to the second wavelength W2 may enter or is otherwise received by the optical collectors 2130. The light corresponding to the wavelength W2 may be received by the receiving ends 2132 of each respective optical collector 2130. In some embodiments, the receiving ends 2132 may be disposed proximate to (e.g., adjacent to or otherwise near) the vacancy material 2105. Although a plurality of optical collectors 2130 is depicted, in some embodiments, one optical collector 2130 (as depicted in FIG. 22) may be configured to receive at least a first portion of light corresponding to the second wavelength W2.

As illustrated in FIG. 21, the NV diamond material 2105 is disposed between the receiving ends 2132 such that the optical collectors 2130 are configured to form a gap G. A second portion of the light corresponding to the wavelength W2 may be directed beyond the gap G and/or the optical collectors 2130. For example, the light directed beyond the gap G may not enter or otherwise be received by the optical collectors 2130. The gap G may include an adhesive material such as a gel or an epoxy. Although a gap G is depicted, the gap G may be filled or otherwise inexistent such that the NV diamond material 2105 may generate light without the gap G as described herein.

The optical filtration system 2100 further includes the optical filter 2150. The optical filter 2150 is configured to provide at least a second portion of light corresponding to the second wavelength W2 to the plurality of optical collectors 2130. As used herein, the term "optical filter" may be used to refer to a filter configured to transmit (e.g. pass) light corresponding to one or more predetermined wavelengths (e.g., a first wavelength corresponding to green) while reflecting light corresponding to other predetermined wavelengths (e.g., a second wavelength corresponding to red). In some embodiments, the optical filter 2150 may take the form of a dichroic filter, interference filter, thin-film filter, dichroic mirror, dichroic reflector, or a combination thereof. The optical filter 2150 (e.g., a dichroic filter) may be configured to reflect light corresponding to the second wavelength W2 (e.g., light in the red fluorescence band) from the vacancy material 2105 which, in turn, is received by the optical collectors 2130. For example, the optical filter 2150 may reflect the light directed beyond the gap G to the optical collectors 2130 that would otherwise not enter or be received by the optical collectors 2130.

Alternatively or additionally, light corresponding to the first wavelength W1 from the vacancy material 2105 may be directed through the optical filter 2150 to filter out the light corresponding to the first wavelength W1 (e.g., in the green fluorescence band). Although a single optical filter 2150 is depicted, in some embodiments, a plurality of optical filters 2150 (as depicted in FIG. 22) may be configured to provide at least a second portion of light corresponding to a second wavelength W2 to one or more optical collectors 2130.

In some embodiments, the optical filter 2150 includes an optical coating (e.g., an anti-reflection coating, high reflective coating, filter coating, beamsplitter coating, etc.) configured to facilitate transmission of light corresponding to the first wavelength W1 (e.g., light corresponding to green) through the optical filter 2150. The optical coating may include at least one of a soft coating (e.g., one or more layers of thin film) or a hard coating. The optical coating may be made of a material such as zinc sulfide, cryolyte, silver, and/or any other like suitable material, or a combination thereof.

The optical coating (e.g., the anti-reflective coating) is further configured to facilitate the provision of the light corresponding to the second wavelength W2 to the optical collectors 2130. For example, the optical coating facilitates the reflection of the light corresponding to the second wavelength W2 from the vacancy material 2105 to the optical collectors 2130.

Figure 23:
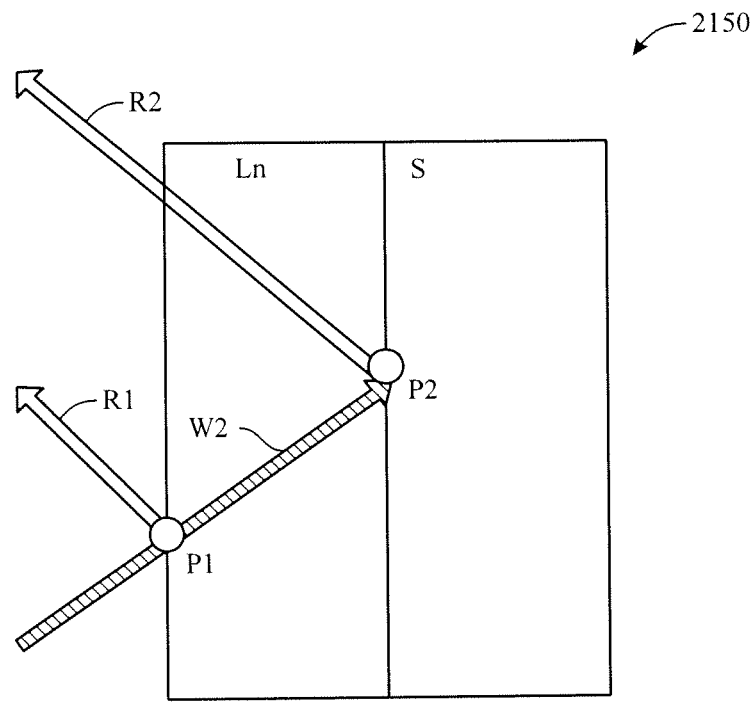
FIG. 23 is a diagram of an optical filter according to some embodiments.

As illustrated in FIG. 23, the optical coating may include a substrate S and one or more layers Ln configured to at least one of transmit or reflect light according to at least one refractive index which describes how light propagates through the optical filter 2150. In this regard, the phase shift between the light corresponding to the second wavelength W2 reflected, for example, at the first and second points P1, P2 of the layer Ln is 180°. In turn, the reflections R1, R2 (e.g., the reflected rays) are cancelled responsive to interference such as, but not limited to, destructive interference. Advantageously, the optical coating increases transmission, efficiency by which the light corresponding to the second wavelength W2 is received by the optical collectors 2130 and resists environmental damage to the optical filter 2150.

With reference back to FIG. 21, the optical filter 2150 may be disposed at least one of above, beneath, behind, or in front of the vacancy material 2105 to receive and, in turn, provide the light corresponding to the second wavelength W2 (e.g., light in the red fluorescence band) to the optical collectors 2130. As illustrated, the optical filter 2150 is disposed behind the NV diamond material 2105 such that the optical filter 2150 reflects light corresponding to the second wavelength W2 from the vacancy material 2105. In some embodiments, the optical filter 2150 may be configured to enclose or otherwise surround the vacancy material 2105. The enclosing of the vacancy material 2105 increases the reflection of light corresponding to the second wavelength W2 from the vacancy material 2105 to the optical collectors 2130.

In some embodiments, the optical filter 2150 is disposed proximate to the plurality of optical collectors 2130. The optical filter 2150 may be disposed within a predetermined distance to the optical collectors 2130. For example, the optical filter 2150 may be disposed next to the optical collectors 2130 as depicted. The optical filter 2150 may be disposed at least one of above, beneath, behind, or in front of the plurality of optical collectors 2130. As depicted, the optical filter 2150 is disposed behind the plurality of optical collectors 2130. Advantageously, disposing the optical filter 2150 behind the plurality of optical collectors 2130 facilitates the removal of light corresponding to the first wavelength W1 (e.g., light corresponding to green) by the optical filter 2150 which reduces noise and/or other errors introduced by W1.

Figure 24:
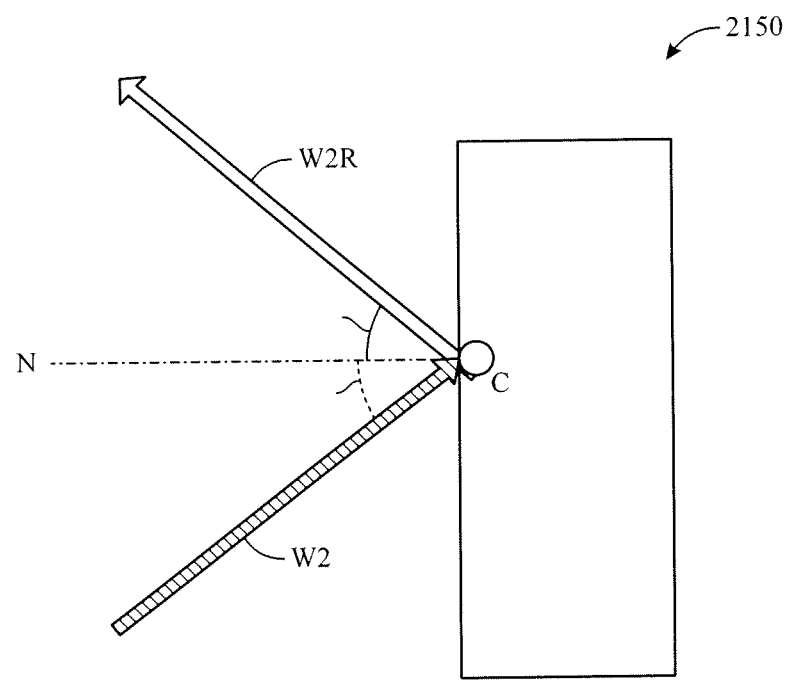
FIG. 24 is a diagram of an optical filter according to some embodiments.

In further embodiments, a predetermined dimension (e.g., length, width, height, etc.) corresponding to the optical filter 2150 may be configured to extend beyond a predetermined dimension (e.g., length, width, height, etc.) corresponding to the gap G and/or the optical collectors 2130. For example, the width of the optical filter 2150 may be configured to be greater than the width of the gap G to compensate for over tolerances in manufacturing such that the optical filter 2150 covers the gap G. As the light corresponding to the second wavelength W2 makes contact C with or otherwise hits the optical filter 2150, the light W2 is reflected (as illustrated in FIG. 24) from the optical filter 2150 to the optical collectors 2130. The light ray W2 R is reflected at an angle of incidence $\alpha$ and an angle of reflection $\beta$ as depicted across the normal N. The angle of incidence may equal the angle of reflection. Each respective angle may measure between 0 degrees and 180 degrees based on one or more refractive indices corresponding to the optical filter 2150. Alternatively or additionally, the height of the optical filter 2150 may be configured to be greater than the height of the optical collectors 2130 to compensate for over tolerances in manufacturing such that the optical filter 2150 receives light (e.g., light corresponding to the second wavelength W2) directed beyond the optical collectors 2130. In turn, the optical filter 2150 reflects or otherwise provides the light corresponding to the second wavelength W2 to the optical collectors 2130.

Figure 25:
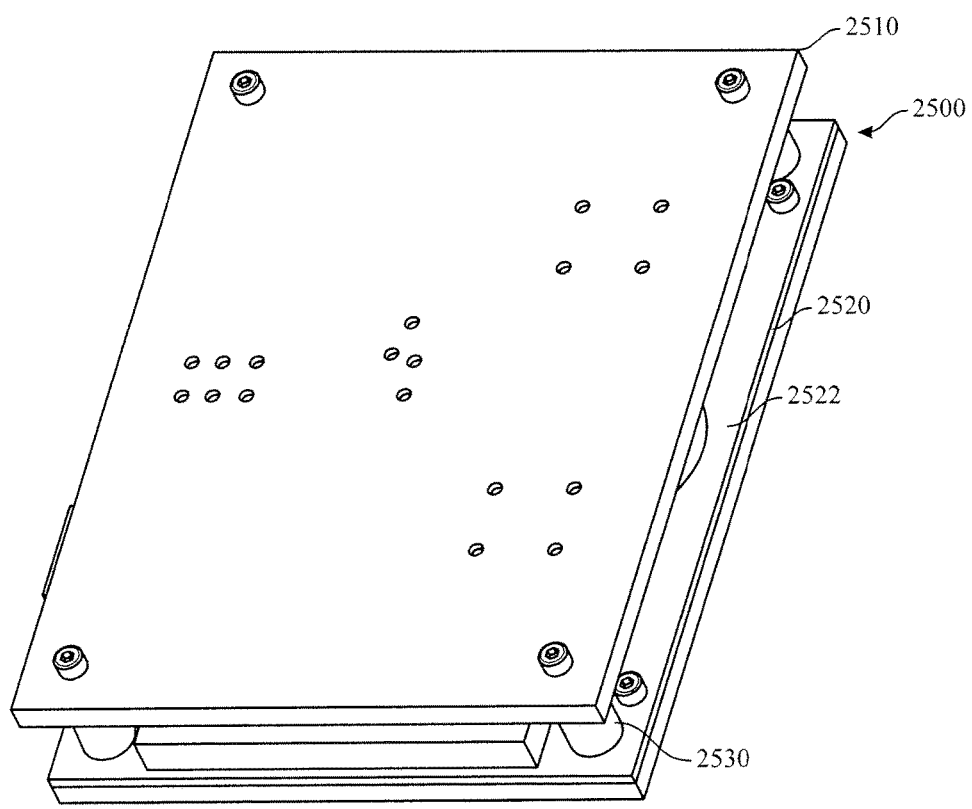
FIG. 25 is an illustrative perspective view depicting some embodiments of a magneto-optical defect center magnetometer.

Referring generally to FIG. 25, a magneto-optical defect center magnetometer 2500 may be provided that includes a top plate 2510 and a bottom plate 2520. The bottom plate 2520 may include a printed circuit board (PCB) 2522 that is configured to mount the components of the magneto-optical defect center magnetometer 2500 thereto. The top plate 2510 and bottom plate 2520 may be formed of a material with a high stiffness and a low mass, such as stainless steel, titanium, aluminum, carbon fiber, a composite material, etc. The high stiffness of the top plate 2510 and bottom plate 2520 is such that any vibration modes occur outside of the range of frequencies that may negatively affect the magneto-optical defect center magnetometer 2500 sensor performance. The top plate 2510, bottom plate 2520, and PCB 2522 includes alignment holes into which pins for one or more components of the magneto-optical defect center magnetometer 2500 may be inserted to align the one or more components and, when the top plate and bottom plate 2520 are pressed together, the pins lock the components in place to maintain alignment of the one or more components after assembly of the magneto-optical defect center magnetometer 2500.

Figure 26:
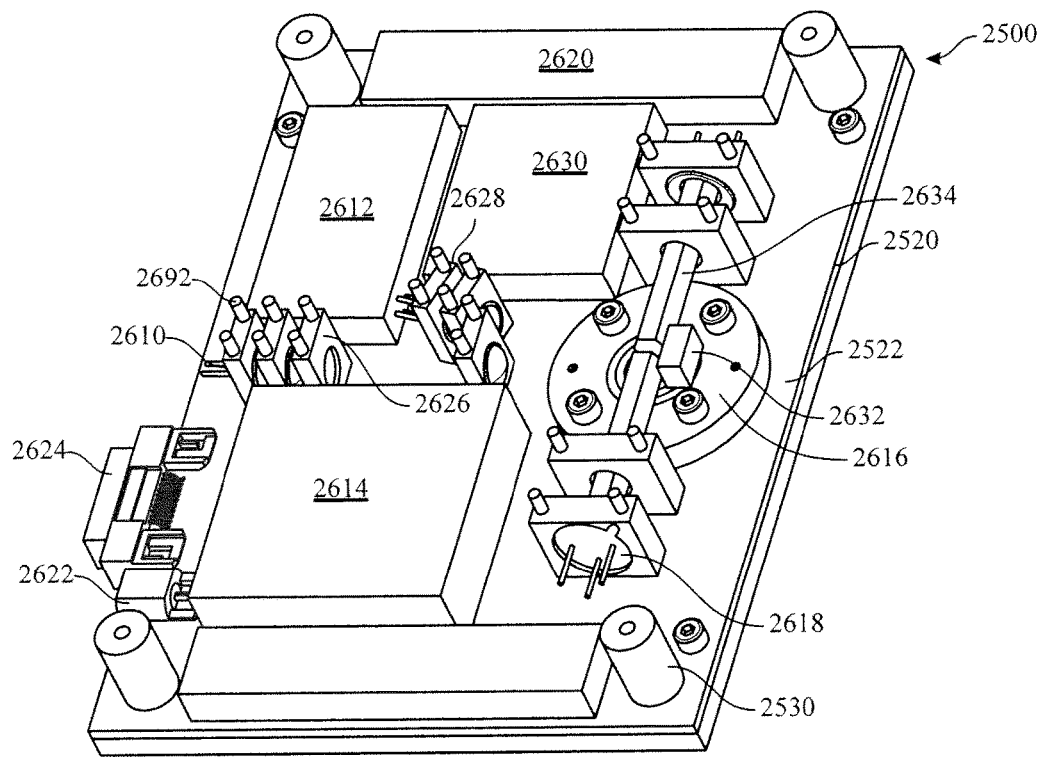
FIG. 26 is an illustrative perspective view of the magneto-optical defect center magnetometer of FIG. 25 with a top plate removed.
Figure 27:
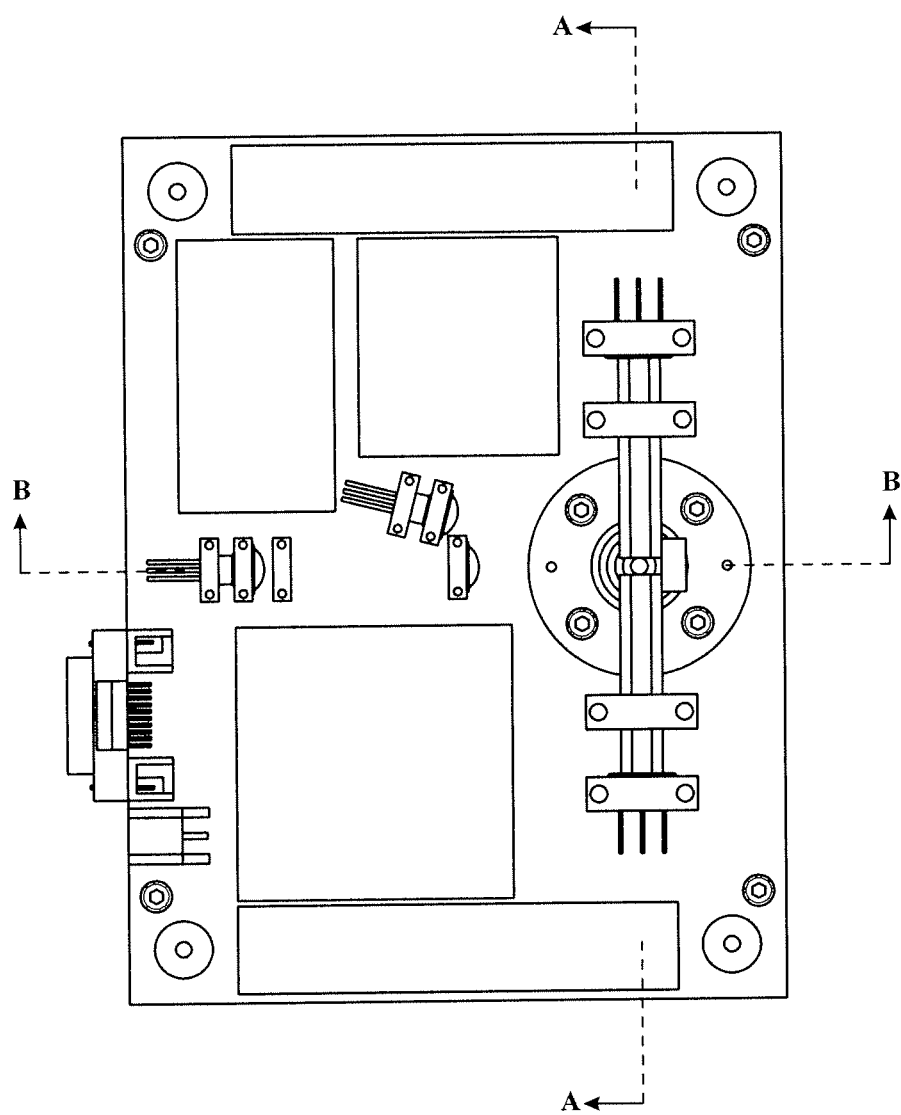
FIG. 27 is an illustrative top view depicting the magneto-optical defect center magnetometer of FIG. 25 with the top plate removed.
Figure 28:
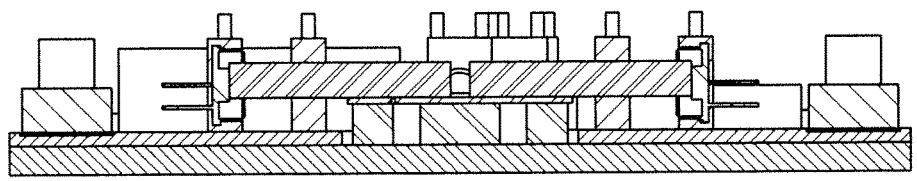
FIG. 28 is an illustrative cross-sectional view taken along line A-A and depicting the magneto-optical defect center magnetometer of FIG. 25 with the top plate removed.
Figure 29:
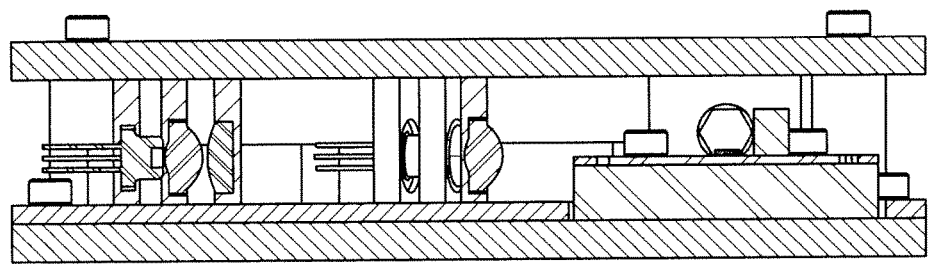
FIG. 29 is an illustrative cross-sectional view taken along line B-B and depicting the magneto-optical defect center magnetometer of FIG. 25 with the top plate attached.
Figure 30:
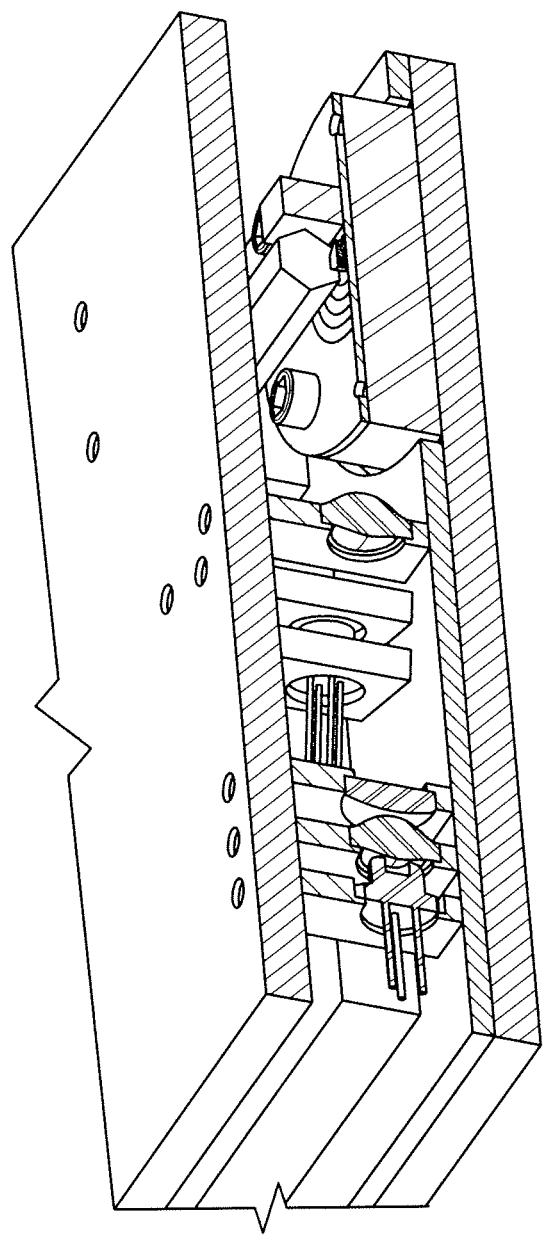
FIG. 30 is an illustrative perspective cross-sectional view taken along line B-B and depicting the magneto-optical defect center magnetometer of FIG. 25 with the top plate attached.

As shown in FIG. 26, the magneto-optical defect center magnetometer 2500 has several components mounted between top plate 2510, the bottom plate 2520, and the PCB 2522. The components of the magneto-optical defect center magnetometer 2500 include a green laser diode 2610, laser diode circuitry 2612, a magneto-optical defect center element, such as a diamond having nitrogen vacancies (DNV), RF amplifier circuitry 2614, an RF element 2616, one or more photo diodes 2618, and photo diode circuitry 2620. In operation, the green laser diode 2610 emits green wavelength light toward the magneto-optical defect center element based on a control signal from the laser diode circuitry 2612. The RF amplifier circuitry 2614 receives an RF input signal via an RF connector 2622. In some implementations, the RF signal is generated by a separate controller, such as an external RF wave form generator circuit. In other implementations, the RF waveform generator may be included with the magneto-optical defect center magnetometer 2500. The RF amplifier circuitry 2614 uses the RF input signal to control the RF element 2616. The RF element 2616 may include a microwave coil or coils. The RF element 2616 emits RF radiation to control the spin of the centers of the magneto-optical defect center element to be aligned along a single direction, such as prior to a measurement by the magneto-optical defect center magnetometer 2500. The magneto-optical defect center element, when excited by the green laser light, emits red wavelength based on external magnet fields and the emitted red light is detected by the one or more photo diodes 2618. The detected red light by the photo diodes 2618 may be processed by the photo diode circuitry 220 and/or may be outputted to an external circuit for processing. Based on the detected red light, the magneto-optical defect center magnetometer 2500 can detect the directionality and intensity (e.g., vector) of the external magnetic field. Such a vector magnetometer may be used to detect other objects that generate or distort magnetic fields. Power for the components and/or circuits of the magneto-optical defect center magnetometer 2500 and data transmission to and/or from the magneto-optical defect center magnetometer 2500 may be provided via a digital signal and power connector 2624.

In some implementations, the magneto-optical defect center magnetometer 2500 may include several other components to be mounted via the top plate 2510, bottom plate 2520, and PCB 2522. Such components may include one or more focusing lenses 2626, a flash laser 2628 and/or flash laser focusing lenses, excitation driver circuitry 2630, a mirror and/or filtering element 2632, and/or one or more light pipes 2634. The focusing lenses 2626 may focus the emitted green wavelength light from the green laser diode 2610 towards the magneto-optical defect center element. The flash laser 2628 and/or flash laser focusing lenses may provide additional excitation green wavelength light to the magneto-optical defect center element, and the excitation driver circuitry 2630 may control the operation of the flash laser 2628. The mirror and/or filtering element 2632 may be an element that is reflective for red wavelength light, but permits green wavelength light to pass through. In some implementations, the mirror and/or filtering element 2632 may be applied to the magneto-optical defect center element, such as a coating, to reflect red wavelength light towards the photo diodes 2618. In other implementations, the mirror and/or filtering element 2632 may be a separate component that substantially surrounds or encases the magneto-optical defect center element. The one or more light pipes 2634 transports red wavelength light emitted from the magneto-optical defect center element to the one or more photo diodes 2618 such that the one or more photo diodes 2618 may be positioned remote from the magneto-optical defect center element. Additional description may include the applications incorporated by reference.

As can be seen in FIG. 26, the elements of the magneto-optical defect center magnetometer 2500 need to be aligned such that the emitted green light from the green laser diode 2610 is directed towards the magneto-optical defect center element and the emitted red wavelength light from the magneto-optical defect center element is directed toward the one or more photo diodes 2618 to be detected. Thus, the various elements must be mounted to the magneto-optical defect center magnetometer 2500 in a manner that aligns and holds the elements in position both during assembly and operation. In some implementations, the elements to be aligned include the green laser diode 2610, any focusing lenses 2626, any flash laser 2628, the RF element 2616, any mirror and/or filtering element 2632, any support elements for any light pipes 2634, and the one or more photo diodes 2618. In some implementations, a two-point orientation system may be implemented to align and secure the elements to be mounted for the magneto-optical defect center magnetometer 2500. That is, the components to be aligned and mounted, or a support or mounting element for each component, includes two points to be aligned relative to the top plate 2510 and two points to be aligned relative to the bottom plate 2520 and PCB 2522. When the two points are aligned and secured relative to the top plate 2510, then the component and/or support or mounting element is rotationally and translationally fixed relative to the top plate 2510. Similarly, when the two points are aligned and secured relative to the bottom plate 2520 and PCB 2522, then the component and/or support or mounting element is rotationally and translationally fixed relative to the bottom plate 2520 and PCB 2522. When the component and/or support or mounting element is positioned between the top plate 2510 and the bottom plate 2520 and PCB 2522, then the component and/or support or mounting element is secured such that the component and/or support or mounting element has a fixed orientation and position for the magneto-optical defect center magnetometer 2500. In some implementations, the two-point orientation system can include two separate components, such as two top pins and two bottom pins. In other implementations, the two-point orientation system may include two surfaces of a single component, such as two different surfaces of a single top pin and single bottom pin. In still other implementations, additional alignment and/or securing points may be used, such as three pins and/or surfaces, four pins and/or surfaces, etc.

Figure 31:
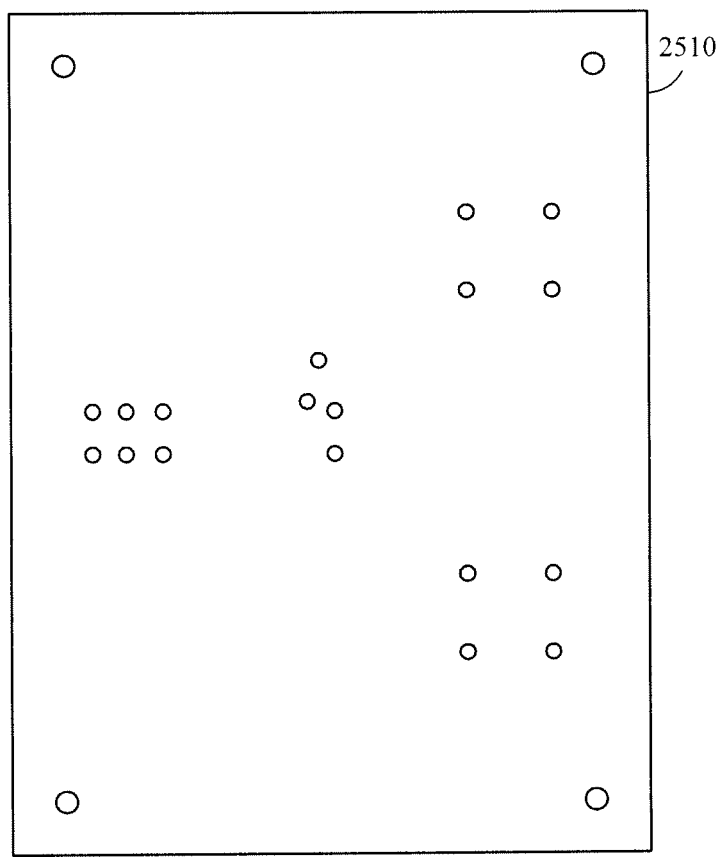
FIG. 31 is an illustrative top view depicting the top plate of the magneto-optical defect center magnetometer of FIG. 25.

In the implementations shown, the top plate 2510, bottom plate 2520, and PCB 2522 are manufactured and/or machined to include one or more alignment openings, such as alignment openings of the top plate 2510 shown in FIG. 31. In some implementations, the alignment openings may be circular, triangular, square, ovular, ellipsoidal, pentagonal, hexagonal, star shaped, etc. Two or more alignment openings may be provided for the two-point orientation system for each component, such as two circular alignment openings. In other implementations, the alignment openings may be asymmetric openings such that a corresponding pin can only be inserted in a particular orientation. For instance, the alignment openings may be semicircular, etc. The asymmetrical alignment openings may provide two surfaces for the two-point orientation system to align and secure each component and/or a support or mounting element for each component.

Figure 32:
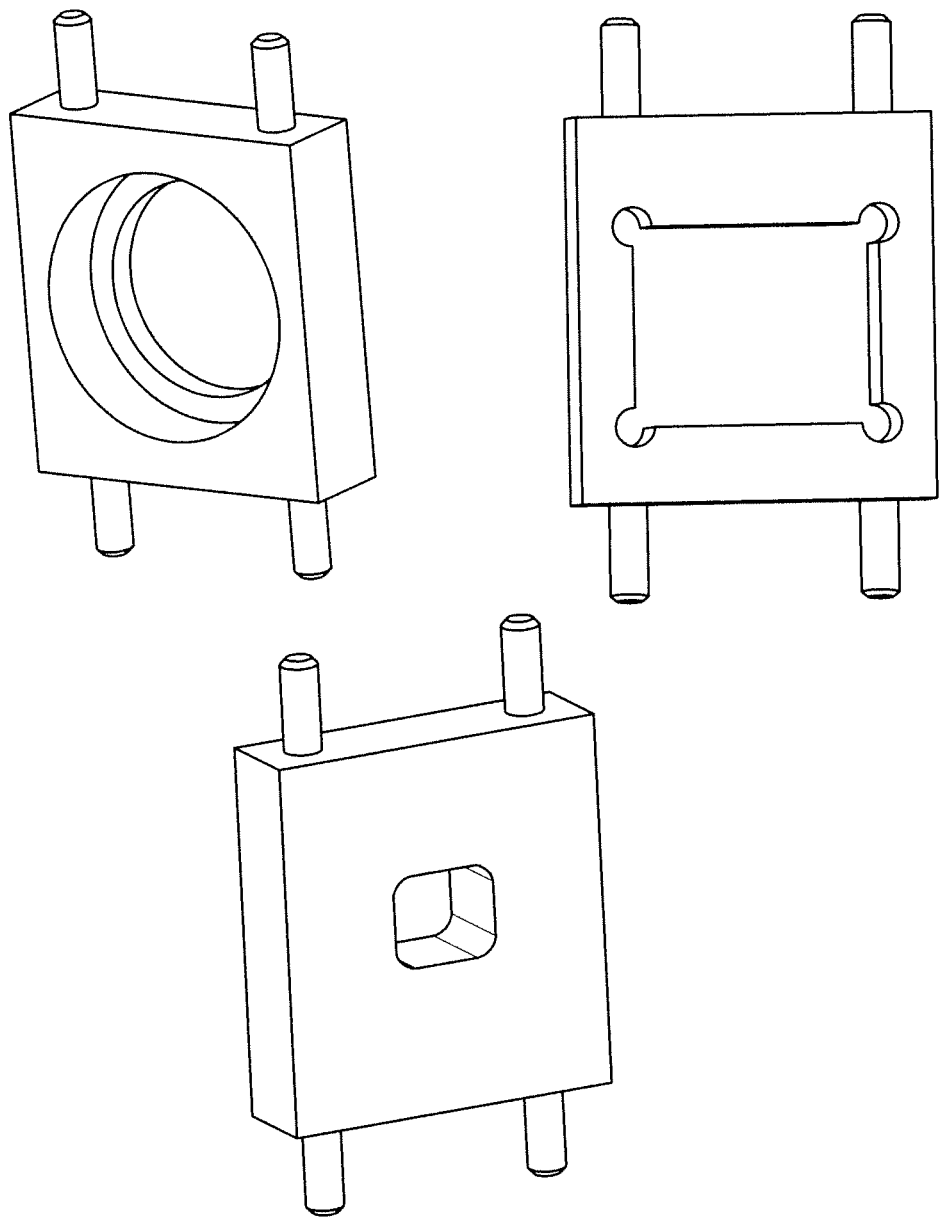
FIG. 32 is an illustrative perspective view of support elements for one or more components of the magneto-optical defect center magnetometer of FIG. 25.

Each support or mounting element, such as the supports or mounting elements shown in FIG. 32, for each of the components to be aligned for the magneto-optical defect center magnetometer 2500 may include one or more corresponding pins, such as pin 2692 shown in FIG. 26. In some implementations, the one or more corresponding pins may have an asymmetrical cross-sectional geometry to provide two surfaces for the two-point orientation system to align the components relative to the top plate 2510, bottom plate 2520, and PCB 2522. In some implementations, each support or mounting element for each component of the DNV magnetometer 2500 may include two top pins and two bottom pins to align each component relative to the top plate 2510, bottom plate 2520, and PCB 2522. The two top pins and two bottom pins may further limit misalignment. In some implementations, the support or mounting elements may be formed of a plastic, aluminum, titanium, stainless steel, carbon fiber, a composite material, etc. In some implementations, the pins of the support or mounting elements may be configured to be press-fit pins such that the pins compress and form an interference fit with the corresponding alignment openings of the top plate 2510, bottom plate 2520, and PCB 2522. In some implementations, the components may be affixed, such as by an adhesive, mechanical attachment, etc., to a corresponding support or mounting element. For instance, as shown in FIG. 32, support or mounting elements for a laser diode and/or focusing lens, photo diode, and light pipe are shown.

When the magneto-optical defect center magnetometer 2500 is assembled, a bottom pin for each component is inserted through an alignment opening of the PCB 2522 and bottom plate 2520 to initially mount the component. The top plate 2510 may then be aligned with the top pins for each component and the top plate 2510 and bottom plate 2520 are pressed together to secure and maintain alignment of the components of the magneto-optical defect center magnetometer 2500. In some implementations, the pins may be soldered to the top plate 2510 and/or bottom plate 2520 to fix the components in position. In some implementations, standoffs 2530 are provided to mechanically couple the top plate 2510 to the bottom plate 2520 and PCB 2522. The standoffs 2530 may be formed with the bottom plate 2520 and extend through the PCB 2522 and/or may be separate components attached to the bottom plate 2520 and PCB 2522. In the implementation shown, the standoffs 2530 include threading for a screw, bolt, or other attachment component to be inserted through an opening of the top plate 2510 and secured to the standoff 2530. In other implementations, the standoffs 2530 may be welded or otherwise secured to the top plate 2510.

By providing alignment pins for the various components of the magneto-optical defect center magnetometer 2500, the components can be secured in a preset position during assembly and operation of the magneto-optical defect center magnetometer 2500. Moreover, by providing a high stiffness and low mass material for the top plate 2510 and bottom plate 2520, any low frequency vibrations can be transmitted through the magneto-optical defect center magnetometer 2500 without affecting the higher frequency operations of the magneto-optical defect center magnetometer 2500.

Referring generally to FIGS. 25-32, the components of the magneto-optical defect center magnetometer 2500 also include a planar arrangement to reduce a z-direction size of the magneto-optical defect center magnetometer 2500. The reduced z-direction size may be useful for positioning the magneto-optical defect center magnetometer 2500 in a vehicle or other device to control for any vibratory influences and/or space constraints. Moreover, in some implementations, the size and/or weight of the magneto-optical defect center magnetometer 2500 may be important. For instance, magneto-optical defect center aircraft, size and weight may be tightly controlled, so a small z-directional size may permit the magneto-optical defect center magnetometer to be positioned on a bulkhead and/or within a cockpit with minimal space impact. Moreover, the high stiffness and low mass of the top plate 2510 and bottom plate 2520 limit the weight of the magneto-optical defect center magnetometer 2500.

The planar arrangement of the components of the magneto-optical defect center magnetometer 2500 may also be useful. The planar arrangement allows for the excitation source, such as the green laser diode 2610, and the collection device, such as the one or more photo diodes 2618, to be positioned anywhere in the plane, thereby permitting varying configurations for the magneto-optical defect center magnetometer 2500 to accommodate space constraints. Further still, the planar configuration also permits multiple excitation sources and/or collection devices to be utilized by the magneto-optical defect center magnetometer 2500. As shown in FIGS. 25-31, a primary green laser diode 2610 and a flash laser 2628 can be used as excitation sources, while two light pipes 2634 and photo diodes 2618 are utilized for collection devices. Of course additional excitation sources and/or collection devices may be used as well. The planar arrangement of the components of the magneto-optical defect center magnetometer 2500 is also beneficial for the mounting of optical components, such as the laser diodes, focusing lenses, light pipes, etc. on the PCB 2522 because the planar arrangement limits any z-direction variability such that alignment using the pins and alignment openings positions the optical components in a known position relative to the other components of the magneto-optical defect center magnetometer 2500. Further still, the planar arrangement of the components of the magneto-optical defect center magnetometer 2500 provides a controlled reference plane for determining the vector of the detected external magnetic field. Still further, the planar arrangement permits usage of the mirror and/or filtering element 2632 that can be configured to confine any and/or substantially all of the emitted red light from the magneto-optical defect center element to within a small z-direction area to be directed toward the one or more photo diodes 2618. That is, the mirror and/or filtering element 2632 can be configured to direct any emitted red wavelength light from the magneto-optical defect center element to within the plane defined by the planar arrangement.

In some implementations, the magneto-optical defect center magnetometer 2500 may have a weight of less than 0.5 kilograms, a range of power of 1-5 watts, and a size of approximately 7.62 centimeters in the x-direction by 10.16 centimeters in the y-direction by 1.905 centimeters in the z-direction. The magneto-optical defect center magnetometer 2500 may have a resolution of approximately 300 picoteslas, a bandwidth of 1 MHz, and a measurement range of 1000 microteslas.

Figure 33:
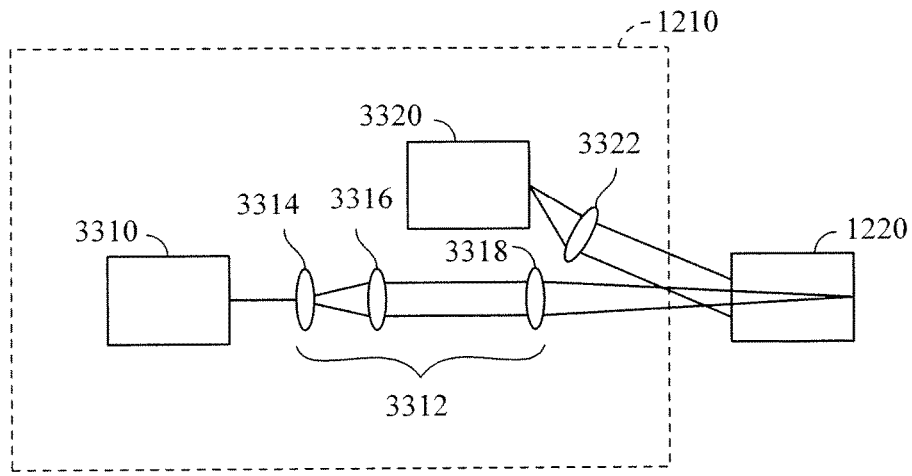
FIG. 33 is a schematic illustrating details of the optical light source of the magnetic field detection system of FIG. 12 according to some embodiments.

FIG. 33 is a schematic illustrating details of the optical light source 1210. The optical light source 1210 may include a readout optical light source 3310 and reset optical light source 3320. The readout optical light source 3310 may be a laser or a light emitting diode, for example, which emits light in the green, for example. The readout optical light source 3310 induces fluorescence in the red from the NV diamond material 1220, where the fluorescence corresponds to an electronic transition of the NV electron pair from the excited state to the ground state. Referring back to FIG. 12, light from the NV diamond material 1220 is directed through the optical filter 1250 to filter out light in the excitation band (in the green, for example), and to pass light in the red fluorescence band, which in turn is detected by the optical detector 1240. Thus, the readout optical light source 3310 induces fluorescence which is then detected by the optical detector 1240, i.e., the fluorescence induced by the readout optical light source 3310 is read out.

The reset optical light source 3320 of the optical light source 1210 serves to reset the population of the ms=0 spin state of the ground state 3A2 to a maximum polarization, or other desired polarization. In general, it may be desired in a reset stage to reset the spin population to the desired spin state relatively quickly to reduce the reset time, and thus to increase sensor bandwidth. In this case the reset optical light source 3320 provides light of a relatively high power. Further, the reset optical light source 3320 may have a lower duty cycle than readout optical light source 3310, thus providing reduced heating of the system.

On the other hand, a relatively lower power may be desired for the readout optical light source 3310 to provide a higher accuracy readout. The relatively lower power readout optical light source 3310 beneficially allows for easier control of the spectral purity, a slower readout time with lower noise, reduced laser heating, and may be light weight and compact. Thus, the reset optical light source 3320 may provide light of a higher power than that of the readout optical light source 3310. The readout optical light source 3310 does provide some amount of a reset function. However, a lower powered light source takes longer to provide a reset and thus is tolerable.

Thus, the higher powered reset optical light source 3320 provides advantages such as decreasing the time required for reset. Moreover, the higher powered reset optical light source 3320 clears the previous polarization of the spin states of the NV centers. This may be important particularly in the case where the previous polarization is at another frequency pertaining to a different NV center crystallographic orientation. This is applicable to both pulse excitation schemes such as RF pulse sequence or spin-echo pulse sequence, as well as for continuous wave excitation where the RF field is scanned during the continuous wave excitation. For example, for continuous wave excitation where the RF field is scanned, the reset optical light source 3320 may reduce the time required to jump between Lorentzians, and clears out prior residual RF information, for, for example, vector magnetometry or thermally compensated scalar magnetometry. This reduction of time allows for better vector estimation and/or increased sampling bandwidth. Thus the benefits of a higher power reset optical light source of lower duty cycle, wider beamwidth, and stronger power apply to either pulsed or continuous wave applications.

This combination of two optical light sources, one with a relatively high power to provide reset of the spin polarization and another to induce fluorescence for the readout provides a system with shorter reset times, while at the same time providing a high accuracy readout. The ratio of the power of the reset optical light source 3320 to the readout optical light source 3310 may be 10 to 1 or 20 to 1, or greater, for example.

Further the two optical light source magnetometer systems described herein improve the efficiency of the magnetometer by allowing for sensitive optical collection to be performed over a longer period using a low light density, low noise, light source while maintaining reasonable repolarization and reset times with a higher power light source when measurements are not critical. These two optical light source magnetometer systems allow for optimization of sensitivity via full excitation power versus collection integration time trade space, and further improves SWaP-C (size, weight, power and cost) design space by tailoring excitation source performance to specific needs.

The readout optical light source 3310 may be a laser or an LED, for example, while the reset optical light source 3320 may a laser, or an LED. Exemplary arrangements are as follows. The readout optical light source 3310 may be a lower powered laser, and the reset optical light source 3320 may be a higher powered laser with a lower duty cycle. The readout optical light source 3310 may be a lower powered laser, and the reset optical light source 3320 may be a bank of LED flash-bulbs. The readout optical light source 3310 may be an LED, and the reset optical light source 3320 may be a bank of LED flash-bulbs.

Reset and Read Out Illumination Volumes

Referring to FIG. 33, the optical light source 1210 may include a focusing lens 3322 to focus light from the reset optical light source 3320 onto the NV diamond material 1220. Similarly, the optical light source 1210 may include focusing optics 3312 to focus light from the readout optical light source 3310 onto the NV diamond material 1220. For example, the focusing optics 3312 may include lenses 3314, 3316, and 3318.

Figure 34:
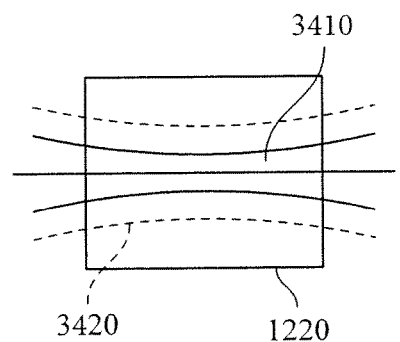
FIG. 34 illustrates the illumination volume in NV diamond material for a readout optical light source and a reset optical light source of the optical light source of the magnetic field detection system of FIG. 12 according to an embodiment.

FIG. 34 illustrates the illumination volume 3410 of the light beam from the readout optical light source 3310 and the illumination volume 3420 of the light beam from the reset optical light source 3320 in the diamond material 1220. The illumination volume 3410 is shown between solid lines in FIG. 34, while the illumination volume 3420 is shown between the dashed lines. The focusing optics 3312 reduces the size of the illumination volume 3410 of the diamond material 1220 which is illuminated with the excitation beam from the readout optical light source 3310. In general, the illumination volume depends on the spot size of the focused light beam in the diamond material 1220. By reducing the illumination volume 3410 in the diamond material 1220, a higher light density for a given readout optical light source 3310 power is achieved, and further magnetic bias field inhomogeneities and RF field variations over the optically excited region of the diamond material can be reduced.

On the other hand, the illumination volume 3420 of the diamond material 1220 which is illuminated by the reset optical light source 3320 does not need to be as small as that for the readout optical light source 3310. The illumination volume 3420 of the diamond material 1220 which is illuminated by the reset optical light source 3320 should encompass the illumination volume 3410 of the diamond material 1220 which is illuminated by the readout optical light source 3310. In this way the reset optical light source 3320 will act to reset the NV spin states in the region of the diamond material 1220 which will be illuminated with the readout optical light source 3310.

Continuous Wave/RF Pulse Sequence Example

The present system may be used for continuous optical excitation, or pulsed excitation, such as modified Ramsey pulse sequence, modified Hahn-Echo, or modified spin echo pulse sequence. This section describes an exemplary continuous wave/pulse (cw-pulse) sequence. According to certain embodiments, the controller 1280 controls the operation of the optical light source 1210, the RF excitation source 1230, and the magnetic field generator 1270 to perform Optically Detected Magnetic Resonance (ODMR). The component of the magnetic field Bz along the NV axis of NV centers aligned along directions of the four different orientation classes of the NV centers may be determined by ODMR, for example, by using an ODMR pulse sequence according to a pulse sequence. The pulse sequence is a pulsed RF scheme that measures the free precession of the magnetic moment in the NV diamond material 1220 and is a technique that quantum mechanically prepares and samples the electron spin state.

Figure 35:
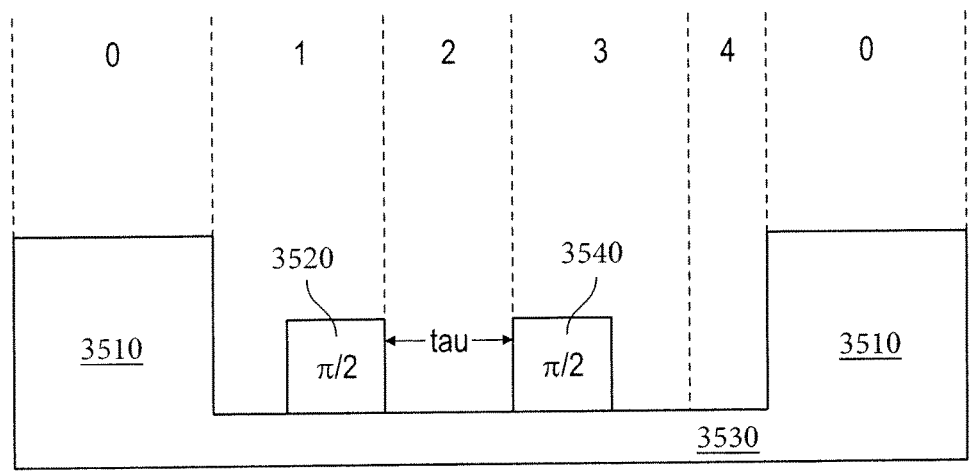
FIG. 35 illustrates a RF sequence according to some embodiments.

FIG. 35 is a timing diagram illustrating the continuous wave/pulse sequence. As shown in FIG. 35, a cw-pulse sequence includes optical excitation pulses and RF excitation pulses over a five-step period. In a first step, during a period 0, a first optical reset pulse 3510 from the reset optical light source 3320 is applied to the system to optically pump electrons into the ground state (i.e., ms=0 spin state). This is followed by a first RF excitation pulse 3520 (in the form of, for example, a microwave (MW) $\pi/2$ pulse), provided by the RF excitation source 1230, during a period 1. The first RF excitation pulse 3520 sets the system into superposition of the ms=0 and ms=+1 spin states (or, alternatively, the ms=0 and ms=−1 spin states, depending on the choice of resonance location). During a period 2, the system is allowed to freely precess (and accumulate phase) over a time period referred to as tau ($\tau$). Next, a second RF excitation pulse 3540 (in the form of, for example, a MW $\pi/2$ pulse) is applied during a period 3 to project the system back to the ms=0 and ms=+1 basis. During period 4 which corresponds to readout, optical light 3530 is provided by the readout optical light source 3310, to optically sample the system and a measurement basis is obtained by detecting the fluorescence intensity of the system. The optical light 3530 may be provided as an optical pulse, or as discussed further below, in a continuous manner throughout periods 0 through 4. Finally, the first optical reset pulse 3510 from the reset optical light source 3320 is applied again to begin another cycle of the cw-pulse sequence.

When the first optical reset pulse 3510 is applied again to reset to the ground state at the beginning of another sequence, the readout stage is ended. The cw-pulse sequence shown in FIG. 35 may be performed multiple times, wherein each of the MW pulses applied to the system during a given cw-pulse sequence includes a different frequency over a frequency range that includes RF frequencies corresponds to different NV center orientations. The magnetic field may be then be determined based on the readout values of the fluorescence change correlated to unknown magnetic fields.

Low Power Continuous Optical Excitation for RF Pulse Sequence

Referring back to FIG. 35, the optical light 3530 is provided by the readout optical light source 3310 in a continuous optical excitation manner. This provides a number of advantages over systems which turn on and off the light source providing light for optical readout during a RF sequence. Such systems which turn on and off the light source are susceptible to jitter noise interfering with the RF excitation source, and address this issue by increasing the laser light path length using optics so as to not be close to the RF excitation source, or by including a digital current source for the laser, for example.

By operating the readout optical light source 3310 in a continuous optical excitation manner, the system provides a number of advantages. The system does not need extra components such as an acousto-optic modulator (AOM), or a digital current source. Further, optics, such as mirrors and lenses, are not needed to increase the path length of the laser light path. Thus, the system may be less expensive. Still further, there is no need to synchronize turning on and off the light from readout optical light source 3310 with the RF excitation source, since the readout optical light source 3310 remains continuously on during the RF pulse sequence.

For the continuous optical excitation for RF pulse sequence, the readout optical light source 3310 is continuously on during the sequence, and thus continuously performs some amount of reset to the ground state throughout the sequence. Since the readout optical light source 3310 provides a relatively low power beam, however, the reset is tolerable.

Figure 36:
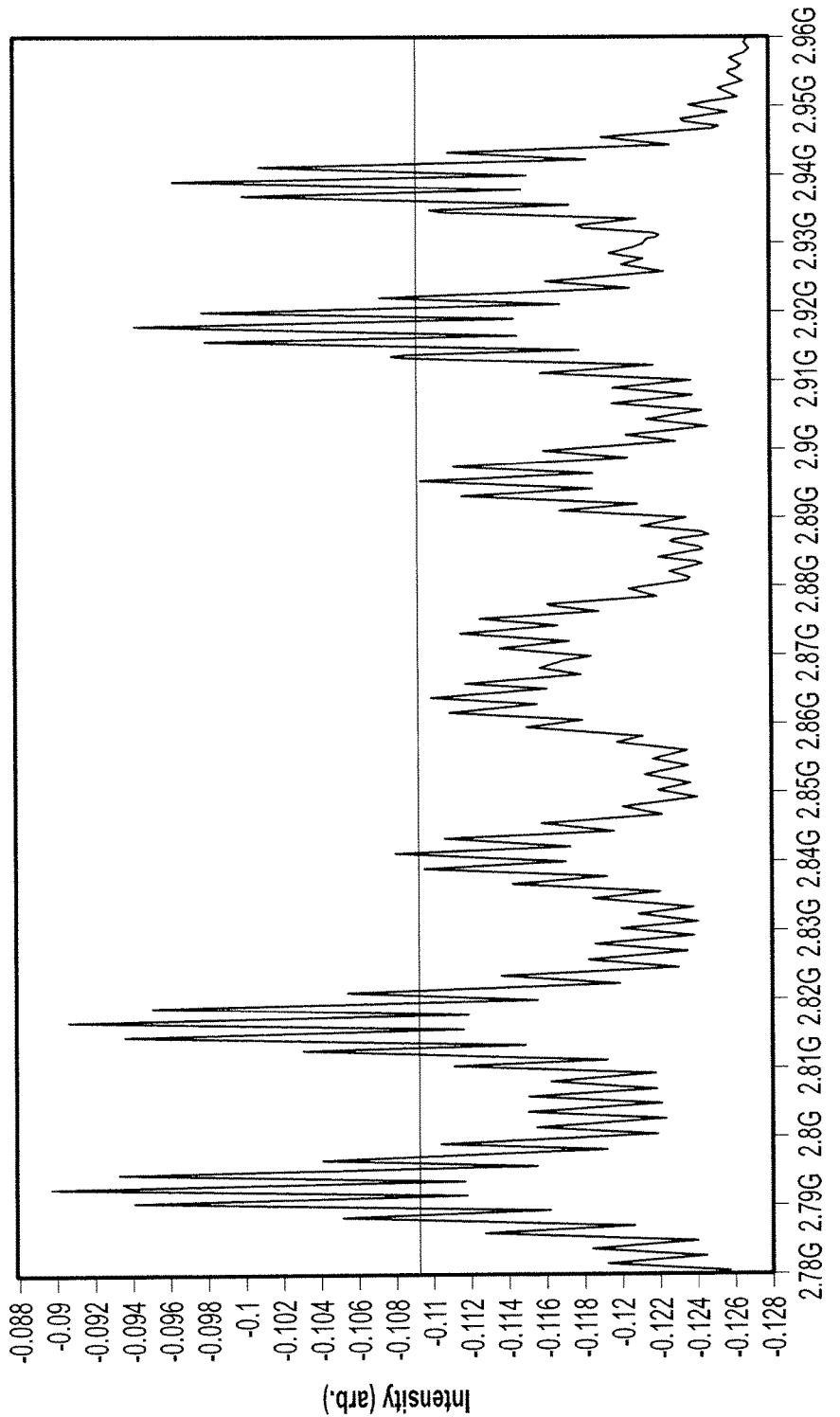
FIG. 36 is a magnetometry curve in the case of a continuous optical excitation RF pulse sequence according to some embodiments.
Figure 37:
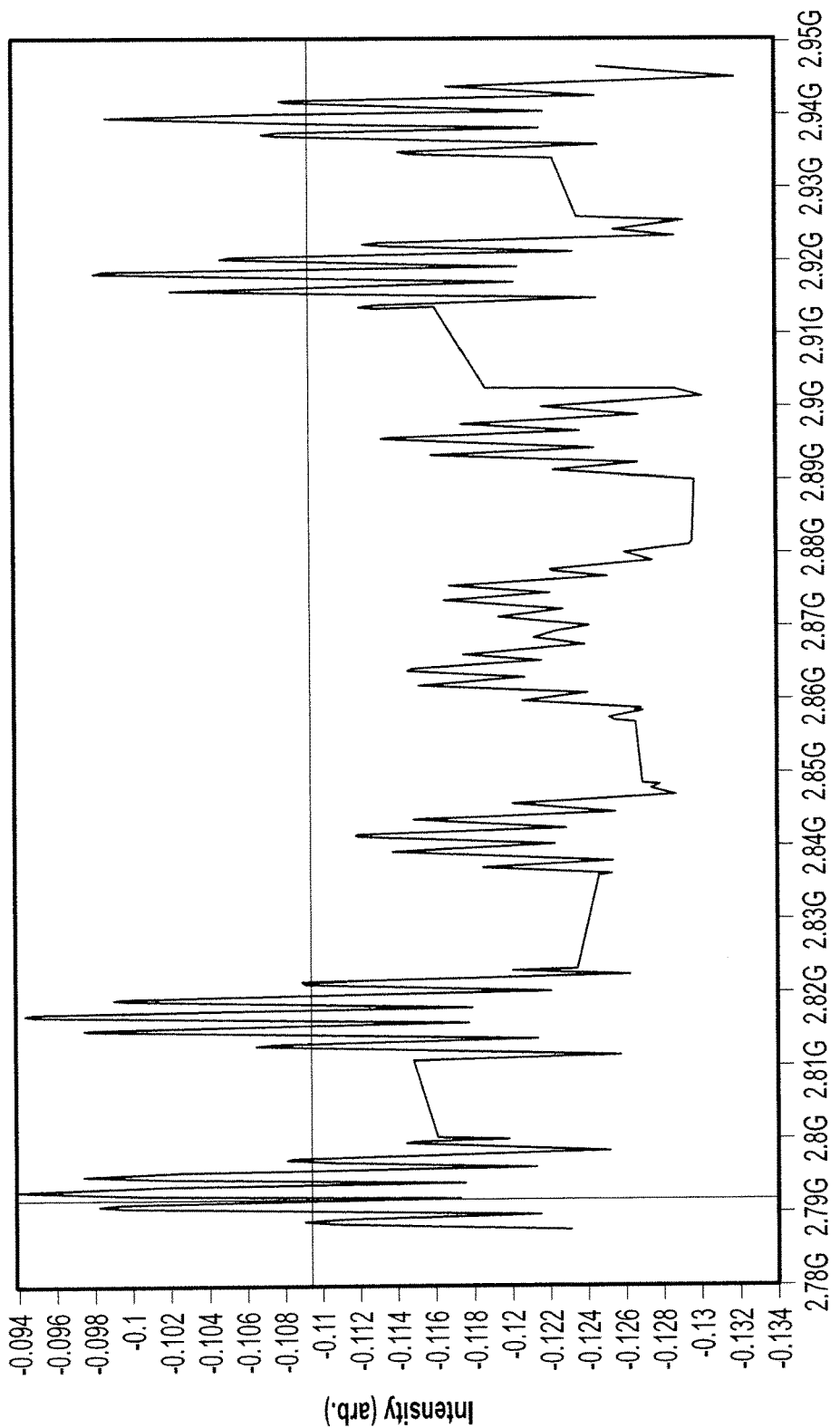
FIG. 37 is a magnetometry curve in the case of a continuous optical excitation RF pulse sequence where the waveform has been optimized for collection intervals according to some embodiments.

FIG. 36 illustrates a magnetometry curve in the case of using a continuous optical excitation RF pulse sequence. FIG. 36 shows the dimmed luminescence intensity at readout as a function of RF frequency applied during the RF pulse sequences. As can be seen, there are 8 spin state transition envelopes, each having a respective resonance frequency, for the case where the diamond material has NV centers aligned along directions of four different orientation classes. This is similar to the 8 spin state transitions shown in FIG. 5 for continuous wave optical excitation where the RF frequency is scanned. The magnetic field component along each of the four different orientation classes can be determined in a similar manner to that in FIG. 5. FIG. 37 illustrates a magnetometry curve similar to that of FIG. 36, where the RF waveform, including $\tau$, has been optimized for each ~12.5 MHz collection interval.

Figure 38:
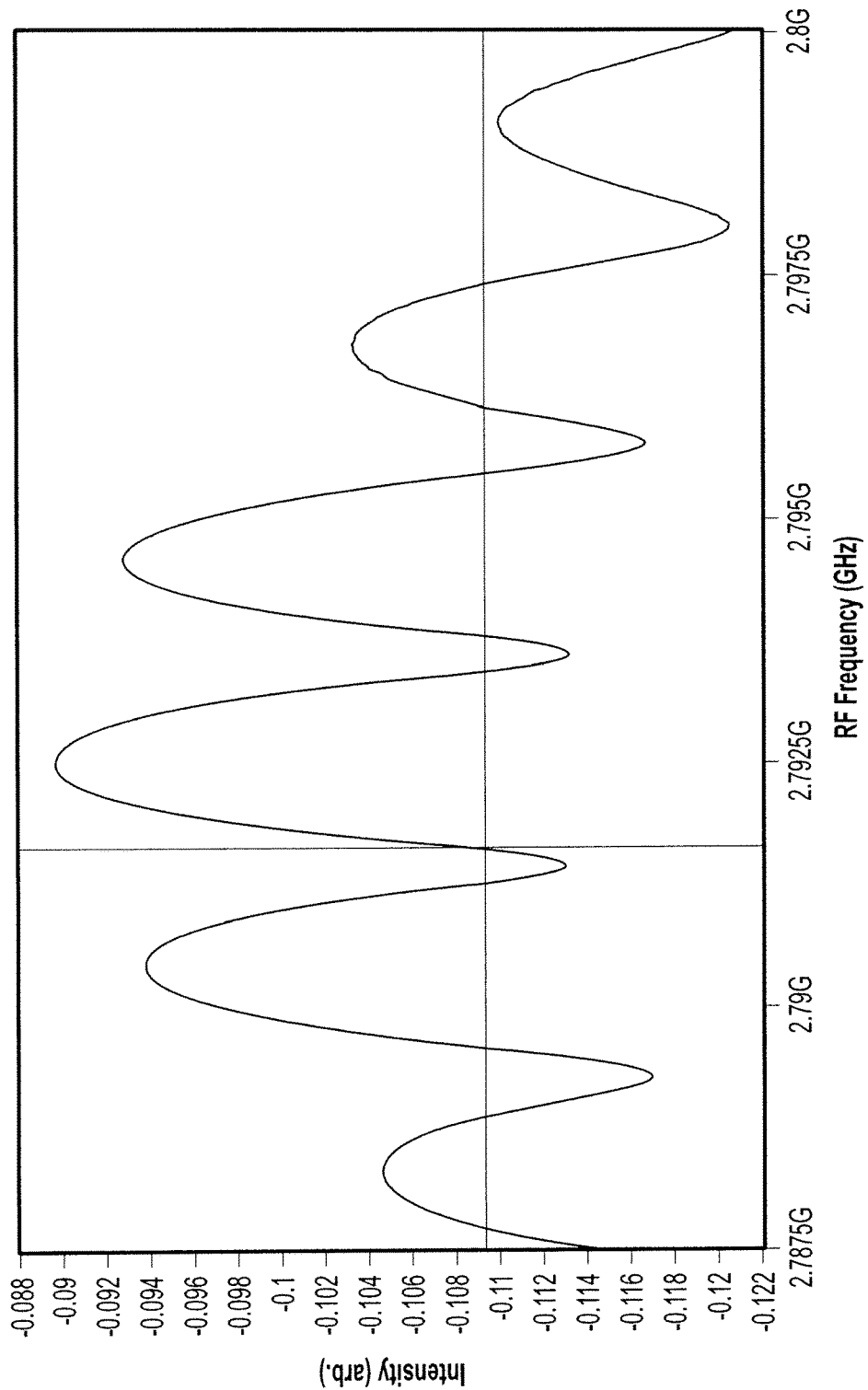
FIG. 38 is magnetometry curve for the left most resonance frequency of FIG. 37 according to some embodiments.
Figure 39:
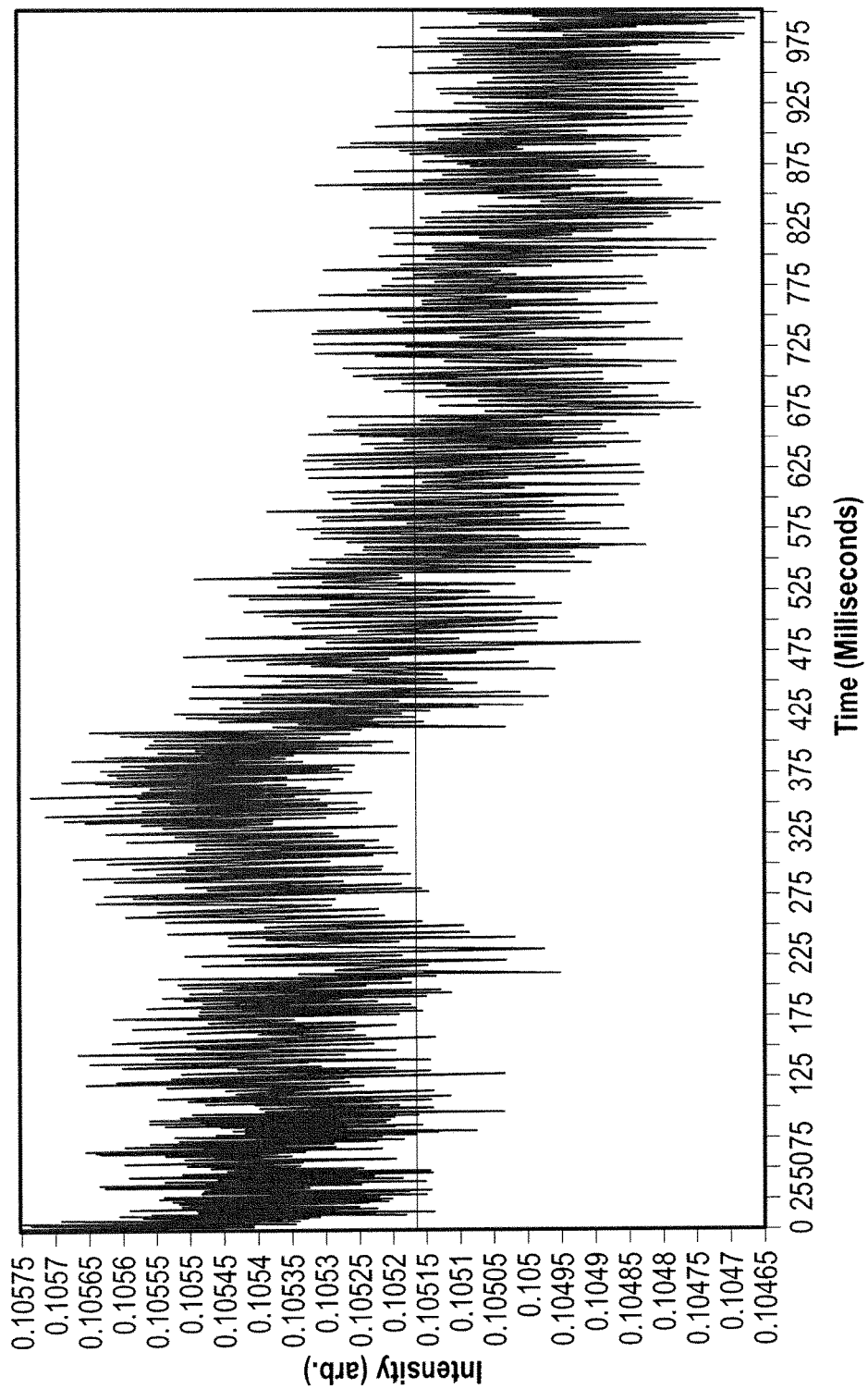
FIG. 39 is a graph illustrating the dimmed luminescence intensity as a function of time for the region of maximum slope of FIG. 38.

FIG. 38 illustrates a magnetometry curve for the left most resonance frequency of FIG. 37. In monitoring the magnetic field, the dimmed luminescence intensity, i.e., the amount the fluorescence intensity diminishes from the case where the spin states have been set to the ground state, of the region having the maximum slope may be monitored. If the dimmed luminescence intensity does not change with time, the magnetic field component does not change. A change in time of the dimmed luminescence intensity indicates that the magnetic field is changing in time, and the magnetic field may be determined as a function of time. For example, FIG. 39 illustrates the dimmed luminescence intensity as a function of time for the region of the maximum slope of FIG. 38.

Figure 40:
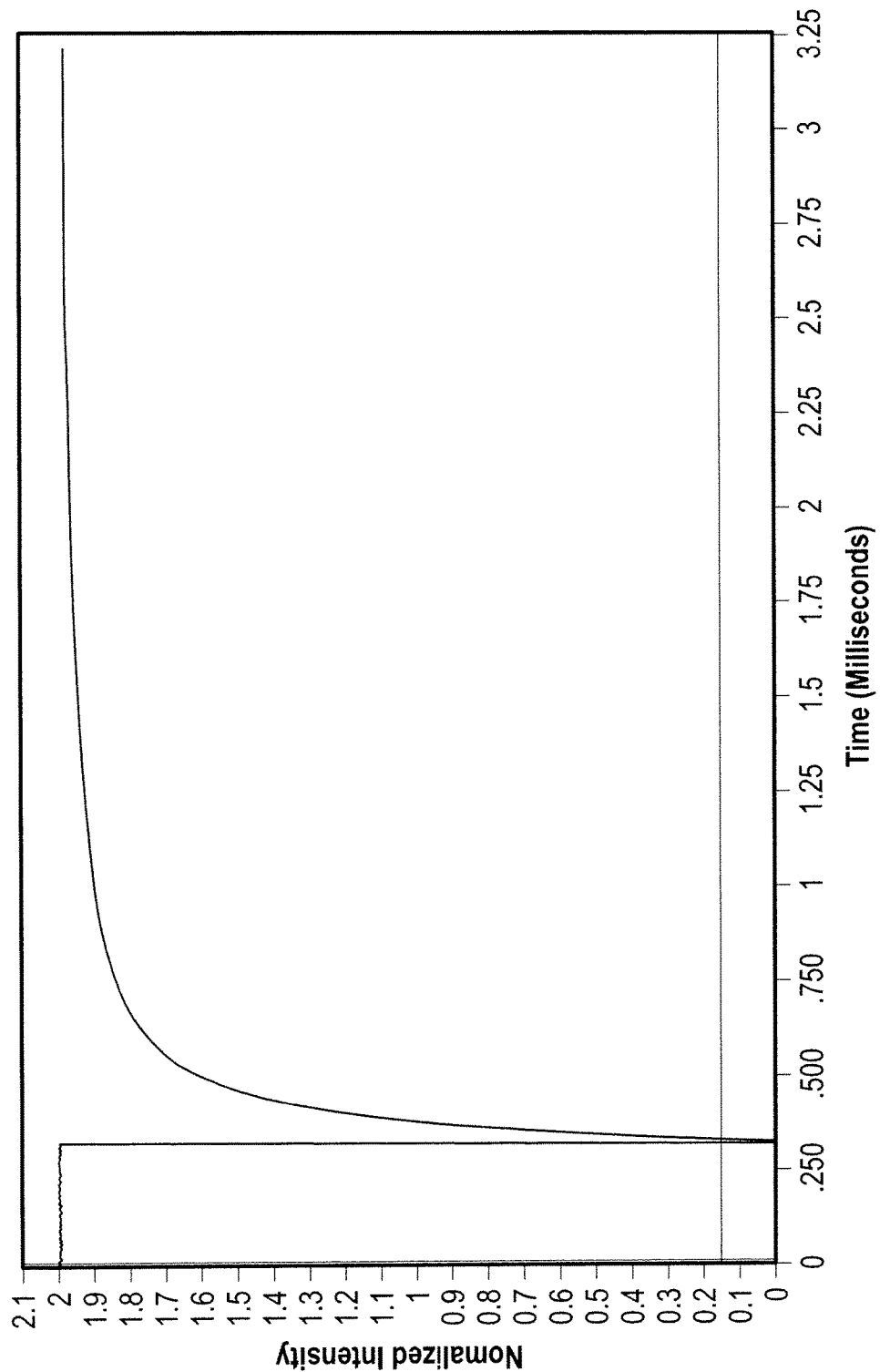
FIG. 40 is a graph illustrating the normalized intensity of the luminescence as a function of time for diamond NV material for a continuous optical illumination of the diamond NV material in a RF sequence measurement.
Figure 41:
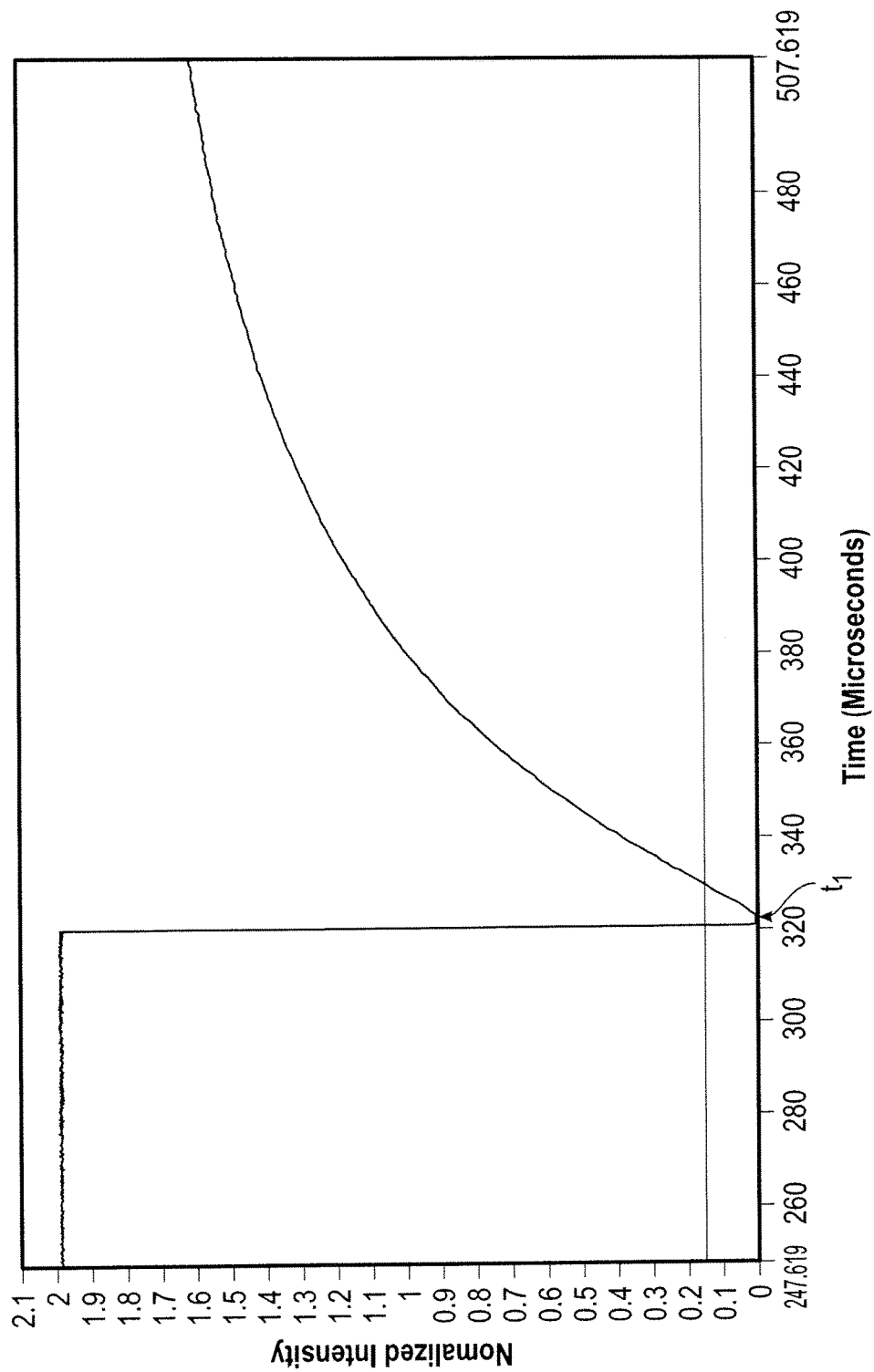
FIG. 41 is a graph of a zoomed in region of FIG. 40.

FIG. 40 illustrates the normalized intensity of the luminescence as a function of time for diamond NV material for a continuous optical illumination of the diamond NV material during a time which includes application of RF excitation according to a RF pulse sequence. Initially, the NV centers have all been reset to the ground state and the normalized intensity has a maximum value. At a time t1, RF excitation according to a RF sequence is applied and the normalized polarization drops to a minimum value. The normalized intensity continues to increase after t1 as the ground state population continues to increase. FIG. 41 illustrates a zoomed in region of FIG. 40 including time t1. The intensity may be read out for a time starting after t1 and integrated. The time at which the read out stops and high power reset begins may be set based on the application.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

While the above discussion primarily refers to circuits and/or circuitry, the circuits may include a microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

The description of the subject technology is provided to enable any person skilled in the art to practice the various embodiments described herein. While the subject technology has been particularly described with reference to the various figures and embodiments, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these embodiments may be readily apparent to those skilled in the art, and generic principles defined herein may be applied to other embodiments. Thus, many changes and modifications may be made to the subject technology, by one having ordinary skill in the art, without departing from the scope of the subject technology.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A magneto-optical defect center magnetometer assembly comprising:
    a magneto-optical defect center element;
    an excitation source;
    a collection device;
    an optical waveguide assembly that includes an optical waveguide and at least one optical filter coating, the optical filter coating applied to a surface of the optical waveguide, wherein the optical waveguide assembly is configured to transmit light emitted from the magneto-optical defect center element to the collection device; and
    a printed circuit board;
    wherein the excitation source, the magneto-optical defect center element, and the collection device are each mounted to the printed circuit board.

2. The magneto-optical defect center magnetometer assembly of claim 1, wherein the optical waveguide comprises a light pipe.

3. The magneto-optical defect center magnetometer assembly of claim 1, wherein the optical filter coating transmits greater than about 99% of light with a wavelength of about 650 nm to about 850 nm.

4. The magneto-optical defect center magnetometer assembly of claim 1, wherein the optical filter coating transmits less than 0.1% of light with a wavelength of less than about 600 nm.

5. The magneto-optical defect center magnetometer assembly of claim 1, wherein the optical filter coating transmits greater than about 99% of light with a wavelength of about 650 nm to about 850 nm, and transmits less than 0.1% of light with a wavelength of less than about 600 nm.

6. The magneto-optical defect center magnetometer assembly of claim 1, wherein the optical filter coating is disposed on an end surface of the optical waveguide adjacent the collection device.

7. The magneto-optical defect center magnetometer assembly of claim 1, wherein a first optical filter coating is disposed on an end surface of the optical waveguide adjacent the collection device, and a second optical filter coating is disposed on an end surface of the optical waveguide adjacent the diamond having nitrogen vacancies.

8. The magneto-optical defect center magnetometer assembly of claim 1, wherein the light pipe has an aperture with a size that is smaller than a size of the collection device.

9. The magneto-optical defect center magnetometer assembly of claim 1, wherein the light pipe has an aperture with a size greater than a size of a surface of the magneto-optical defect center element adjacent to the light pipe.

10. The magneto-optical defect center magnetometer assembly of claim 1, wherein the light pipe has an aperture with a size that is smaller than a size of the collection device and greater than a size of a surface of the magneto-optical defect center element adjacent the light pipe.

11. The magneto-optical defect center magnetometer assembly of claim 1, wherein the optical waveguide assembly further comprises an optical coupling material disposed between the light pipe and the magneto-optical defect center element, and the optical coupling material is configured to optically couple the light pipe to the magneto-optical defect center element.

12. The magneto-optical defect center magnetometer assembly of claim 1, wherein the optical waveguide assembly further comprises an optical coupling material disposed between the light pipe and the collection device, and the optical coupling material is configured to optically couple the light pipe to the collection device.

13. The magneto-optical defect center magnetometer assembly of claim 1, wherein an end surface of the light pipe adjacent to the magneto-optical defect center element extends in a plane parallel to a surface of the magneto-optical defect center element adjacent to the light pipe.

14. The magneto-optical defect center magnetometer assembly of claim 1, further comprising a second optical waveguide assembly and a second collection device, wherein the second optical waveguide assembly is configured to transmit light emitted from the magneto-optical defect center element to the second collection device.

15. A magneto-optical defect center magnetometer assembly comprising:
   a magneto-optical defect center element;
   an excitation source;
   a collection device;
   a printed circuit board;
   an optical waveguide assembly that includes an optical waveguide and at least one optical filter coating, the optical filter coating applied to a surface of the optical waveguide, wherein the optical waveguide assembly is configured to transmit light emitted from the magneto-optical defect center element to the collection device;
   excitation source circuitry mounted to the printed circuit board proximate to the excitation source; and
   collection device circuitry mounted to the printed circuit board proximate to the collection device;
   wherein the excitation source, the magneto-optical defect center element, and the collection device are each mounted to the printed circuit board.

16. The magneto-optical defect center magnetometer assembly of claim 15, wherein the excitation source is positioned along a first axis relative to the printed circuit board and wherein the collection device is positioned along a second axis relative to the printed circuit board.

17. The magneto-optical defect center magnetometer assembly of claim 15 further comprising an RF element mounted to the printed circuit board and RF amplifier circuitry mounted to the printed circuit board proximate to the RF device.

18. The magneto-optical defect center magnetometer assembly of claim 15, further comprising an optical filter, wherein the magneto-optical defect center element receives optical excitation based, at least in part, on generation of light corresponding to a first wavelength from the excitation source, wherein the collection device is configured to receive at least a first portion of light corresponding to a second wavelength, and wherein the optical filter is configured to provide at least a portion of light corresponding to the second wavelength to the collection device.

19. The magneto-optical defect center magnetometer assembly of claim 15, wherein the excitation source comprises an optical light source including a readout optical light source configured to provide optical excitation to the magneto-optical defect center element to transition relevant magneto-optical defect electrons to excited spin states in the magneto-optical defect center element and a reset optical light source configured to provide optical light to the magneto-optical defect center element to reset spin states in the magneto-optical defect center element to a ground state, wherein the reset optical light source provides a higher power light than the readout optical light source.

20. The magneto-optical defect center magnetometer assembly of claim 15, further comprising a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils arranged in layers one above another and to have a uniform spacing between each other.

21. The magneto-optical defect center magnetometer assembly of claim 15, wherein the magneto-optical defect center element is a diamond having nitrogen vacancies.

22. The magneto-optical defect center magnetometer assembly of claim 15, wherein the excitation source, the magneto-optical defect center element, and the collection device are each aligned and positioned relative to the top plate, bottom plate, and printed circuit board by a corresponding two-point orientation system.

23. A magneto-optical defect center magnetometer assembly comprising:
   a magneto-optical defect center element;
   an excitation source;
   a collection device;
   an RF element;
   a printed circuit board;
   an optical waveguide assembly that includes an optical waveguide and at least one optical filter coating, the optical filter coating applied to a surface of the optical waveguide, wherein the optical waveguide assembly is configured to transmit light emitted from the magneto-optical defect center element to the collection device;
   excitation source circuitry mounted to the printed circuit board proximate to the excitation source;
   collection device circuitry mounted to the printed circuit board proximate to the collection device; and
   RF amplifier circuitry mounted to the printed circuit board proximate to the RF device;
   wherein the excitation source, the magneto-optical defect center element, the collection device, and the RF element are each mounted to the printed circuit board and wherein the excitation source is positioned along a first axis relative to the printed circuit board and wherein the collection device is positioned along a second axis relative to the printed circuit board.

24. The magneto-optical defect center magnetometer assembly of claim 23, further comprising an optical filter, wherein the magneto-optical defect center element receives optical excitation based, at least in part, on generation of light corresponding to a first wavelength from the excitation source, wherein the collection device is configured to receive at least a first portion of light corresponding to a second wavelength, and wherein the optical filter is configured to provide at least a portion of light corresponding to the second wavelength to the collection device.

25. The magneto-optical defect center magnetometer assembly of claim 23, wherein the excitation source, the magneto-optical defect center element, and the collection device are each aligned and positioned relative to the top plate, bottom plate, and printed circuit board by a corresponding two-point orientation system.

26. The magneto-optical defect center magnetometer assembly of claim 23, wherein the excitation source comprises an optical light source including a readout optical light source configured to provide optical excitation to the magneto-optical defect center element to transition relevant magneto-optical defect electrons to excited spin states in the magneto-optical defect center element and a reset optical light source configured to provide optical light to the magneto-optical defect center element to reset spin states in the magneto-optical defect center element to a ground state, wherein the reset optical light source provides a higher power light than the readout optical light source.

27. The magneto-optical defect center magnetometer assembly of claim 23, further comprising a radio frequency (RF) excitation source configured to provide RF excitation to the magneto-optical defect center element, the RF excitation source including an RF feed connector and a plurality of coils, each connected to the RF feed connector, and adjacent the magneto-optical defect center element, the coils arranged in layers one above another and to have a uniform spacing between each other.

28. The magneto-optical defect center magnetometer assembly of claim 23, wherein the magneto-optical defect center element is a diamond having nitrogen vacancies.

* * * * *